United States Patent
Liu et al.

(10) Patent No.: US 11,571,461 B2
(45) Date of Patent: Feb. 7, 2023

(54) METHODS OF USE OF SOLUBLE CD24 FOR TREATING LUPUS NEPHRITIS

(71) Applicant: ONCOIMMUNE, INC., Rockville, MD (US)

(72) Inventors: Yang Liu, Washington, DC (US); Pan Zheng, Washington, DC (US); Martin Devenport, Gaithersburg, MD (US)

(73) Assignee: ONCOIMMUNE, INC., Rockville, MD (US)

( * ) Notice: Subject to any disclaimer, the term of this patent is extended or adjusted under 35 U.S.C. 154(b) by 292 days.

(21) Appl. No.: 16/491,708

(22) PCT Filed: Mar. 6, 2018

(86) PCT No.: PCT/US2018/021214
§ 371 (c)(1),
(2) Date: Sep. 6, 2019

(87) PCT Pub. No.: WO2018/165204
PCT Pub. Date: Sep. 13, 2018

(65) Prior Publication Data
US 2022/0125874 A1 Apr. 28, 2022

Related U.S. Application Data

(60) Provisional application No. 62/468,049, filed on Mar. 7, 2017.

(51) Int. Cl.
| | |
|---|---|
| *C07K 14/47* | (2006.01) |
| *C07K 14/475* | (2006.01) |
| *C07K 14/705* | (2006.01) |
| *C07K 16/28* | (2006.01) |
| *C07K 19/00* | (2006.01) |
| *A61K 38/17* | (2006.01) |
| *A61K 38/18* | (2006.01) |
| *A61K 39/395* | (2006.01) |
| *A61P 37/06* | (2006.01) |

(52) U.S. Cl.
CPC ............ *A61K 38/177* (2013.01); *A61K 38/18* (2013.01); *A61K 39/3955* (2013.01); *A61P 37/06* (2018.01); *C07K 14/475* (2013.01); *C07K 14/4713* (2013.01); *C07K 14/70596* (2013.01); *C07K 16/2803* (2013.01); *C07K 19/00* (2013.01); *C07K 2319/00* (2013.01); *C07K 2319/30* (2013.01); *C07K 2319/91* (2013.01)

(58) Field of Classification Search
CPC ........ A61K 38/00; A61K 38/17; A61K 38/18; A61K 38/177; C07K 2319/00; C07K 19/00; C07K 14/4703; C07K 14/47; C07K 14/4713; C07K 14/475; C07K 2319/30; C07K 14/70596; C07K 2319/91
See application file for complete search history.

(56) References Cited

U.S. PATENT DOCUMENTS

| | | | | |
|---|---|---|---|---|
| 7,744,894 B2* | 6/2010 | Liu | .......................... | A61P 37/06 424/185.1 |
| 8,808,697 B2* | 8/2014 | Zheng | ..................... | A61P 37/00 424/134.1 |
| 2013/0296249 A1 | 11/2013 | Liu et al. | | |

FOREIGN PATENT DOCUMENTS

| | | |
|---|---|---|
| WO | 2011/139820 A1 | 11/2011 |
| WO | 2016/073704 A1 | 5/2016 |
| WO | 2016/179456 A1 | 11/2016 |

OTHER PUBLICATIONS

Bhattacharya et al. Impact of genetic variation on three dimensional structure and function of proteins. PLoS One 12(3): e0171355, 2017.*
Bork, P. Powers and pitfalls in sequence analysis: the 70% hurdle. Genome Res 10: 398-400, 2000.*
Bork, P. Go hunting in sequence databases but watch out for the traps. Trends in Genetics 12(10): 425-427, 1996.*
Brenner. S.E. Errors in genome annotation. Trends in Genetics 15:132-133, 1999.*
Doerks et al. Protein annotation: detective work for function prediction. Trends in Genetics 14:248-250, 1998.*
Fang et al. CD24: fro A to Z. Cell Mol Immunol 7: 100-103, 2010.*
Fenton et al. Rheostat positions: a new classification of protein positions relevant to pharmacogenomics. Medicinal Chem Res 29: 1133-1146, 2020.*
Guo et al. Protein tolerance to random amino acid change. Proc Natl Acad Sci USA 101(25): 9205-9210, 2004.*
Huang et al. Association between the CD24Ala57Val polymorphism and risk for multiple sclerosis and systemic lupus erythematosus: a meta-analysis. Sci Reports 5: 9557, 2015 (7 total pages).*
Liu et al. CD24: a genetic checkpoint in T cell homeostasis and autoimmune diseases. Trends Immunol 28(7): 315-320, 2007.*
Ngo et al. "Computational complexity, protein structure prediction, and the Levinthal paradox" in The Protein Folding Problem and Tertiary Structure Prediction, pp. 492-495, 1994.*
Piotrowski et al. CD24 Ala57Val gene polymorphism and the risk of systemic lupus erythematosis. Tissue Antigens 75: 696-700, 2009.*
Skolnick et al. From genes to protein structure and function: novel applications of computational approaches in the genomic era. Trends Biotechnol 18(I):34-39 2000.*
Smith et al. The challenges of genome sequence annotation or "the devil is in the details". Nature Biotechnol 15: 1222-1223, 1997.*
Tan et al. CD24: from a hematopoietic differentiation antigen to a genetic risk factor for multiple autoimmune diseases. Clinic Rev Allerg Immunol 50: 70-83, 2016.*
Tokuriki et al. Stability effects of mutations and protein evolvability. Curr Opin Structural Biol 19: 596-604, 2009.*

(Continued)

*Primary Examiner* — Bridget E Bunner
(74) *Attorney, Agent, or Firm* — Sylvia A. Ayler; Catherine D. Fitch

(57) ABSTRACT

The present invention relates to the use of a CD24 protein for treating Systemic Lupus Erythematosus (Lupus, SLE).

11 Claims, 26 Drawing Sheets

Specification includes a Sequence Listing.

(56) References Cited

OTHER PUBLICATIONS

Wells, J.A. Additivity of mutational effects in proteins. Biochemistry 29(37): 8509-8517, 1990.*
Medina-Rosas et al. Proteinuria: Assessment and utility in lupus nephritis. J Orthop Res Physiother 2: 027, 2016 (8 total pages).*
Sanchez, E., et al., "Association of a CD24 Gene Polymorphism with Susceptibility to Systemic Lupus Erythematosus," Arthritis & Rheumatism, vol. 56, No. 9, pp. 3080-3086 (Sep. 2007).
Wang, L., et al., "A Dinucleotide Deletion in CD24 Confers Protection Against Autoimmune Diseases," PLoS Genetics, vol. 3, No. 4, e49 pp. 0508-0517 (Apr. 6, 2007 published on-line).

* cited by examiner

FIG. 1A

MGRAMVARLGLGLLLLALLLPTQIYS**SETTTGTSSNSSQSTSNSGLAP
NPTNATTK**PKSCDKTHTCPPCPAPELLGGPSVFLFPPKPKDTLMISRT
PEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLP
PSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK

FIG. 1B

MGRAMVARLGLGLLLLALLLPTQIYS**SETTTGTSSNSSQSTSNSGLAP
NPTNATTKV**PKSCDKTHTCPPCPAPELLGGPSVFLFPPKPKDTLMISR
TPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTL
PPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK

FIG. 1C

MGRAMVARLGLGLLLLALLLPTQIYS**SETTTGTSSNSSQSTSNSGLAP
NPTNATTKA**PKSCDKTHTCPPCPAPELLGGPSVFLFPPKPKDTLMISR
TPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTL
PPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK

FIG. 2

```
Mouse CD24 NQTSVAPFPGN--QNISAS----PNPTNATTRG
           -*  -      *  *  * *       ********--
Human CD24 SETTTGTSS-NSSQSTSNS-GLAPNPTNATTKA(V)
```

The dose dependant therapeutic effect of CD24Fc

SEQUENCE LISTING

<160> NUMBER OF SEQ ID NOS: 12

<210> SEQ ID NO 1
<211> LENGTH: 31
<212> TYPE: PRT
<213> ORGANISM: Homo sapiens
<220> FEATURE:
<221> NAME/KEY: X
<222> LOCATION: (31)..(31)
<223> OTHER INFORMATION: Valine or Alanine

<400> SEQUENCE: 1

```
Ser Glu Thr Thr Thr Gly Thr Ser Ser Asn Ser Ser Gln Ser Thr Ser
1               5                   10                  15

Asn Ser Gly Leu Ala Pro Asn Pro Thr Asn Ala Thr Thr Lys Xaa
            20                  25                  30
```

<210> SEQ ID NO 2
<211> LENGTH: 30
<212> TYPE: PRT
<213> ORGANISM: Homo sapiens

<400> SEQUENCE: 2

```
Ser Glu Thr Thr Thr Gly Thr Ser Ser Asn Ser Ser Gln Ser Thr Ser
1               5                   10                  15

Asn Ser Gly Leu Ala Pro Asn Pro Thr Asn Ala Thr Thr Lys
            20                  25                  30
```

<210> SEQ ID NO 3
<211> LENGTH: 27
<212> TYPE: PRT
<213> ORGANISM: Mus musculus

<400> SEQUENCE: 3

```
Asn Gln Thr Ser Val Ala Pro Phe Pro Gly Asn Gln Asn Ile Ser Ala
1               5                   10                  15

Ser Pro Asn Pro Thr Asn Ala Thr Thr Arg Gly
            20                  25
```

<210> SEQ ID NO 4
<211> LENGTH: 26
<212> TYPE: PRT
<213> ORGANISM: Homo sapiens

<400> SEQUENCE: 4

```
Met Gly Arg Ala Met Val Ala Arg Leu Gly Leu Gly Leu Leu Leu Leu
1               5                   10                  15

Ala Leu Leu Leu Pro Thr Gln Ile Tyr Ser
            20                  25
```

<210> SEQ ID NO 5
<211> LENGTH: 287
<212> TYPE: PRT
<213> ORGANISM: Artificial
<220> FEATURE:
<223> OTHER INFORMATION: Fusion protein

<400> SEQUENCE: 5

```
Met Gly Arg Ala Met Val Ala Arg Leu Gly Leu Gly Leu Leu Leu Leu
1               5                   10                  15

Ala Leu Leu Leu Pro Thr Gln Ile Tyr Ser Ser Glu Thr Thr Thr Gly
            20                  25                  30

Thr Ser Ser Asn Ser Ser Gln Ser Thr Ser Asn Ser Gly Leu Ala Pro
        35                  40                  45

Asn Pro Thr Asn Ala Thr Thr Lys Pro Lys Ser Cys Asp Lys Thr His
    50                  55                  60

Thr Cys Pro Pro Cys Pro Ala Pro Glu Leu Leu Gly Gly Pro Ser Val
65                  70                  75                  80

Phe Leu Phe Pro Pro Lys Pro Lys Asp Thr Leu Met Ile Ser Arg Thr
                85                  90                  95

Pro Glu Val Thr Cys Val Val Val Asp Val Ser His Glu Asp Pro Glu
            100                 105                 110
```

Val Lys Phe Asn Trp Tyr Val Asp Gly Val Glu Val His Asn Ala Lys
            115                 120                 125

Thr Lys Pro Arg Glu Glu Gln Tyr Asn Ser Thr Tyr Arg Val Val Ser
    130                 135                 140

Val Leu Thr Val Leu His Gln Asp Trp Leu Asn Gly Lys Glu Tyr Lys
145                 150                 155                 160

Cys Lys Val Ser Asn Lys Ala Leu Pro Ala Pro Ile Glu Lys Thr Ile
                165                 170                 175

Ser Lys Ala Lys Gly Gln Pro Arg Glu Pro Gln Val Tyr Thr Leu Pro
            180                 185                 190

Pro Ser Arg Asp Glu Leu Thr Lys Asn Gln Val Ser Leu Thr Cys Leu
    195                 200                 205

Val Lys Gly Phe Tyr Pro Ser Asp Ile Ala Val Glu Trp Glu Ser Asn
210                 215                 220

Gly Gln Pro Glu Asn Asn Tyr Lys Thr Thr Pro Pro Val Leu Asp Ser
225                 230                 235                 240

Asp Gly Ser Phe Phe Leu Tyr Ser Lys Leu Thr Val Asp Lys Ser Arg
                245                 250                 255

Trp Gln Gln Gly Asn Val Phe Ser Cys Ser Val Met His Glu Ala Leu
            260                 265                 270

His Asn His Tyr Thr Gln Lys Ser Leu Ser Leu Ser Pro Gly Lys
    275                 280                 285

<210> SEQ ID NO 6
<211> LENGTH: 261
<212> TYPE: PRT
<213> ORGANISM: Artificial
<220> FEATURE:
<223> OTHER INFORMATION: Fusion protein

<400> SEQUENCE: 6

Ser Glu Thr Thr Thr Gly Thr Ser Ser Asn Ser Ser Gln Ser Thr Ser
1               5                   10                  15

Asn Ser Gly Leu Ala Pro Asn Pro Thr Asn Ala Thr Thr Lys Pro Lys
            20                  25                  30

Ser Cys Asp Lys Thr His Thr Cys Pro Pro Cys Pro Ala Pro Glu Leu
        35                  40                  45

Leu Gly Gly Pro Ser Val Phe Leu Phe Pro Pro Lys Pro Lys Asp Thr
    50                  55                  60

Leu Met Ile Ser Arg Thr Pro Glu Val Thr Cys Val Val Val Asp Val
65                  70                  75                  80

Ser His Glu Asp Pro Glu Val Lys Phe Asn Trp Tyr Val Asp Gly Val
                85                  90                  95

Glu Val His Asn Ala Lys Thr Lys Pro Arg Glu Glu Gln Tyr Asn Ser
            100                 105                 110

Thr Tyr Arg Val Val Ser Val Leu Thr Val Leu His Gln Asp Trp Leu
        115                 120                 125

Asn Gly Lys Glu Tyr Lys Cys Lys Val Ser Asn Lys Ala Leu Pro Ala
    130                 135                 140

Pro Ile Glu Lys Thr Ile Ser Lys Ala Lys Gly Gln Pro Arg Glu Pro
145                 150                 155                 160

Gln Val Tyr Thr Leu Pro Pro Ser Arg Asp Glu Leu Thr Lys Asn Gln
                165                 170                 175

Val Ser Leu Thr Cys Leu Val Lys Gly Phe Tyr Pro Ser Asp Ile Ala
            180                 185                 190

```
Val Glu Trp Glu Ser Asn Gly Gln Pro Glu Asn Asn Tyr Lys Thr Thr
        195                 200                 205

Pro Pro Val Leu Asp Ser Asp Gly Ser Phe Phe Leu Tyr Ser Lys Leu
    210                 215                 220

Thr Val Asp Lys Ser Arg Trp Gln Gln Gly Asn Val Phe Ser Cys Ser
225                 230                 235                 240

Val Met His Glu Ala Leu His Asn His Tyr Thr Gln Lys Ser Leu Ser
                245                 250                 255

Leu Ser Pro Gly Lys
            260
```

<210> SEQ ID NO 7
<211> LENGTH: 231
<212> TYPE: PRT
<213> ORGANISM: Homo sapiens

<400> SEQUENCE: 7

```
Pro Lys Ser Cys Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230
```

<210> SEQ ID NO 8
<211> LENGTH: 288
<212> TYPE: PRT
<213> ORGANISM: Artificial
<220> FEATURE:
<223> OTHER INFORMATION: Fusion protein

<400> SEQUENCE: 8

Met Gly Arg Ala Met Val Ala Arg Leu Gly Leu Gly Leu Leu Leu Leu

-continued

```
   1               5                  10                 15
Ala Leu Leu Leu Pro Thr Gln Ile Tyr Ser Ser Glu Thr Thr Thr Gly
                20                  25                  30

Thr Ser Ser Asn Ser Ser Gln Ser Thr Ser Asn Ser Gly Leu Ala Pro
                35                  40                  45

Asn Pro Thr Asn Ala Thr Thr Lys Val Pro Lys Ser Cys Asp Lys Thr
 50                  55                  60

His Thr Cys Pro Pro Cys Pro Ala Pro Glu Leu Leu Gly Gly Pro Ser
 65                  70                  75                  80

Val Phe Leu Phe Pro Pro Lys Pro Lys Asp Thr Leu Met Ile Ser Arg
                85                  90                  95

Thr Pro Glu Val Thr Cys Val Val Asp Val Ser His Glu Asp Pro
                100                 105                 110

Glu Val Lys Phe Asn Trp Tyr Val Asp Gly Val Glu Val His Asn Ala
                115                 120                 125

Lys Thr Lys Pro Arg Glu Glu Gln Tyr Asn Ser Thr Tyr Arg Val Val
                130                 135                 140

Ser Val Leu Thr Val Leu His Gln Asp Trp Leu Asn Gly Lys Glu Tyr
145                 150                 155                 160

Lys Cys Lys Val Ser Asn Lys Ala Leu Pro Ala Pro Ile Glu Lys Thr
                165                 170                 175

Ile Ser Lys Ala Lys Gly Gln Pro Arg Glu Pro Gln Val Tyr Thr Leu
                180                 185                 190

Pro Pro Ser Arg Asp Glu Leu Thr Lys Asn Gln Val Ser Leu Thr Cys
                195                 200                 205

Leu Val Lys Gly Phe Tyr Pro Ser Asp Ile Ala Val Glu Trp Glu Ser
210                 215                 220

Asn Gly Gln Pro Glu Asn Asn Tyr Lys Thr Thr Pro Pro Val Leu Asp
225                 230                 235                 240

Ser Asp Gly Ser Phe Phe Leu Tyr Ser Lys Leu Thr Val Asp Lys Ser
                245                 250                 255

Arg Trp Gln Gln Gly Asn Val Phe Ser Cys Ser Val Met His Glu Ala
                260                 265                 270

Leu His Asn His Tyr Thr Gln Lys Ser Leu Ser Leu Ser Pro Gly Lys
                275                 280                 285
```

<210> SEQ ID NO 9
<211> LENGTH: 288
<212> TYPE: PRT
<213> ORGANISM: Artificial
<220> FEATURE:
<223> OTHER INFORMATION: Fusion protein

<400> SEQUENCE: 9

```
Met Gly Arg Ala Met Val Ala Arg Leu Gly Leu Gly Leu Leu Leu Leu
1               5                   10                  15

Ala Leu Leu Leu Pro Thr Gln Ile Tyr Ser Ser Glu Thr Thr Thr Gly
                20                  25                  30

Thr Ser Ser Asn Ser Ser Gln Ser Thr Ser Asn Ser Gly Leu Ala Pro
                35                  40                  45

Asn Pro Thr Asn Ala Thr Thr Lys Ala Pro Lys Ser Cys Asp Lys Thr
 50                  55                  60

His Thr Cys Pro Pro Cys Pro Ala Pro Glu Leu Leu Gly Gly Pro Ser
 65                  70                  75                  80

Val Phe Leu Phe Pro Pro Lys Pro Lys Asp Thr Leu Met Ile Ser Arg
```

```
                 85                  90                  95

Thr Pro Glu Val Thr Cys Val Val Asp Val Ser His Glu Asp Pro
                100                 105                 110

Glu Val Lys Phe Asn Trp Tyr Val Asp Gly Val Glu Val His Asn Ala
            115                 120                 125

Lys Thr Lys Pro Arg Glu Glu Gln Tyr Asn Ser Thr Tyr Arg Val Val
    130                 135                 140

Ser Val Leu Thr Val Leu His Gln Asp Trp Leu Asn Gly Lys Glu Tyr
145                 150                 155                 160

Lys Cys Lys Val Ser Asn Lys Ala Leu Pro Ala Pro Ile Glu Lys Thr
                165                 170                 175

Ile Ser Lys Ala Lys Gly Gln Pro Arg Glu Pro Gln Val Tyr Thr Leu
            180                 185                 190

Pro Pro Ser Arg Asp Glu Leu Thr Lys Asn Gln Val Ser Leu Thr Cys
    195                 200                 205

Leu Val Lys Gly Phe Tyr Pro Ser Asp Ile Ala Val Glu Trp Glu Ser
210                 215                 220

Asn Gly Gln Pro Glu Asn Asn Tyr Lys Thr Thr Pro Pro Val Leu Asp
225                 230                 235                 240

Ser Asp Gly Ser Phe Phe Leu Tyr Ser Lys Leu Thr Val Asp Lys Ser
                245                 250                 255

Arg Trp Gln Gln Gly Asn Val Phe Ser Cys Ser Val Met His Glu Ala
            260                 265                 270

Leu His Asn His Tyr Thr Gln Lys Ser Leu Ser Leu Ser Pro Gly Lys
    275                 280                 285

<210> SEQ ID NO 10
<211> LENGTH: 29
<212> TYPE: PRT
<213> ORGANISM: Macaca fascicularis

<400> SEQUENCE: 10

Thr Val Thr Thr Ser Ala Pro Leu Ser Ser Asn Ser Pro Gln Asn Thr
1               5                   10                  15

Ser Thr Thr Pro Asn Pro Ala Asn Thr Thr Lys Ala
            20                  25

<210> SEQ ID NO 11
<211> LENGTH: 262
<212> TYPE: PRT
<213> ORGANISM: Artificial
<220> FEATURE:
<223> OTHER INFORMATION: Fusion protein

<400> SEQUENCE: 11

Ser Glu Thr Thr Thr Gly Thr Ser Ser Asn Ser Ser Gln Ser Thr Ser
1               5                   10                  15

Asn Ser Gly Leu Ala Pro Asn Pro Thr Asn Ala Thr Thr Lys Val Pro
            20                  25                  30

Lys Ser Cys Asp Lys Thr His Thr Cys Pro Pro Cys Pro Ala Pro Glu
        35                  40                  45

Leu Leu Gly Gly Pro Ser Val Phe Leu Phe Pro Pro Lys Pro Lys Asp
    50                  55                  60

Thr Leu Met Ile Ser Arg Thr Pro Glu Val Thr Cys Val Val Val Asp
65                  70                  75                  80

Val Ser His Glu Asp Pro Glu Val Lys Phe Asn Trp Tyr Val Asp Gly
                85                  90                  95
```

Val Glu Val His Asn Ala Lys Thr Lys Pro Arg Glu Gln Tyr Asn
            100                 105                 110

Ser Thr Tyr Arg Val Val Ser Val Leu Thr Val Leu His Gln Asp Trp
        115                 120                 125

Leu Asn Gly Lys Glu Tyr Lys Cys Lys Val Ser Asn Lys Ala Leu Pro
    130                 135                 140

Ala Pro Ile Glu Lys Thr Ile Ser Lys Ala Lys Gly Gln Pro Arg Glu
145                 150                 155                 160

Pro Gln Val Tyr Thr Leu Pro Pro Ser Arg Asp Glu Leu Thr Lys Asn
                165                 170                 175

Gln Val Ser Leu Thr Cys Leu Val Lys Gly Phe Tyr Pro Ser Asp Ile
            180                 185                 190

Ala Val Glu Trp Glu Ser Asn Gly Gln Pro Glu Asn Asn Tyr Lys Thr
        195                 200                 205

Thr Pro Pro Val Leu Asp Ser Asp Gly Ser Phe Phe Leu Tyr Ser Lys
    210                 215                 220

Leu Thr Val Asp Lys Ser Arg Trp Gln Gln Gly Asn Val Phe Ser Cys
225                 230                 235                 240

Ser Val Met His Glu Ala Leu His Asn His Tyr Thr Gln Lys Ser Leu
                245                 250                 255

Ser Leu Ser Pro Gly Lys
            260

<210> SEQ ID NO 12
<211> LENGTH: 262
<212> TYPE: PRT
<213> ORGANISM: Artificial
<220> FEATURE:
<223> OTHER INFORMATION: Fusion protein

<400> SEQUENCE: 12

Ser Glu Thr Thr Thr Gly Thr Ser Ser Asn Ser Ser Gln Ser Thr Ser
1               5                   10                  15

Asn Ser Gly Leu Ala Pro Asn Pro Thr Asn Ala Thr Thr Lys Ala Pro
            20                  25                  30

Lys Ser Cys Asp Lys Thr His Thr Cys Pro Pro Cys Pro Ala Pro Glu
        35                  40                  45

Leu Leu Gly Gly Pro Ser Val Phe Leu Phe Pro Pro Lys Pro Lys Asp
    50                  55                  60

Thr Leu Met Ile Ser Arg Thr Pro Glu Val Thr Cys Val Val Val Asp
65                  70                  75                  80

Val Ser His Glu Asp Pro Glu Val Lys Phe Asn Trp Tyr Val Asp Gly
                85                  90                  95

Val Glu Val His Asn Ala Lys Thr Lys Pro Arg Glu Gln Tyr Asn
            100                 105                 110

Ser Thr Tyr Arg Val Val Ser Val Leu Thr Val Leu His Gln Asp Trp
        115                 120                 125

Leu Asn Gly Lys Glu Tyr Lys Cys Lys Val Ser Asn Lys Ala Leu Pro
    130                 135                 140

Ala Pro Ile Glu Lys Thr Ile Ser Lys Ala Lys Gly Gln Pro Arg Glu
145                 150                 155                 160

Pro Gln Val Tyr Thr Leu Pro Pro Ser Arg Asp Glu Leu Thr Lys Asn
                165                 170                 175

Gln Val Ser Leu Thr Cys Leu Val Lys Gly Phe Tyr Pro Ser Asp Ile
            180                 185                 190

```
Ala Val Glu Trp Glu Ser Asn Gly Gln Pro Glu Asn Asn Tyr Lys Thr
        195                 200                 205

Thr Pro Pro Val Leu Asp Ser Asp Gly Ser Phe Phe Leu Tyr Ser Lys
        210                 215                 220

Leu Thr Val Asp Lys Ser Arg Trp Gln Gln Gly Asn Val Phe Ser Cys
225                 230                 235                 240

Ser Val Met His Glu Ala Leu His Asn His Tyr Thr Gln Lys Ser Leu
                245                 250                 255

Ser Leu Ser Pro Gly Lys
            260
```

METHODS OF USE OF SOLUBLE CD24 FOR TREATING LUPUS NEPHRITIS

FIELD OF THE INVENTION

The present invention relates to compositions and methods for treating systemic lupus erythematosus (SLE) and related manifestations.

BACKGROUND OF THE INVENTION

Systemic lupus erythematous (lupus, SLE) is the most common autoimmune disease and has an extremely strong gender bias towards women. SLE is a chronic, inflammatory, connective tissue disease that can affect the joints and many organs, including the skin, heart, lungs, kidneys, and nervous system. It is a complex disease with variable clinical manifestations; however, not everyone with systemic lupus erythematosus has all of the symptoms. Typically, lupus is characterized by periods of illness, called flares, and periods of wellness, or remission. It is difficult to estimate how many people have the disease, because its symptoms vary widely and its onset is often hard to pinpoint. Although SLE usually first affects people between the ages of 15 and 45 years, it can occur in childhood or later in life as well. Many more women than men have lupus. Lupus is more common in African American women than in Caucasian women and is also more common in women of Hispanic, Asian, and Native American descent. African American and Hispanic women are also more likely to have active disease and serious organ system involvement. In addition, lupus can run in families, but the risk that a child or a brother or sister of a patient will also have lupus is still quite low. SLE patients display a 4.6 fold increased mortality compared with age-matched population, decreased work productivity, mood disorders and deteriorated organ function. However, compared with other autoimmune and allergic diseases, progress in the development of drugs for the treatment of SLE has been slow and there is an urgent and unmet medical need to identify new therapeutic targets.

SUMMARY OF THE INVENTION

Provided herein is a method of treating SLE and its associated symptoms, indications, complications and manifestations by administering a CD24 protein to a subject in need thereof. SLE is frequently associated with, and exacerbated by tissue damage, either resulting from the disease itself or as a result of corticosteroids used to control the inflammatory effects during treatment.

The inventors have demonstrated that CD24 negatively regulates host response to cellular DAMPs that are released as a result of tissue or organ damage, and at least two overlapping mechanisms may explain this activity. First, CD24 binds to several DAMPs, including HSP70, HSP90, HMGB1 and nucleolin and represses host response to these DAMPs. To do this, it is presumed that CD24 may trap the inflammatory stimuli to prevent interaction with their receptors, TLR or RAGE. Second, using an acetaminophen-induced mouse model of liver necrosis and ensuring inflammation, the inventors demonstrated that through interaction with its receptor, Siglec G, CD24 provides a powerful negative regulation for host response to tissue injuries. To achieve this activity, CD24 may bind and stimulate signaling by Siglec G wherein Siglec G-associated SHP1 triggers the negative regulation. Both mechanisms may act in concert as mice with targeted mutation of either gene mounted much stronger inflammatory response. In fact, DC cultured from bone marrow from either CD24−/− or Siglec G−/− mice produced higher levels of inflammatory cytokines when stimulated with either HMGB1, HSP70, or HSP90. To our knowledge, CD24 is the only inhibitory DAMP receptor capable of shutting down inflammation triggered by DAMPs and no drug is currently available that specifically targets host inflammatory response to tissue injuries.

The inventors have demonstrated the ability of exogenous soluble CD24 protein to alleviate DAMP-mediated autoimmune disease using mouse models of RA, MS and GvHD. Given the importance of DAMPs in SLE pathogenesis, CD24 protein can be used in the treatment or prevention (prophylaxis) of SLE or its related manifestations such as lupus nephritis, neuropsychiatric, hematologic, musculoskeletal, and severe cutaneous lupus. The inventors have also discovered that CD24 protein can be used to alleviate symptoms of SLE such as proteinuria, splenomegaly and lymphadenopathy. Typically, lupus follows an unpredictable relapsing remitting course characterized by periods of illness, called flares, and periods of wellness, or remission. Therefore, the CD24 proteins described herein may be administered therapeutically (i.e. during a flare), or prophylactically (i.e. during a remission period) in order to control or prevent the duration, severity and/or frequency of disease flares. The CD24 proteins described herein can also be used in combination with corticosteroids in order to reduce the frequency and dose of corticosteroids administered.

The inventors have further demonstrated that CD24 can modulate molecules involved in fat and lipid metabolism. In particular, they have demonstrated that CD24 can reduce the levels of circulating serum LDL-C and increase circulating leptin. Dyslipidemia is prevalent in patients with SLE (up to 63%; Kakati et al 2003). In addition, the incidence of atherosclerotic cardiovascular disease (CVD) is increased up to 50-fold in SLE patients compared to age- and gender-matched control subjects and this can only partly be explained by traditional risk factors for CVD (27). Accordingly, CD24 proteins described herein can be particularly useful in the treatment of SLE patients with lipidemia and/or cardiovascular disease, or in the prevention of such complications in patients with SLE.

Human CD24 is a small GPI-anchored molecule encoded by an open-reading frame of 240 base pairs in the CD24 gene (28). Of the 80 amino acids, the first 26 constitute the signal peptide, while the last 23 serve as a signal for cleavage to allow for the attachment of the GPI tail. As a result, the mature human CD24 molecule has only 31 amino acids. One of the 31 amino acids is polymorphic among the human population. A C to T transition at nucleotide 170 of the open-reading frame results in the substitution of Alanine (a) with Valine (v). Since this residue is in the immediate N-terminal to the cleavage site, and since the replacement is nonconservative, these two alleles may be expressed at different efficiencies on the cell surface. Indeed, transfection studies with cDNA demonstrated that the CD24$^v$ allele is more efficiently expressed on the cell surface (28). Consistent with this, CD24$^{v/v}$ PBL expressed higher levels of CD24, especially on T cells.

The CD24 protein may comprise a mature human CD24 or a variant thereof. The sequence of the mature human CD24 may comprise the sequence of SEQ ID NO: 1 or 2. The CD24 protein may comprise any or all of the extracellular domain of human CD24. The sequence of the CD24 protein may comprise the signal sequence of SEQ ID NO: 4, which may facilitate secretion from a cell expressing the protein. The signal peptide sequence may be one that is found on other transmembrane or secreted proteins, or one modified from the existing signal peptides known in the art. The CD24 protein may be soluble and/or may be glycosylated. The CD24 protein may be produced using a eukaryotic protein expression system, which may comprise a vector contained in a Chinese Hamster Ovary cell line or a replication-defective retroviral vector. The replication defective retroviral vector may be stably integrated into the genome of a eukaryotic cell.

The CD24 protein may comprise a protein tag, which may be fused at the N- or C-terminus of the CD24 protein. The protein may comprise a portion of a mammalian immunoglobulin (Ig), which may be the Fc region of a human Ig protein. The human Ig protein may comprise the hinge region and CH2 and CH3 domains of the human Ig protein, and the human Ig protein may be IgG1, IgG2, IgG3, IgG4, or IgA. The Fc region may also comprise the hinge region and CH2, CH3, and CH4 domains of IgM. The sequence of the CD24 protein may comprise the sequence of SEQ ID NO: 5, 6, 8, 9, 11, or 12.

BRIEF DESCRIPTION OF THE DRAWINGS

FIG. 1A shows the amino acid composition of the full length CD24 fusion protein, CD24Fc (also referred to herein as CD24Ig) (SEQ ID NO: 5). The underlined 26 amino acids are the signal peptide of CD24 (SEQ ID NO: 4), which are cleaved off during secretion from a cell expressing the protein and thus missing from the processed version of the protein (SEQ ID NO: 6). The bold portion of the sequence is the extracellular domain of the mature CD24 protein used in the fusion protein (SEQ ID NO: 2). The last amino acid (A or V) that is ordinarily present in the mature CD24 protein has been deleted from the construct to avoid immunogenicity. The non-underlined, non-bold letters are the sequence of IgG1 Fc, including the hinge region and CH1 and CH2 domains (SEQ ID NO: 7). FIG. 1B shows the sequence of CD24$^V$Fc (SEQ ID NO: 8), in which the mature human CD24 protein (bold) is the valine polymorphic variant of SEQ ID NO: 1. FIG. 1C shows the sequence of CD24$^A$Fc (SEQ ID NO: 9), in which the mature human CD24 protein (bold) is the alanine polymorphic variant of SEQ ID NO: 1. The various parts of the fusion protein in FIGS. 1B and 1C are marked as in FIG. 1A and the variant valine/alanine amino acid is double underlined.

FIG. 2 shows amino acid sequence variations between mature CD24 proteins from mouse (SEQ ID NO: 3) and human (SEQ ID NO: 2). The potential O-glycosylation sites are bolded, and the N-glycosylation sites are underlined.

FIG. 3A. i.v. injection of 1 mg CD24IgG1. FIG. 3B. s.c. injection of 1 mg CD24IgG1 (CD24Fc). FIG. 3C. Comparison of the total amounts of antibody in the blood as measured by areas under curve (AUC), half-life and maximal blood concentration. Note that overall, the AUC and Cmax of the s.c. injection is about 80% of i.v. injection, although the difference is not statistically significant.

FIG. 4A. Host response to PAMP was unaffected by CD24-Siglec G(10) interaction. FIG. 4B. CD24-Siglec G (10) interaction represses host response to DAMP, possibly through the Siglec G/10-associated SHP-1.

FIG. 5A. Diagram of experiments. BALB/c mice (8 weeks old) received mAbs on day 1 in conjunction with either vehicle or fusion proteins. The mice were injected LPS on day 3, and were observed daily for 3 weeks. FIG. 5B. CD24Fc reduces clinical scores of CAIA. The fusion proteins (1 mg/mouse) or vehicles were injected once on day 1. Clinical scores were determined double blind. *, P<0.05; , P<0.01; *, P<0.001. The effect of CD24 was reproduced in 6 independent experiments, involving a total of 52 mice in the PBS group and 54 mice in CD24Fc group.

FIG. 6A. Representative FACS profile. FIG. 6B. The summary of reduced cytokines (Mean±SE) measured in the joint homogenates.

FIG. 9A. Diagram of experiments. FIG. 9B. Clinical scores of arthritis, scored double blind.

FIG. 11A. Diagram of the fusion proteins. The polymorphic residue in extracellular domain was deleted in CD24Fc. FIG. 11B. SDS-PAGE analysis for the purity of the two fusion proteins. The numbers shown are μg of proteins loaded. FIG. 11C. Comparison between CD24'Fc and CD24Fc for their binding to Siglec10Fc. Desialylated CD24Fc was used as a negative control. FIG. 11D. Comparison between CD24Fc and CD24$^V$Fc for the therapeutic effect in the CAIA model. CD24Fc or CD24$^V$Fc (200 μg/mouse) was injected into mice in conjunction with a cocktail of anti-collagen antibodies on day 1. Arthritis was elicited by treatment with LPS on day 3. The diseases were scored double blind. Data shown in FIGS. 11C and D are means and SEM. FIGS. 11E and 11F also compare the therapeutic effects of CD24Fc and CD24$^V$Fc, in experiments performed similarly to the ones shown in FIG. 11D, except that IgG1 Fc was used as a negative control. As shown in FIG. 11E, CD24Fc reduced the RA score as early as day 4, and showed statistically significant protection throughout the three weeks of observation. On the other hand, as shown in FIG. 11F, CD24$^V$Fc showed a reduction in RA score starting on day 8. Although reduced scores were observed thereafter, the reduction did not reach statistical significance.

FIG. 12A. CD24Fc suppressed development of arthritis in the CIA model. Mice received a single treatment (1 mg/mouse) on day 17 when no clinical symptoms had developed. Data shown are disease scores among the mice that had developed arthritis with disease scores from 3 to 8. The difference between CD24Fc and PBS group was significant (P=0.02, Fisher's PLSD test). N=9 for vehicle and N=7 for CD24Fc group. FIG. 12B. Therapeutic effect of CD24Fc in CIA of DBA/1 mice. The mice with clinical symptoms of scores from 3 to 8 were randomized to receive either 200 μg CD24Fc or an equal volume of control vehicle (PBS) by i.p. injection, every the other day, five times. The mice were inspected daily to score for the clinical symptoms for two weeks. CD24Fc significantly lessened the clinical symptoms of arthritis when arthritis developed (P=0.02, Fisher's PLSD test). N=6 for PBS and N=5 for CD24Fc groups.

FIG. 13A. On day 28, mice with a clinical score >3 were randomized to receive either vehicle or CD24Fc (1 mg/mouse). The endpoint was a reduction of score by 50% (top) or 80% (bottom). N=12 for PBS, and N=11 for CD24Fc. FIG. 13B. Dose-dependent therapeutic effect of CD24Fc in chicken CIA model. Details as in FIG. 13A, except that the treatments started at the peak of disease (average score of 5.5 in both groups on day 33). Mice with a clinical score >3 were randomized to receive 5 injections of either vehicle or CD24Fc. The endpoint was a reduction of score by either 50% (top) or 80% (bottom). N=11. The difference between the 100 μg experimental and the vehicle control groups was statistically significant.

FIG. 14A. ShRNA silencing of CD24 led to spontaneous production of TNFα, IL-6 and IL-1β. THP1 cells were transduced with lentiviral vectors encoding either scrambled or two independent CD24 shRNA. The transduced cells were differentiated into macrophages by culturing for 4 days with PMA (15 ng/ml). After washing away PMA and nonadherent cells, the cells were cultured for another 24 hours for measurement of inflammatory cytokines by cytokine beads array. FIG. 14B. As in FIG. 14A, except that the given concentration of CD24Fc or control IgG Fc was added to macrophages in the last 24 hours. FIG. 14C. CD24Fc was more efficient than CD24'Fc in suppressing the spontaneous production of inflammatory cytokines by CD24-silenced macrophage cell line THP1. The data shown are as detailed in the FIG. 11 legends, except that the CD24Fc and CD24'Fc are compared side-by-side.

FIG. 15A. CD24Fc stimulated tyrosine phosphorylation of, and SHP-1 binding to, Siglec G. Spleen cells from CD24-deficient mice were stimulated with either vehicle, Fc control or CD24Fc (1 μg/ml) for 30 min. After lysis, the Siglec G protein was precipitated with anti-Siglec G antisera. Siglec G phosphorylation and its association to SHP-1 were detected by Western blot. FIG. 15B. Siglecg was essential for therapeutic effect of CD24Fc in mice with low dose of anti-collagen antibodies. WT (FIG. 15A) and Siglece$^{-/-}$ mice (FIG. 15B) received either vehicle control or CD24Fc in conjunction of a cocktail of anti-collagen mAbs (2 mg/mouse). LPS was injected on day 3 (100 μg/mouse). The clinical scores were recorded daily double blind. Data are representative of two experiments. FIG. 15C. Targeted mutation of Siglecg attenuated but did not abrogate the therapeutic effect of CD24Fc with double doses of anti-collagen antibodies. The anti-collagen antibodies (4 mg/mouse) and CD24Fc (1 mg/mouse) were added on day 1, while LPS (100 μg/mouse) was added on day 3. Male WT (FIG. 15A) and Siglece$^{-/-}$ mice (FIG. 15B) were observed daily for clinical score. % inhibitions were calculated by % reduction of accumulated RA score. N=5. Male mice were used at 8 weeks of age.

DETAILED DESCRIPTION

Figure 3:
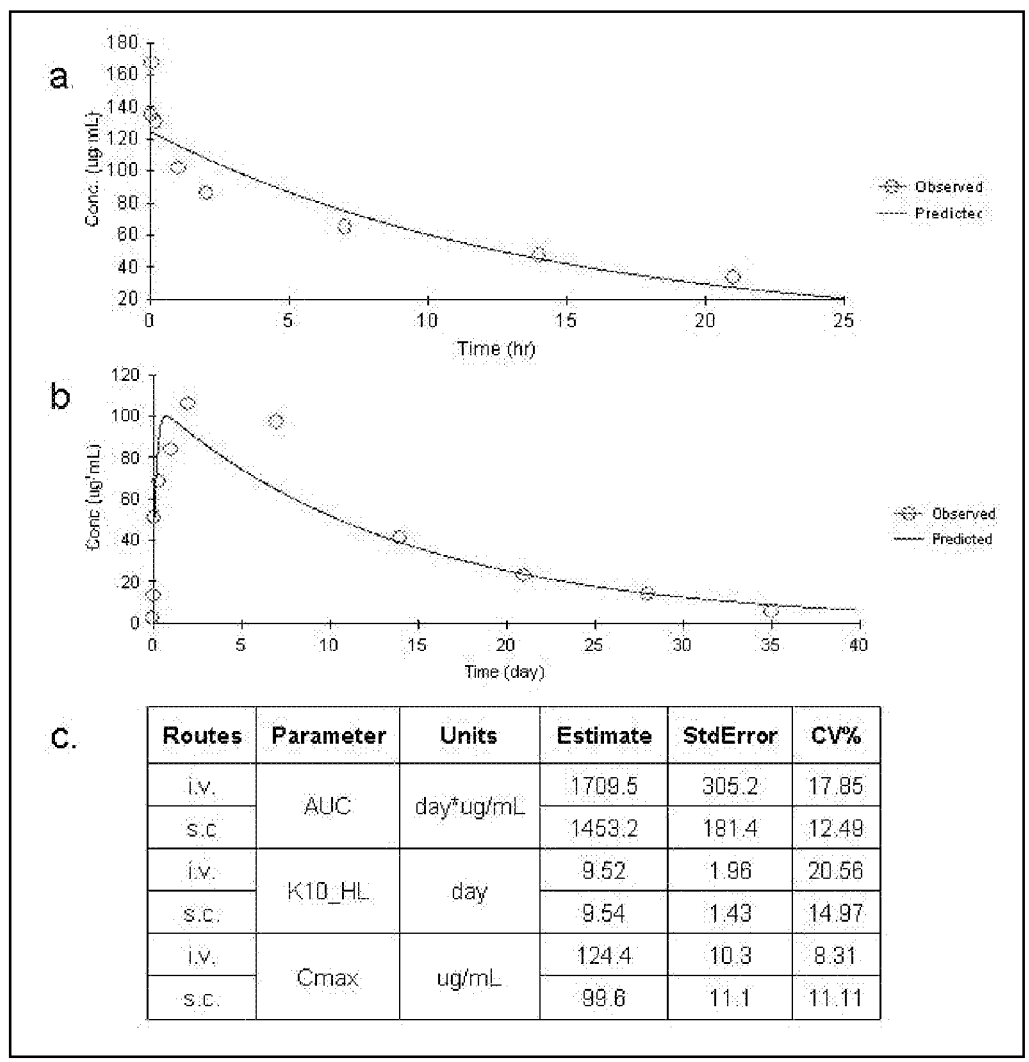
FIG. 3. WinNonlin compartmental modeling analysis of pharmacokenitics of CD24IgG1 (CD24Fc). The opened circles represent the average of 3 mice, and the line is the predicted pharmacokinetic curve.

The inventors have discovered that, surprisingly, a soluble form of CD24 is highly effective for treating SLE. The effect may be mediated through damage-associated molecular patterns. Pattern recognition is involved in inflammatory response triggered by both pathogen-associated and tissue damage-associated molecular patterns, respectively called PAMPs and DAMPs. The inventors have realized that recent studies have demonstrated that an exacerbated host response to DAMPs may play a part in the pathogenesis of autoimmune disease. First, failure to clear debris from necrotic cells has long been suggested as a cause of autoimmune diseases in humans, particularly SLE (1). Consistent with defective clearance, higher levels of nucleosomes have been found in the plasma of SLE patients and SLE-prone mice (2). Through its associated HMGB1, these nucleosomes trigger release of inflammatory cytokines via TLR2/4 (2). Second, in support of the role of Hmgb1 in SLE, Wen et al. reported that autoantibody production against DNA-containing immune complex requires HMGB1 in the complex to interact with TLR2 (3). DAMPs were found to promote the production of inflammatory cytokines and autoimmune diseases and in animal models, and inhibitors of DAMPs such as HMGB1 and HSP90 were consequently found to ameliorate rheumatoid arthritis (RA) (4-6). TLRs, RAGE-R, DNGR (encoded by Clec9A), and Mincle have been shown to be receptors responsible for mediating inflammation initiated by a variety of DAMPs (2, 7-14).

The inventors' recent work demonstrated that CD24-Siglec G interactions discriminate innate immunity to DAMPs from PAMPs (15, 16). Siglec proteins are membrane-associated immunoglobulin (Ig) superfamily members that recognize a variety of sialic acid-containing structures. Most Siglecs have an intra-cellular immune-tyrosine inhibitory motif (ITIM) that associates with SHP-1, -2 and Cbl-b to control key regulators of inflammatory responses. The inventors identified CD24 as the first natural ligand for a Siglec, Siglec G in mouse and Siglec 10 in human (15). Siglec G interacts with sialylated CD24 to suppress the TLR-mediated host response to DAMPs, such as HMGB1, via a SHP-1/2 signaling mechanism (15), which is critical for SLE pathogenesis (2). More recently, experiments by the inventors have demonstrated that Siglec G associates with Cbl to trigger degradation of RIG-I, resulting in the suppression of the type I interferon response (17), a key factor in human lupus pathogenesis.

Genetic analysis of a variety of autoimmune disease in human, including multiple sclerosis (18-21), SLE (20, 22), rheumatoid arthritis (23), and giant cell arthritis (24), have shown a significant association between CD24 polymorphism and risk of autoimmune diseases. In particular, a recent meta-analysis involving 7507 patients and 8803 controls confirmed the association between CD24 polymorphism and risk of multiple autoimmune diseases, including SLE (25). Specifically, a di-nucleotide deletion at position 1527 (P1527) of CD24 mRNA is associated with significantly reduced risk (odds ratio OR=0.53 with 95% bootstrap confidence interval=0.34-0.81) and delayed progression (p=0.016) of MS. More importantly, using 150 families from two independent cohorts, it has been found that the P1527del allele was preferentially transmitted to unaffected individuals (p=0.003). In heterozygous individuals, the mRNA levels for the di-nucleotide-deletion allele was 2.5-fold less than that of the wild-type allele (p=0.004). Transfection studies performed by the inventors revealed that the di-nucleotide deletion dramatically reduced the stability of CD24 mRNA (p<0.001). The results demonstrated that a destabilizing di-nucleotide deletion in the 3'UTR of CD24 mRNA substantially reduced the risk and delayed the progression of MS. The inventors have also found that the P1527del1 allele is also strongly associated with reduced risk for SLE. To their knowledge, this is the first example of a genetic polymorphism that confers protection against both organ-specific and systemic autoimmune diseases and the first 3' UTR mRNA-destabilizing SNP that confers protection against any autoimmune disease (20). Furthermore, the causation between Siglecs and SLE pathogenesis is supported by a recent report showing that targeted mutation of Siglecg in MRL/lpr mice modestly exacerbated spontaneous lupus (26). The role for Siglecs in SLE is supported by genetic studies in human and mouse.

1. Definitions

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

A "peptide" or "polypeptide" is a linked sequence of amino acids and may be natural, synthetic, or a modification or combination of natural and synthetic.

"Substantially identical" may mean that a first and second amino acid sequence are at least 60%, 65%, 70%, 75%, 80%, 85%, 90%, 95%, 96%, 97%, 98%,or 99% over a region of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, or 300 amino acids.

"Treatment" or "treating," when referring to protection of an animal from a disease, means preventing, suppressing, repressing, or completely eliminating the disease. Preventing the disease involves administering a composition of the present invention to an animal prior to onset of the disease. Suppressing the disease involves administering a composition of the present invention to an animal after induction of the disease but before its clinical appearance. Repressing the disease involves administering a composition of the present invention to an animal after clinical appearance of the disease.

A "variant" may mean a peptide or polypeptide that differs in amino acid sequence by the insertion, deletion, or conservative substitution of amino acids, but retain at least one biological activity. Representative examples of "biological activity" include the ability to bind to a toll-like receptor and to be bound by a specific antibody. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

2. CD24

Provided herein is a CD24 protein, which may comprise the amino acid sequence of mature human CD24 or those from other mammals, which corresponds to the extracellular domain (ECD) of CD24, or a variant thereof. As described above, the sequence of the mature human CD24 protein is 31 amino acids long with a variable alanine (A) with valine (V) residue at its C-terminal end:

SETTTGTSSNSSQSTSNSGLAPNPTNATTK(V/A) (SEQ ID NO: 1)

The C-terminal valine or alanine may be immunogenic and may be omitted from the CD24 protein to reduce its immunogenicity. Therefore, the CD24 protein may comprise the amino acid sequence or mature human CD24 lacking the C-terminal amino acid:

SETTTGTSSNSSQSTSNSGLAPNPTNATTK (SEQ ID NO: 2)

Despite considerable sequence variations in the amino acid sequence of the mature CD24 proteins from mouse and human, they are functionally equivalent, as human CD24Fc has been shown to be active in the mouse. The amino acid sequence of the human CD24 ECD shows some sequence conservation with the mouse protein (39% identity; Genbank accession number NP_033976). However, it is not that surprising that the percent identity is not higher as the CD24 ECD is only 27-31 amino acids in length, depending on the species, and binding to some of its receptor(s), such as Siglec 10/G, is mediated by its sialic acid and/or galactose sugars of the glycoprotein. The amino acid sequence identity between the extracellular domains of the human Siglec-10 (GenBank accession number AF310233) and its murine homolog Siglec-G (GenBank accession number NP_766488) receptor proteins is 63% (FIG. 2). As a result of sequence conservation between mouse and human CD24 primarily in the C-terminus and in the abundance of glycosylation sites, significant variations in the mature CD24 proteins may be tolerated in using the CD24 protein, especially if those variations do not affect the conserved residues in the C-terminus or do not affect the glycosylation sites from either mouse or human CD24. Therefore, the CD24 protein may comprise the amino acid sequence of mature murine CD24:

NQTSVAPFPGNQNISASPNPTNATTRG (SEQ ID NO: 3).

The amino acid sequence of the human CD24 ECD shows more sequence conservation with the cynomolgus monkey protein (52% identity; UniProt accession number UniProtKB-I7GKK1) than with mouse. Again, this is not surprising given that the percent identity is not higher as the ECD is only 29-31 amino acids in length in these species, and the role of sugar residues in binding to its receptor(s). The amino acid sequence of cynomolgous Siglec-10 receptor has not been determined but the amino acid sequence identity between the human and rhesus monkey Siglec-10 (GenBank accession number XP_001116352) proteins is 89%. Therefore, the CD24 protein may also comprise the amino acid sequence of mature cynomolgous (or rhesus) monkey CD24:

TVTTSAPLSSNSPQNTSTTPNPANTTTKA (SEQ ID NO: 10)

The CD24 protein may be soluble. The CD24 protein may further comprise an N-terminal signal peptide, to allow secretion from a cell expressing the protein. The signal peptide sequence may comprise the amino acid sequence MGRAMVARLGLGLLLLALLLPTQIYS (SEQ ID NO: 4). Alternatively, the signal sequence may be any of those that are found on other transmembrane or secreted proteins, or those modified from the existing signal peptides known in the art.

a. Fusion

The CD24 protein may be fused at its N- or C-terminal end to a protein tag, which may comprise a portion of a mammalian Ig protein, which may be human or mouse or another species. The portion may comprise an Fc region of the Ig protein. The Fc region may comprise at least one of the hinge region, CH2, CH3, and CH4 domains of the Ig protein. The Ig protein may be human IgG1, IgG2, IgG3, IgG4, or IgA, and the Fc region may comprise the hinge region, and CH2 and CH3 domains of the Ig protein. The Fc region may comprise a human immunoglobulin G1 (IgG1) isotype, which may comprise the sequence of SEQ ID NO: 7. The Ig protein may also be IgM, and the Fc region may comprise the hinge region and CH2, CH3, and CH4 domains of IgM. The protein tag may be an affinity tag that aids in the purification of the protein, and/or a solubility-enhancing tag that enhances the solubility and recovery of functional proteins. The protein tag may also increase the valency of the CD24 protein. The protein tag may also comprise GST, His, FLAG, Myc, MBP, NusA, thioredoxin (TRX), small ubiquitin-like modifier (SUMO), ubiquitin (Ub), albumin, or a Camelid Ig. Methods for making fusion proteins and purifying fusion proteins are well known in the art.

Based on preclinical research, for the construction of the fusion protein CD24Fc identified in the examples, the truncated form of native CD24 molecule of 30 amino acids, which lacks the final polymorphic amino acid before the GPI signal cleavage site (that is, a mature CD24 protein having SEQ ID NO: 2), has been used. The mature human CD24 sequence is fused to a human IgG1 Fc domain (SEQ ID NO: 7). The full length CD24Fc fusion protein is provided in SEQ ID NO: 5 (FIG. 1), and the processed version of CD24Fc fusion protein that is secreted from the cell (i.e. lacking the signal sequence which is cleaved off) is provided in SEQ ID NO: 6. Processed polymorphic variants of mature CD24 (that is, mature CD24 protein having SEQ ID NO: 1) fused to IgG1 Fc may comprise SEQ ID NO: 11 or 12.

b. Production

The CD24 protein may be heavily glycosylated, and may be involved in functions of CD24 such as costimulation of immune cells and interaction with a damage-associated molecular pattern molecule (DAMP). The CD24 protein may be prepared using a eukaryotic expression system. The expression system may entail expression from a vector in mammalian cells, such as Chinese Hamster Ovary (CHO) cells. The system may also be a viral vector, such as a replication-defective retroviral vector that may be used to infect eukaryotic cells. The CD24 protein may also be produced from a stable cell line that expresses the CD24 protein from a vector or a portion of a vector that has been integrated into the cellular genome. The stable cell line may express the CD24 protein from an integrated replication-defective retroviral vector. The expression system may be GPEx™ (cell line development technology).

c. Pharmaceutical Composition

The CD24 protein may be contained in a pharmaceutical composition, which may comprise a pharmaceutically acceptable amount of the CD24 protein. The pharmaceutical composition may comprise a pharmaceutically acceptable carrier. The pharmaceutical composition may comprise a solvent, which may keep the CD24 protein stable over an extended period. The solvent may be PBS, which may keep the CD24 protein stable for at least 66 months at −20° C. (−15~−25° C.). The solvent may be capable of accommodating the CD24 protein in combination with another drug.

The pharmaceutical composition may be formulated for parenteral administration including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

The pharmaceutical composition may also be formulated as a depot preparation, which may be administered by implantation or by intramuscular injection. The composition may be formulated with suitable polymeric or hydrophobic materials (as an emulsion in an acceptable oil, for example), ion exchange resins, or as sparingly soluble derivatives (as a sparingly soluble salt, for example). A formulation for subcutaneous injection may be particularly relevant for an indication like lupus and its associated manifestations and complications.

d. Dosage

The dose of the CD24 protein may ultimately be determined through a clinical trial to determine a dose with acceptable toxicity and clinical efficacy. The initial clinical dose may be estimated through pharmacokinetics and toxicity studies in rodents and non-human primates. The dose of the CD24 protein may be 0.01 mg/kg to 1000 mg/kg, and may be 1 to 500 mg/kg, depending on the desired amount treatment effect and the route of administration. The CD24 protein may be administered by intravenous infusion or subcutaneous or intramural [that is, within the wall of a cavity or organ] injection, and the dose may be 10-1000 mg, 10-500 mg, 10-240 mg, 10-120 mg, or 10, 30, 60, 120, or 240 mg, where the subject is a human.

3. Methods of Treatment

The CD24 protein herein may be administered to a subject with Systemic Lupus Erythematosus (Lupus, SLE), to treat SLE or one or more symptoms, complications or manifestations thereof. SLE is a chronic, inflammatory, connective tissue disease that can affect the joints and many organs, including the skin, heart, lungs, kidneys, and nervous system. It is a complex autoimmune disease and can cause many different symptoms; however, not everyone with SLE has all of the symptoms. Renal involvement is common in SLE and acute or chronic renal impairment may develop with lupus nephritis, leading to acute or end-stage kidney failure. Lupus nephritis is a type of glomerulonephritis in which the glomeruli become inflamed, and is one of the most frequent and serious complications in patients with SLE. Other manifestations include neuropsychiatric, encephalopathy, hematologic, musculoskeletal, and severe cutaneous lupus. The CD24 protein may also be used to treat at least one of proteinuria, splenomegaly and lymphadenopathy associated with SLE. The subject may be a human, cat, dog, large animal, or avian.

One of the major determinants of poor long term prognosis is organ damage, which is predictive of more damage and death. Damage is in turn triggered by uncontrolled disease activity and especially by the long-standing corticosteroid use that is usually prescribed to SLE patients during their disease course to rapidly suppress inflammation. Because they are potent drugs, the doctor will seek the lowest dose of corticosteroids required to achieve the desired benefit. In an effort to minimize side effects associated with corticosteroids, researchers are working to develop ways to limit or offset the use of corticosteroids. The inventors have demonstrated the ability of exogenous soluble CD24 protein to alleviate DAMP-mediated autoimmune disease resulting from tissue damage using mouse models of RA, MS and GvHD. Given the importance of DAMPs in SLE pathogenesis, the CD24 protein may be used to reduce the organ damage associated with SLE to minimize disease progression and flares. Furthermore, the CD24 protein may be administered intermittently with corticosteroids to lower the doses of corticosteroids needed to control disease or provide a therapeutic holiday from corticosteroids.

The primary complication of lupus nephritis is permanent renal damage. This damage may be severe enough that it leads to renal failure and dependence on dialysis. All of the complications associated with renal failure apply to these patients, such as hypertension, fluid overload, premature vascular calcifications, hyperlipidemia, and premature coronary artery disease. About 63% of SLE patients have lipidemia and the incidence of atherosclerotic cardiovascular disease (CVD) is increased up to 50-fold in SLE patients compared to age- and gender-matched control subjects and this can only partly be explained by traditional risk factors for CVD. The inventors have demonstrated that CD24 can modulate molecules involved in fat and lipid metabolism. In particular, they have demonstrated that CD24 can reduce the levels of circulating serum LDL-C and increase circulating leptin. Accordingly, CD24 proteins described herein can be particularly useful in the treatment of SLE patients with lipidemia and/or cardiovascular disease, or in the prevention of such complications in patients with SLE, particularly patients with lupus nephritis. The patient may have a lysosomal acid lipase (LAL) deficiency, familial hypercholesterolemia, or hyperlipidemia. The subject may also be in need of treatment or prevention of atherosclerosis, or of lowering the risk of a cardiovascular disease event, which may be an atherosclerotic cardiovascular disease (ASCVD) event. The ASCVD event may be an acute coronary syndrome, myocardial infarction, stable or unstable angina, a coronary or other arterial revascularization, stroke, transient ischemic attack, or peripheral arterial disease presumed to be of atherosclerotic origin. Furthermore, the biological activity of the CD24 proteins in vivo can be detected by monitoring the serum levels of LDL-C and/or triglycerides in SLE patients, thus providing a convenient biomarker for clinical use.

Typically, lupus follows an unpredictable relapsing remitting course characterized by periods of illness, called flares, and periods of wellness, or remission. Preventing damage and pursuing a stable remission is a main target in SLE treatment. Therefore, the CD24 protein may be administered therapeutically (i.e. during a flare), or prophylactically (i.e. during a remission period) in order to control or prevent the duration, severity and/or frequency of disease flares. In particular the CD24 protein may be administered to patients who are refractory to other treatment options.

a. Administration

The route of administration of the pharmaceutical composition may be parenteral. Parenteral administration includes, but is not limited to, intravenous, intraarterial, intraperitoneal, subcutaneous, intramuscular, intrathecal, intraarticular, and direct injection. The pharmaceutical composition may be administered to a human subject, cat, dog, large animal, or an avian. The composition may be administered 1, 2, 3, 4, 5, 6, 7, 8, 9, 10, 11, or 12 times per day.

b. Combination Treatment

The CD24 protein may be combined with another treatment used to treat SLE. Due to the complexity of the disease there is no standard treatment regimen for all patients with SLE, or all types of SLE, but immunosuppressive and biologic agents are the foundation of inflammatory disease control in SLE. In one embodiment, the CD24 protein is administered on a background of standard of care treatment in order to further attenuate the symptoms of disease, induce remission, as maintenance therapy, or to control flares. Agents currently used for the treatment of SLE include antimalarials (such as hydroxychloroquine), corticosteroids (such as prednisone, hydrocortisone, methylprednisolone, and dexamethasone), immunosuppressives (such as cyclophosphamide and mycophenolate mofetil (MMF), and azathioprine (AZA) which restrain the overactive immune system by blocking the production of immune cells), B cell inhibitors (such as BLyS-specific inhibitors like Belimumab, anti-CD20 antibodies like Rituximab, and Atacicept), costimulatory molecules (such as Abatacept), anti-interferon drugs, anti-cytokine antibodies, and alternative and complementary therapies (such as diet, nutritional supplements, fish oils, ointments and creams, chiropractic treatment, and homeopathy). In some cases, such as lupus nephritis, a high intensity induction therapy is given initially to induce remission (for example, high dose cyclophosphamide or MMF with corticosteroids), which is followed by lower intensity maintenance therapy to maintain stable remission (for example, MMF and AZA), with corticosteroids used to control flares.

In particular, the CD24 protein may be used in combination with corticosteroids in order to reduce the frequency and dose of corticosteroids administered. Corticosteroids have been and still represent the mainstay of SLE treatment, yet they are associated with organ damage, such as preterm osteoporosis, diabetes, cardiovascular disease and accelerated organ failure, which can worsen the disease even further. This can lead to a cycle made of badly controlled disease requiring more aggressive therapy leads to damage which in turn leads to more damage and death. Accordingly, greater relevance should be given to the steroid-sparing potential of new drugs, since sparing steroids is an advantage in the long term. Given the ability of CD24 proteins to reduce the DAMP-mediated inflammation, it may help reduce the damage triggered by uncontrolled disease activity and long-standing corticosteroid use, and thus the reliance on further steroid use.

The CD24 protein may be administered simultaneously or metronomically with other treatments. The term "simultaneous" or "simultaneously" as used herein, means that the CD24 protein and other treatment be administered within 48 hours, preferably 24 hours, more preferably 12 hours, yet more preferably 6 hours, and most preferably 3 hours or less, of each other. The term "metronomically" as used herein means the administration of the agent at times different from the other treatment and at a certain frequency relative to repeat administration.

The CD24 protein may be administered at any point prior to another treatment including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins., 50 mins., 45 mins., 40 mins., 35 mins., 30 mins., 25 mins., 20 mins., 15 mins, 10 mins, 9 mins, 8 mins, 7 mins., 6 mins., 5 mins., 4 mins., 3 mins, 2 mins, and 1 mins. The CD24 protein may be administered at any point prior to a second treatment of the CD24 protein including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins., 50 mins., 45 mins., 40 mins., 35 mins., 30 mins., 25 mins., 20 mins., 15 mins., 10 mins., 9 mins., 8 mins., 7 mins., 6 mins., 5 mins., 4 mins., 3 mins, 2 mins, and 1 mins.

The CD24 protein may be administered at any point after another treatment including about 1min, 2 mins., 3 mins., 4 mins., 5 mins., 6 mins., 7 mins., 8 mins., 9 mins., 10 mins., 15 mins., 20 mins., 25 mins., 30 mins., 35 mins., 40 mins., 45 mins., 50 mins., 55 mins., 1 hr, 2 hr, 3 hr, 4 hr, 6 hr, 8 hr, 10 hr, 12 hr, 14 hr, 16 hr, 18 hr, 20 hr, 22 hr, 24 hr, 26 hr, 28 hr, 30 hr, 32 hr, 34 hr, 36 hr, 38 hr, 40 hr, 42 hr, 44 hr, 46 hr, 48 hr, 50 hr, 52 hr, 54 hr, 56 hr, 58 hr, 60 hr, 62 hr, 64 hr, 66 hr, 68 hr, 70 hr, 72 hr, 74 hr, 76 hr, 78 hr, 80 hr, 82 hr, 84 hr, 86 hr, 88 hr, 90 hr, 92 hr, 94 hr, 96 hr, 98 hr, 100 hr, 102 hr, 104 hr, 106 hr, 108 hr, 110 hr, 112 hr, 114 hr, 116 hr, 118 hr, and 120 hr. The CD24 protein may be administered at any point prior after a previous CD24 treatment including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins., 50 mins., 45 mins., 40 mins., 35 mins., 30 mins., 25 mins., 20 mins., 15 mins., 10 mins., 9 mins., 8 mins., 7 mins., 6 mins., 5 mins., 4 mins., 3 mins, 2 mins, and 1 mins.

4. Methods of Monitoring CD24 Protein Activity

Detecting the activity of the CD24 proteins described herein in patients can be done by looking at serological markers associated with SLE, such as anti-dsDNA, anti-nuclear antibodies (ANA), proteinuria, complement levels (C3 and C4), B and T cell subsets, urine creatine, the IFN signature and IL-6.

The activity of the CD24 protein administered to a subject may also be monitored by detecting the concentration of LDL-C in the subject. The subject may be undergoing treatment with the CD24 protein, such as treatment for SLE, immune-mediated tissue injury, and the like. The concentration of LDL-C may be indicative of the level of CD24 protein activity in the subject, where a decrease in LDL-C in the patient indicates greater CD24 protein activity. The method may comprise obtaining a sample from the subject and detecting the amount of LDL-C in the sample. The sample may be a blood sample such as serum or plasma. Methods of measuring LDL-C concentrations are well-known in the art, such as an ELISA based assay or a Colorimetric/Fluorometric assay following cholesterol esterase and cholesterol oxidase treatment. The amount of LDL-C may be measured by the Friedewald calculation, which may comprise calculating the amount of LDL-C based on amounts of total cholesterol, triglycerides, and high-density lipoprotein cholesterol (HDL-C) measured in the sample. The amount of HDL-C may be measured either by a precipitation procedure with dextran sulfate-$Mg^{2+}$ or by a direct HDL-C assay. The amount of LDL-C may also be measured by the DIRECT LDL™ assay, the homogeneous N-GENEOUS™ LDL assay, or calculated LDL-C values deriving from the ApoB based equation: 0.41TC−0.32TG+1.70ApoB-0.27, (Clin Chem 1997; 43:808-815; the contents of which are incorporated herein by reference). The level of LDL-C can be monitored over time and during the course of CD24 protein treatment in order to monitor the response to treatment.

The amount of CD24 protein being administered to the subject, for treating an indication described herein or known in the art, may be adjusted based on the level of CD24 protein activity detected using LDL-C. The level of LDL-C can be monitored over a period of time or during the course of CD24 protein treatment. If the LDL-C concentration in the subject is reduced to a level within the range of normal, then the amount of CD24 protein administered to the subject may be reduced, such as by lowering the dose of CD24 protein or administering it less frequently. If the LDL-C concentration remains unchanged or remains above the range of normal, then the amount of CD24 protein administered to the subject may be increased, such as by increasing the dose of CD24 protein or administering it more frequently. As an alternative to LDL-C, the concentration of LDL particles (LDL-P) may also be measured to monitor CD24 protein activity. The LDL-P concentration may be detected directly using NMR.

Levels of the CD24 protein administered to the subject may also be monitored, which may be by a method comprising obtaining a sample from the subject and detecting the amount of the CD24 protein in the sample. The sample may be a blood sample such serum or plasma. Protein detection methods are well-known in the art. The CD24 protein in the sample may be detected by any protein detection method, such as an immunoassay including ELISA, Gyros, MSD, Biacore, AlphaLISA, Delfia, Singulex, Luminex, Immuno-PCR, Cell-based assays, RIA, Western blot, an affinity column, and the like. The ELISA method may be sandwich ELISA or competitive ELISA. For example, the ELISA may comprise contacting the sample to an anti-CD24 protein antibody, contacting the CD24 protein-CD24 protein antibody complex with a labeled antibody that binds to the anti-CD24 protein antibody, and measuring the amount of labeled antibody by detecting a signal produced by the label, where the amount of signal correlates to the amount of CD24 protein in the sample.

The amount of CD24 protein administered to the subject may be adjusted (such as by adjusting dose and frequency of administration) based on a pharmacokinetic parameter for the CD24 protein. For example, the amount of CD24 protein administered to the subject may be adjusted to obtain a plasma CD24 concentration of greater than 1 ng/ml. In another example, the amount of CD24 protein administered to the subject is adjusted to maintain a steady state plasma concentration greater than 1 ng/mL. In another example, the amount of CD24 protein administered to the subject may be adjusted to obtain a $C_{max}$ of the CD24 protein of at least about 1 ng/mL. In yet another example, the amount of CD24 protein administered to the subject may be adjusted to achieve a drug exposure level, as defined by the $AUC_{0-inf}$, of the CD24 protein of at least about 400,000 ng*hr/mL.

The present invention has multiple aspects, illustrated by the following non-limiting examples.

EXAMPLE 1

CD24 Pharmacokinetics in Mice 1 mg of CD24Fc (CD24Fc) was injected into naïve C57BL/6 mice and collected blood samples at different timepoints (5 min, 1 hr, 4 hrs, 24 hrs, 48 hrs, 7 days, 14 days and 21 days) with 3 mice in each timepoint. The sera were diluted 1:100 and the levels of CD24Fc was detected using a sandwich ELISA using purified anti-human CD24 (3.3 µg/ml) as the capturing antibody and peroxidase conjugated goat anti-human IgG Fc (5 µg/ml) as the detecting antibodies. As shown in FIG. 3a. The decay curve of CD24Fc revealed a typical biphase decay of the protein. The first biodistribution phase had a half-life of 12.4 hours. The second phase follows a model of first-order elimination from the central compartment. The half-life for the second phase was 9.54 days, which is similar to that of antibodies in vivo. These data suggest that the fusion protein is very stable in the blood stream. In another study in which the fusion protein was injected subcutaneously, an almost identical half-life of 9.52 days was observed (FIG. 3b). More importantly, while it took approximately 48 hours for the CD24Fc to reach peak levels in the blood, the total amount of the fusion protein in the blood, as measured by AUC, was substantially the same by either route of injection. Thus, from a therapeutic point of view, different route of injection should not affect the therapeutic effect of the drug. This observation greatly simplified the experimental design for primate toxicity and clinical trials.

EXAMPLE 2

CD24 for Treating RA

For decades, it has been assumed that rheumatoid arthritis (RA) is predominantly a T-cell mediated autoimmune diseases. In the last two decades, there is a reawaking on the possible role for antibodies and B lymphocytes in RA pathogenesis. Thus, in addition or rheumatoid factors, a host of autoreactive antibodies have been found in RA patients, although it has not been definitively addressed in human. However, several lines of evidence have demonstrated that in the mouse models, antibodies specific for either ubiquitous or tissue specific antigens are sufficient to cause RA symptoms. For instance, antibodies from the K/BxN TCR transgenic mice were found to be fully capable of transferring RA-like diseases in the new host. Likewise, a cocktail for 4 anti-collagen antibodies is now widely used to induce RA in the mouse. This model is now called CAIA, for collagen antibody-induced arthritis.

Genetic analyses of CAIA model indicate critical roles for complement. Although other possibilities exist, these requirements suggest potential involvement of antibody-mediated tissue damage in the pathogenesis of RA. The linkage between tissue damage and inflammation is a long-standing observation in immunology. Nearly two decades ago, Matzinger proposed what was popularly called danger theory. In essence, she argued that the immune system is turned on when it senses the dangers in the host. Although the nature of danger was not well defined at the time, it has been determined that necrosis is associated with the release of intracellular components such as HMGB1 and Heat-shock proteins, which were called DAMP, for danger-associated molecular patterns. DAMP were found to promote production of inflammatory cytokines and autoimmune diseases. In animal models, inhibitors of HMGB1 and HSP90 were found to ameliorate RA. The involvement of DAMP raised the prospect that negative regulation for host response to DAMP can be explored for RA therapy.

CD24-Siglec 10 Interaction in Host Response to Tissue Injuries

Figure 4:
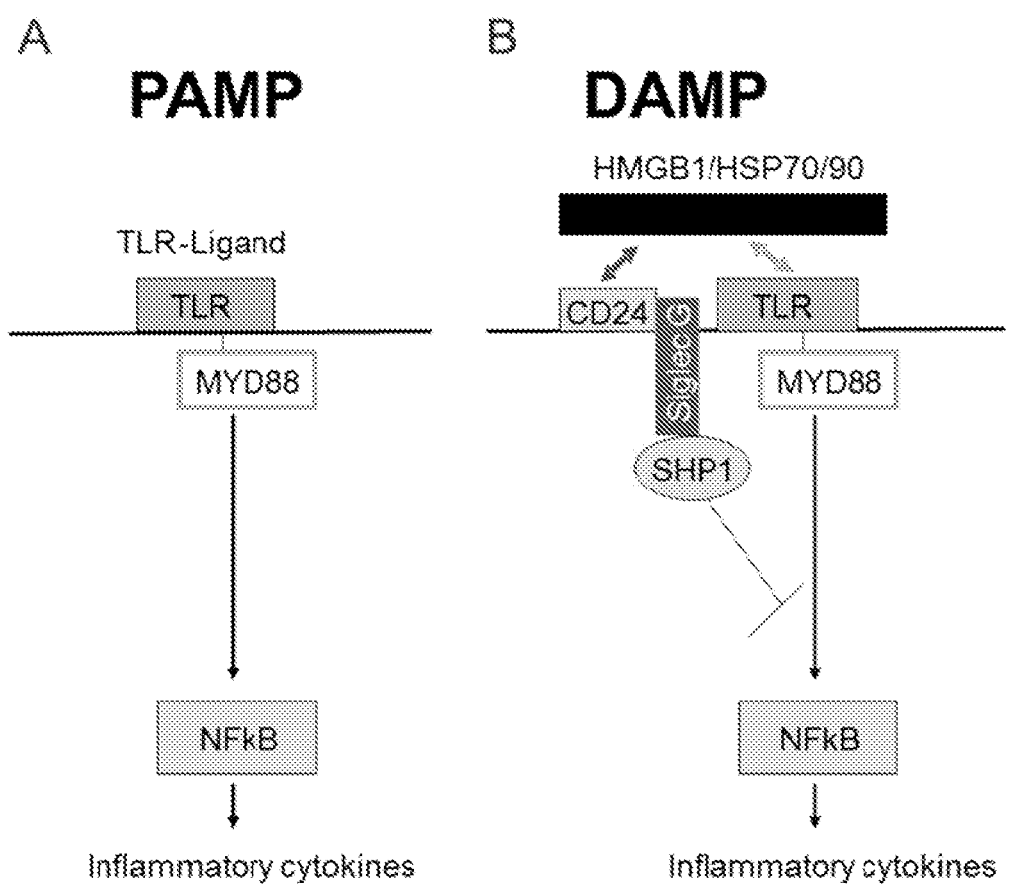
FIG. 4. CD24-Siglec G (10) interaction discriminates between PAMP and DAMP.

Using acetaminophen-induced liver necrosis and ensuring inflammation, it was observed that through interaction Siglec G, CD24 provides a powerful negative regulation for host response to tissue injuries. CD24 is a GPI anchored molecules that is broadly expressed in hematopoietic cells and other tissue stem cells. Genetic analysis of a variety of autoimmune disease in human, including multiple sclerosis, systemic lupus erythromatosus, RA, and giant cell arthritis, showed significant association between CD24 polymorphism and risk of autoimmune diseases. Siglec G is a member of I-lectin family, defined by their ability to recognize sialic acid containing structure. Siglec G recognized sialic acid containing structure on CD24 and negatively regulates production of inflammatory cytokines by dendritic cells. In terms of its ability to interact with CD24, human Siglec 10 and mouse Siglec G are functionally equivalent. However, it is unclear if there is a one-to-one correlation between mouse and human homologues. Although the mechanism remains to be full elucidated, it is plausible that SiglecG-associated SHP1 may be involved in the negative regulation. These data, reported in Science recently, leads to a new model in which CD24-Siglec G/10 interaction may play a critical in discrimination pathogen-associated molecular pattern (PAMP) from DAMP (FIG. 4).

At least two overlapping mechanisms may explain the function of CD24. First, by binding to a variety of DAMP, CD24 may trap the inflammatory stimuli to prevent their interaction with TLR or RAGE. This notion is supported by observations that CD24 is associated with several DAMP molecules, including HSP70, 90, HMGB1 and nucleolin. Second, perhaps after associated with DAMP, CD24 may stimulate signaling by Siglec G. Both mechanisms may act in concert as mice with targeted mutation of either gene mounted much stronger inflammatory response. In fact, DC cultured from bone marrow from either CD24−/− or Siglec G−/− mice produced much higher inflammatory cytokines when stimulated with either HMGB1, HSP70, or HSP90. In contrast, no effect were found in their response to PAMP, such as LPS and PolyI:C. These data not only provided a mechanism for the innate immune system to distinguish pathogen from tissue injury, but also suggest that CD24 and Siglec G as potential therapeutic targets for diseases associated with tissue injuries.

Therapeutic Effect of CD24Fc on Collagen-Antibody-Induced Arthritis

Given the suspected role for innate immunity to tissue injury in the pathogenesis of RA and the role for CD24-Siglec G/10 pathway in negatively regulate such response, the possibility of stimulating this pathway to treat RA was explored. Pathogenesis of essentially all autoimmune diseases involves induction of immune response to autoantigen and autoimmune destruction. The autoimmune destructive phase was focused on, based on the novel function of CD24-Siglec G interaction. Therefore, for the preliminary analysis, collagen antibody-induced arthritis model was adopted to evaluate potential therapeutic effect.

Figure 5:
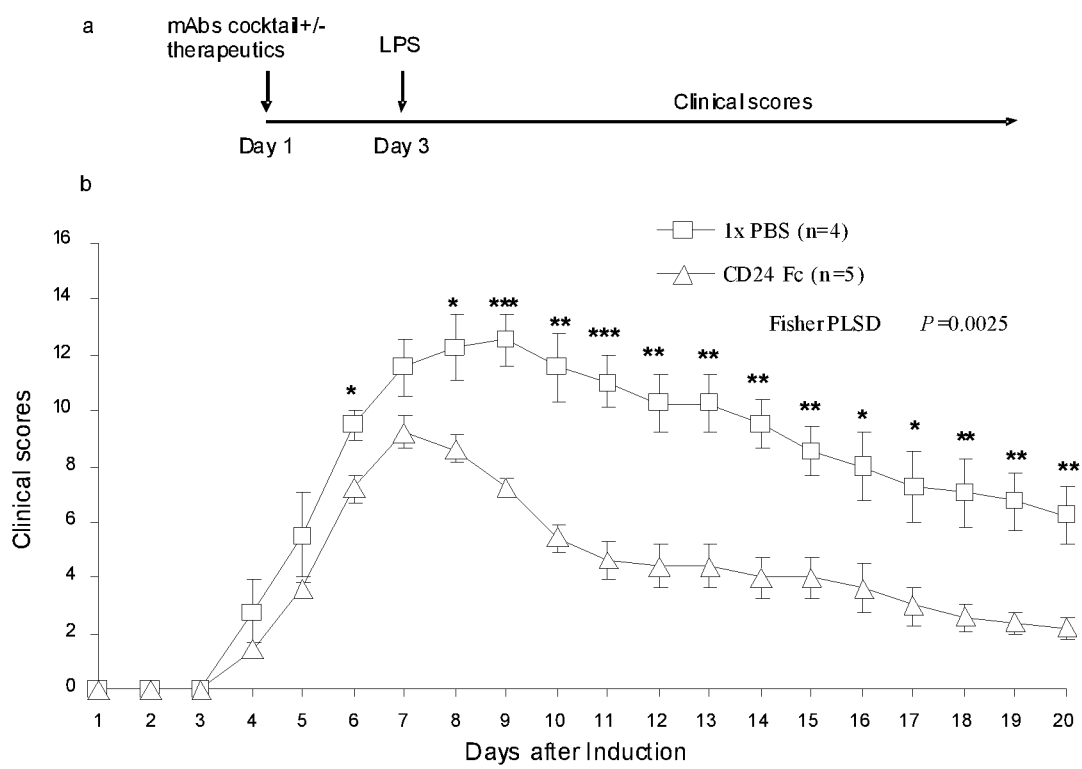
FIG. 5. A single injection of CD24Fc reduces clinical score of CAIA.

As shown in FIG. 5a, the CAIA was induced on 8 weeks old BALB/c mice by i.v. injection of a cocktail of 4 anti-collagen mAbs (MD Biosciences, St. Paul, Minn.) at 2 mg/mouse on day 1, and i.p. injection of 100 µg/mouse of LPS (MD Bioscience) on day 3. The mice were treated on day 1 with either 1 mg CD24Fc or equal volume of 1×PBS vehicle as negative control. As shown in FIG. 5b, in comparison with vehicle control, CD24Fc provided highly significant therapeutic effects.

Figure 6:
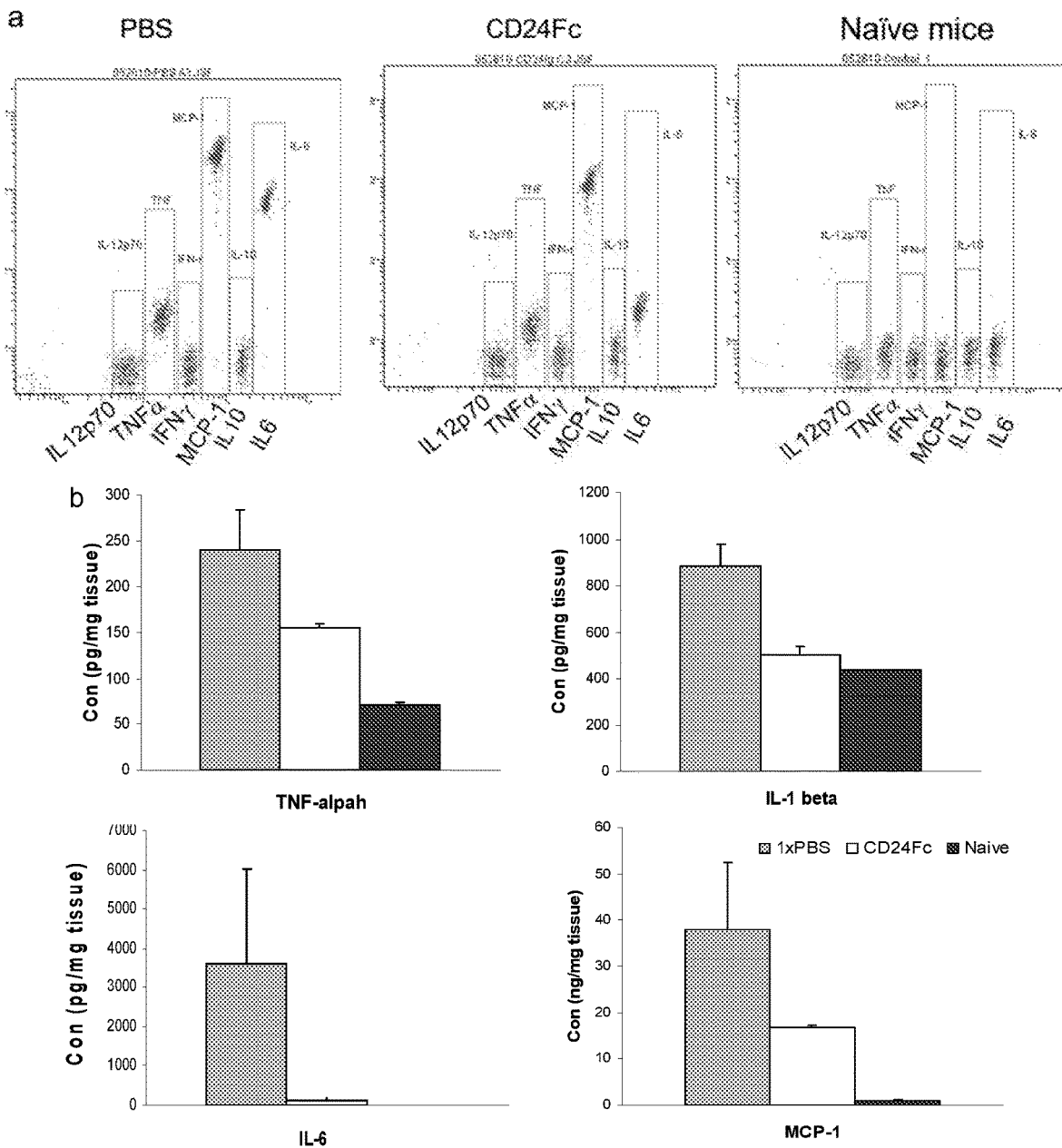
FIG. 6. CD24Fc reduces the levels of inflammatory cytokines in the joint and CAIA. CAIA initiated and treated as diagramed in FIG. 5A. The inflammatory cytokines were measured by cytokine bead array from BD Pharmingen.

To understand the mechanism by which CD24Fc reduces arthritis in this model, cytokines were measured from homogenized joints of CD24Fc treated mice or PBS control group, and measured the supernatant of 200 µg tissue homogenates by cytokine beads array. A typical example is shown in FIG. 7a, while the summary data are shown in FIG. 6b. These data demonstrated that systematically administrated CD24 reduces the levels of multiple inflammatory cytokines including TNF-$\alpha$, IL-6, MCP-1(CCL2) and IL-$\beta$.

Figure 7:
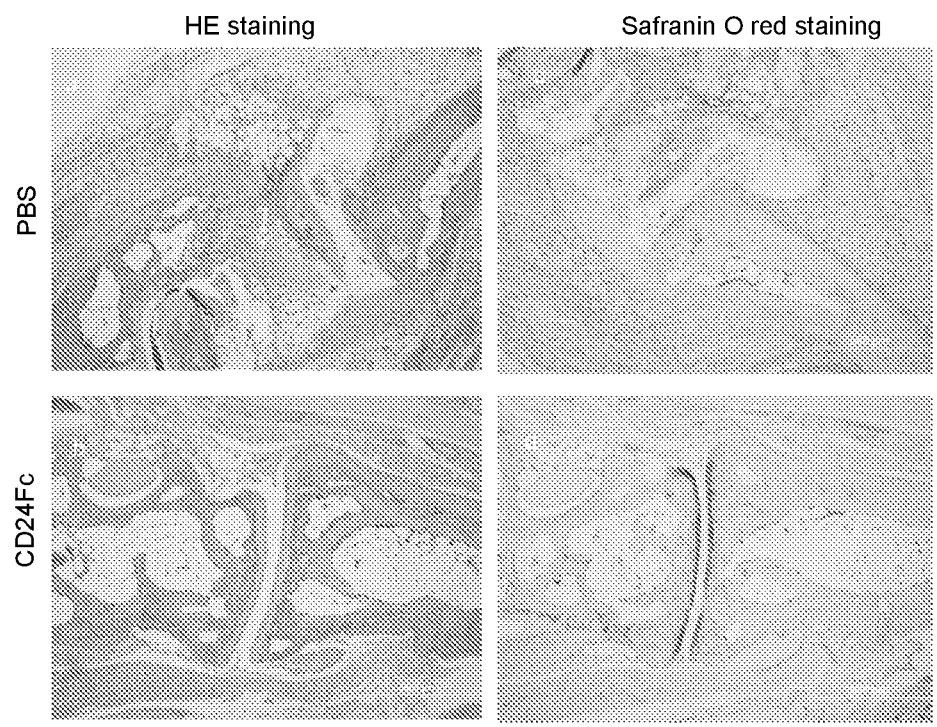
FIG. 7. CD24Fc reduces inflammation and destruction of cartilage in the joint. On day 7, front and hind paws were dissected from both CD24Fc treated and control mice, fixed in 4% paraformaldehyde for 24 hours followed by decalcification with 5% formic acid. The paws were then embedded in paraffin and the longitudinal section were stained with H&E and Safranin 0 red (Sigma-Aldrich).

The effect of CD24Fc is substantiated by histological analysis of the synovial joints of CAIA mice, as presented in FIG. 7. On day 7 after induction of arthritis, H&E staining demonstrated that the joint synoviums in the PBS group are heavily infiltrated with inflammatory cells including neutrophil, macrophage, and lymphocytes (FIG. 7a). This was much reduced in the CD24Fc treated mice (FIG. 7b). In addition, sever cartilage damages were revealed by the loss of safranin O red staining in PBS-treated (FIG. 7c) mice, but not CD24Fc-treated group (FIG. 7d).

Figure 8:
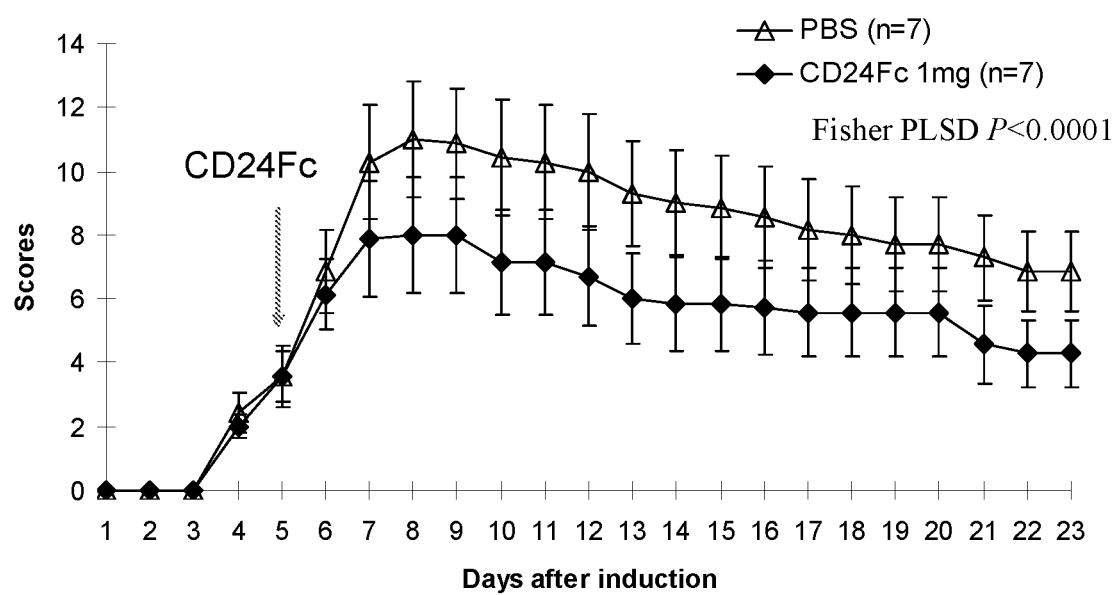
FIG. 8. Therapeutic effect of CD24Fc administrated on day 5 of CAIA induction. The CAIA-induced mice were randomized into two groups, receiving either vehicle (PBS) or CD24 Fc. The mice were scored double blind. Representative of three independent experiments are shown.

To determine whether mice, CD24Fc have therapeutic effect on ongoing RA, treatment was started at either 5 or 7 days after induction of RA. As shown in FIG. 8, significant reduction of RA score was observed as soon as two days after CD24Fc treatment. The therapeutic effect lasted for the remaining period of observation even without additional treatment. These data further strengthen the therapeutic potential of CD24Fc on ongoing diseases.

Figure 9:
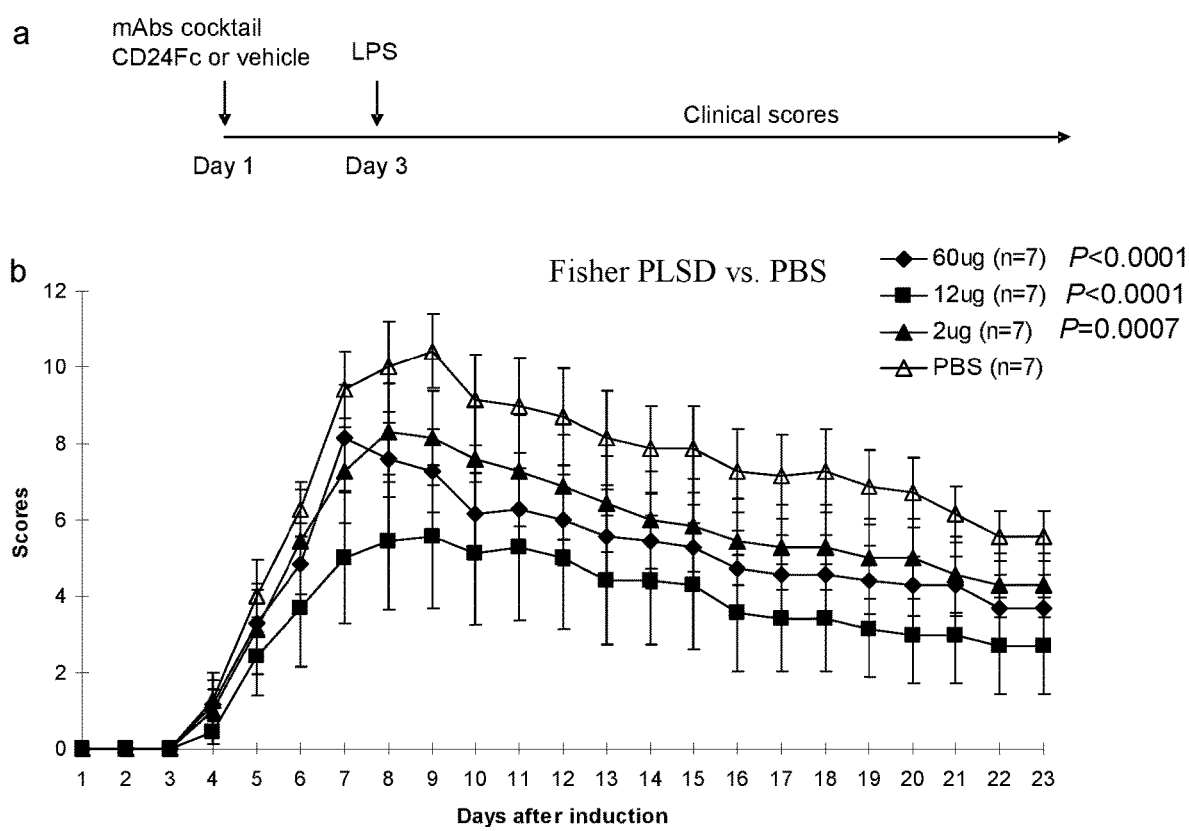
FIG. 9. Low doses of CD24Fc prevent development of CAIA.

In order to estimate the therapeutic doses of CD24Fc in human, CD24Fc was titrated through a wide range of doses. As shown in FIG. 9, as little as 2 microgram/mice is sufficient to have statistically significant therapeutic effect.

Siglecg-Dependent Therapeutic Effect of CD24Fc

Figure 10:
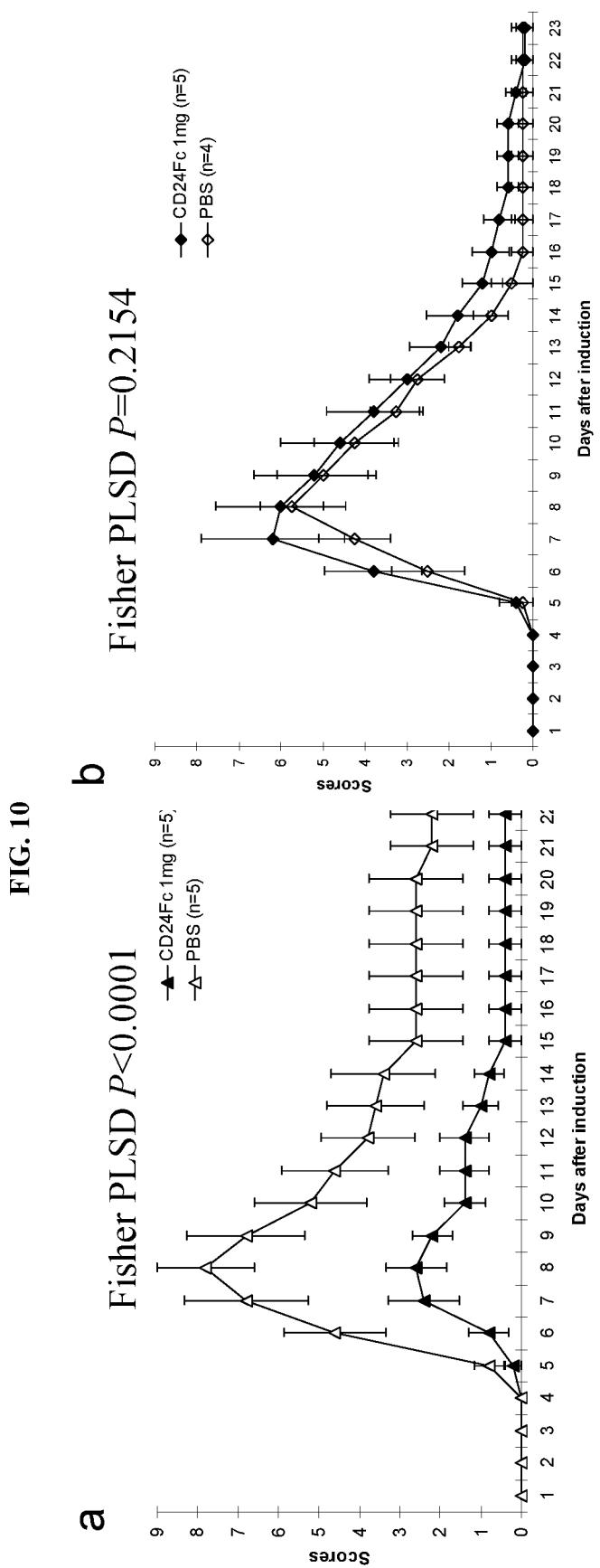
FIG. 10. Siglecg is essential for therapeutic effect of CD24Fc, WT (FIG. 10A) and Siglecg$^{-/-}$ mice (FIG. 10B) received either vehicle control or CD24Fc in conjunction of a cocktail of anti-collagen mAbs. The clinical scores were recorded daily double blind.

To determine whether CD24Fc protect mice by interacting with Siglec G, it was determined if the therapeutic effect depends on the Siglecg gene. Since the Siglecg-deficient mice were produced with ES cells from C57BL/6 mice, WT C57BL/6 mice were used as control. As shown in FIG. 10a, since the B6 mice are known to be less susceptible to the CAIA, the overall disease score is lower than that observed in the BALB/c mice. Nevertheless, a single injection of the CD24Fc essentially wiped out the clinical signs in the WT mice. Importantly, even though the disease is less severe in the Siglecg-deficient mice, CD24Fc had no therapeutic effect. Therefore, the therapeutic effect of CD24Fc is strictly dependent on the Siglecg gene.

Taken together, the data described herein demonstrates high therapeutic efficacy of CD24Fc for CAIA. Given our extensive data on safety, stability and our successful manufacture of CD24Fc all point to great potential of the fusion protein as a therapeutic for RA.

EXAMPLE 3

A Variant CD24 has Improved Activity Over Wild-Type CD24

This example shows that a CD24 polypeptide containing human CD24 missing the polymorphic amino acid at position 57 (SEQ ID NO: 1) (CD24Fc) is more effective for treating RA than a CD24 polypeptide containing wild-type CD24 (SEQ ID NO: 2) (CD24$^V$Fc).

Methods

Antibodies, Fusion Proteins and Other Materials

CD24Fc and CD24vFc were manufactured by OncoImmune, Inc.; Bovine type II collagen, Catalog No. 20022, Chondrex Inc., Redmond, Wash.; a cocktail of 4 anti-collagen mAbs Catolog No. CIA-MAB-50 for BALB/c and CIA-MAB-2C for C57BL/6 mice, MD Bioproducts, St. Paul, Minn.; Chick type II collagen, Catalog No. 20011, Chondrex Inc., Redmond, Wash.; Complete Freund's adjuvant: Catalog No. 7008, Chondrex Inc., Redmond, Wash., with heat-killed *M. tuberculosis* H37 Ra (non-viable) at concentration of 1 mg/ml; Complete Freund's adjuvant: Catalog No. 7023, Chondrex Inc., Redmond, Wash., with heat-killed *M. tuberculosis* H37 Ra (non-viable) at concentration of 5 mg/ml; Incomplete Freund's adjuvant: Catalog No. 7002, Chondrex Inc., Redmond, Wash.; Lipopolysaccharide (LPS), Catalog No. 9028, Chondrex Inc., Redmond, Wash., from *E. coli* 0111:B4; Cytometric Bead Array (CBA) Mouse Inflammation Kit, Catalog No. 552364, BD Biosciences, San Jose, Calif.; Cytometric Bead Array (CBA) Human Inflammatory Cytokines Kit, Catalog No. 551811, BD Biosciences, San Jose, Calif.

Experimental Animals

BALB/cAnNCr (01B05, NCI) and C57BL/6NCr (01055, NCI) mice, male, 7 weeks old, were purchased from the National Cancer Institute (NCI) at Frederick, Md. DBA/1J (000670, JAX) mice, male, 7 weeks old, were received from Jackson Laboratories. All mice were quarantined for 7 days prior to immunization. During quarantine, the animals were examined for general health and acceptability for use in this study. Individual animals were identified by ear mark. Animal cages were identified by study number, animal number, and group number. To minimize cage variation, different treatments were given to individual mouse in the same cages and scored in a double-blind protocol.

CAIA Model

BALB/c mice (8 weeks old) received mAbs (2 mg/mouse) on day 1 in conjunction with either vehicle or fusion proteins. Mice received LPS (100 µg/mouse) on day 3, and were observed daily for 3 weeks. The fusion proteins (0.2 or 1 mg/mouse) or vehicles were injected once on day 1. In the C57BL/6 mice, the dose of anti-collagen antibodies was either 2 mg/mouse or 4 mg/mouse.

CIA Models

CIA in DBA/1 mice. On day 1, 8-week old DBA/1 mice were immunized with 100 µL of collagen-CFA emulsion (made by mixing 2 mg/ml of bovine type II collagen with equal volume of CFA containing 1 mg/ml of *M. tuberculosis*) subcutaneously at the base of the tail. On day 10, mice were booster-immunized with 60 µL of collagen-IFA emulsion (made by mixing 2 mg/ml of collagen with equal volume of IFA) subcutaneously 1.5 cm from the tail base. Treatments were initiated either before or after the development of symptom of arthritis.

CIA in C57BL/6 mice. On day 1, 8-week old C57BL/6 mice were immunized with 100 µL of collagen-CFA emulsion (made by mixing 4 mg/ml of chick type II collagen with equal volume of CFA containing 5 mg/ml of *M. tuberculosis*) intradermally at the base of the tail. On day 21, booster immunization with the same collagen-CFA emulsion was administered intradermally 1.5 cm from the tail base. On day 28, mice with clinical symptoms were randomized to receive either vehicle or CD24Fc.

Treatment in RA Models

The scoring of arthritis was based on the following scale. 0, normal; 1, mild, but definite redness and swelling of the ankle or wrist, or apparent redness and swelling limited to individual digits, regardless of the number of affected digits; 2, moderate redness and swelling of ankle of wrist; 3, severe redness and swelling of the entire paw including digits; 4, maximally inflamed limb with involvement of multiple joints. A combined score of 4 limbs in a mouse was reported as the disease score for the mouse.

Prophylactic treatment in CAIA was initiated at the same time as the anti-collagen antibodies.

Prophylactic model in CIA model in DBA/1 mice: On day 17, the immunized mice were randomly divided into two groups and were treated with vehicle (PBS) or given doses of CD24Fc. The mice were observed double blind for three weeks.

Therapeutic CIA in DBA/1 model with ongoing diseases were initiated at either 25 days after the first immunization using mice with clinical scores from 3 to 8.

Therapeutic CIA in the C57BL/6 mice was initiated on day 28 or using only those mice with a clinical score from 3 to 8.

Statistical Methods

Group means and standard deviation values (when deemed appropriate) were calculated for all numerical data obtained. The difference between CD24Fc and control mice was statistically analyzed with Fisher PLSD Test, or t-test for pairwise comparisons.

Results

Figure 11:
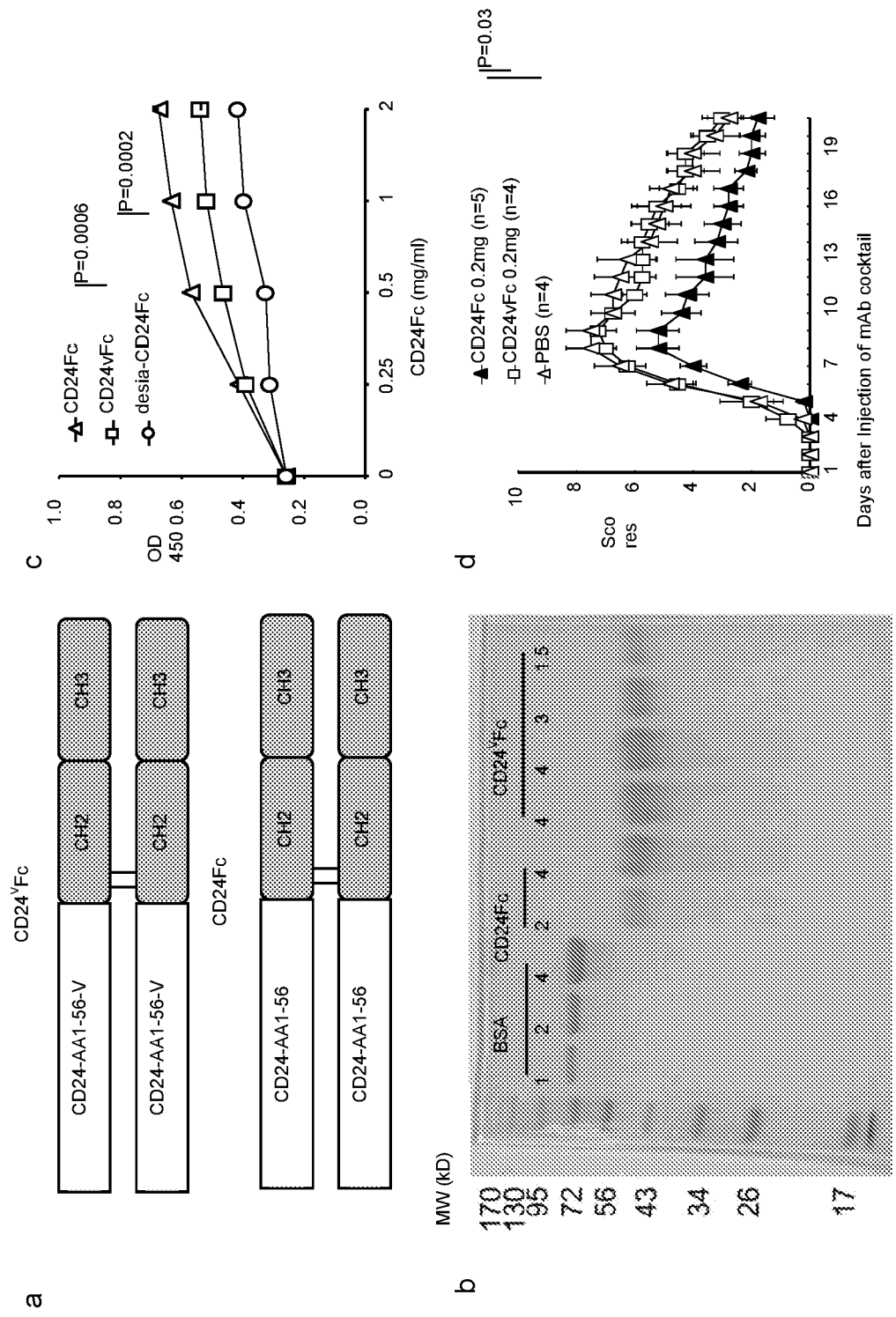
FIG. 11. Construction of CD24$^V$Fc and CD24Fc.
Figure 11:
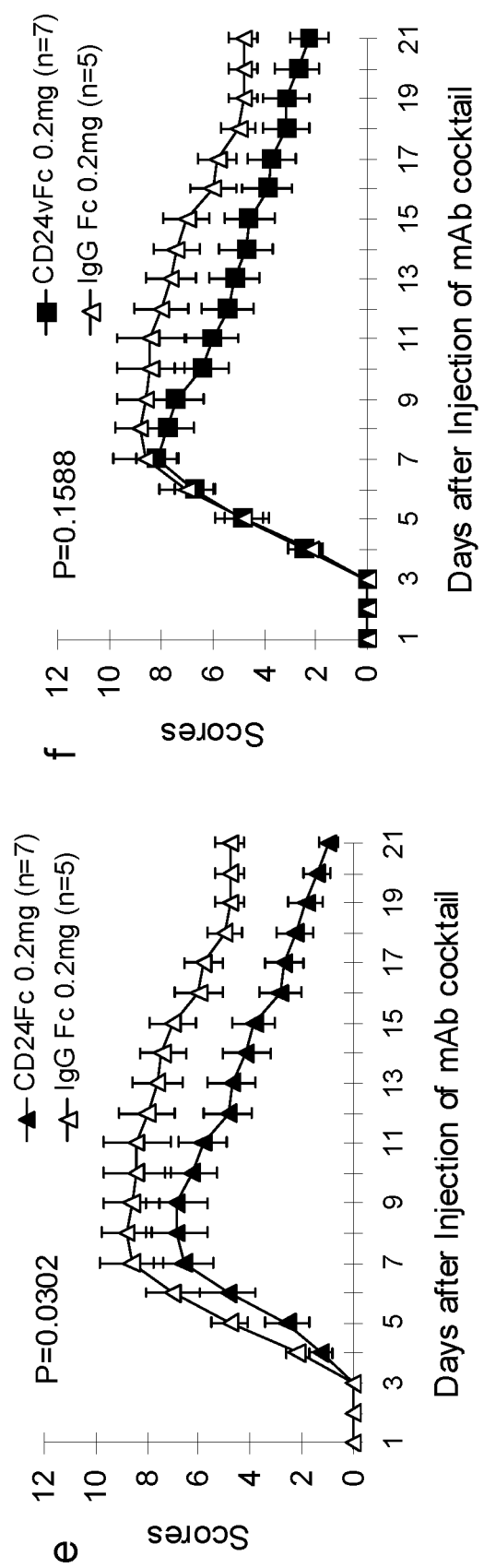

Therapeutic Effect of Non-Polymorphic CD24Fc on Collage-Antibody-Induced Arthritis Human mature CD24 exists in two allelic forms, in which either a valine or alanine is present at the C-terminus (position 57 of the CD24 amino acid sequence). Fusion proteins including either allelic form may provoke anti-drug antibodies in some RA patients. Thus, in order to avoid immunogenicity, it was tested whether the polymorphic residue can be removed from CD24, while maintaining regulatory function of CD24. As diagrammed in FIG. 11A, two fusion proteins were created, one with the entire extracellular domain of CD24$^V$ allele (CD24$^V$Fc) (the mature CD24 sequence having SEQ ID NO: 2), while the other had a one amino acid deletion at the C-terminus of the resulting mature CD24 (CD24Fc) (the mature CD24 sequence having SEQ ID NO: 1). Both forms were expressed and purified to a similar degree (FIG. 11B).

To determine whether the valine on CD24 is required for CD24-Siglec 10 interaction, their binding of CD24Fc and CD24$^V$Fc to a Siglec 10Fc fusion protein was compared. As shown in FIG. 11C, CD24Fc interacted with Siglec 10Fc in a dose-dependent manner. The interaction depended on sialic acid on CD24Fc as pre-treatment of CD24Fc with sialidase prevented the binding. Surprisingly, while CD24$^V$Fc also interacted with Siglec 10Fc, the interaction was significantly weaker than that of CD24-Fc-Siglec 10Fc. The CAIA was induced in 8 week-old BALB/c mice by i.v. injection of a cocktail of 4 anti-collagen mAbs in conjunction with CD24$^V$Fc, CD24Fc, human IgG1Fc or equal volume of 1×PBS vehicle as negative control. As shown in FIG. 11D, in comparison with vehicle control, CD24Fc provided highly significant therapeutic effects. Surprisingly, CD24$^V$Fc was far less effective, with activity not very different from the negative control. In experiments similar to the ones shown in FIG. 11D, FIGS. 11E and 11F also show that CD24Fc is more effective than CD24$^V$Fc, although unlike in the experiments in FIG. 11D, CD24$^V$Fc did have more activity than the negative control. Comparisons of the therapeutic effects of CD24Fc and CD24$^V$FC indicate that deleting the polymorphic amino acid residue is not only likely to remove a potential issue of immunogenicity, but it also significantly increases the anti-inflammatory activity of the CD24 protein. Since the Fc portion was identical in the two constructs, the therapeutic effect is largely attributable to CD24 function. Since Fc protein often exacerbated arthritis (data not shown), vehicle controls were used for in vivo studies to avoid inducing a confounding effect.

Therapeutic Effect of CD24Fc in Collagen-Induced Arthritis (CIA) Models

Figure 12:
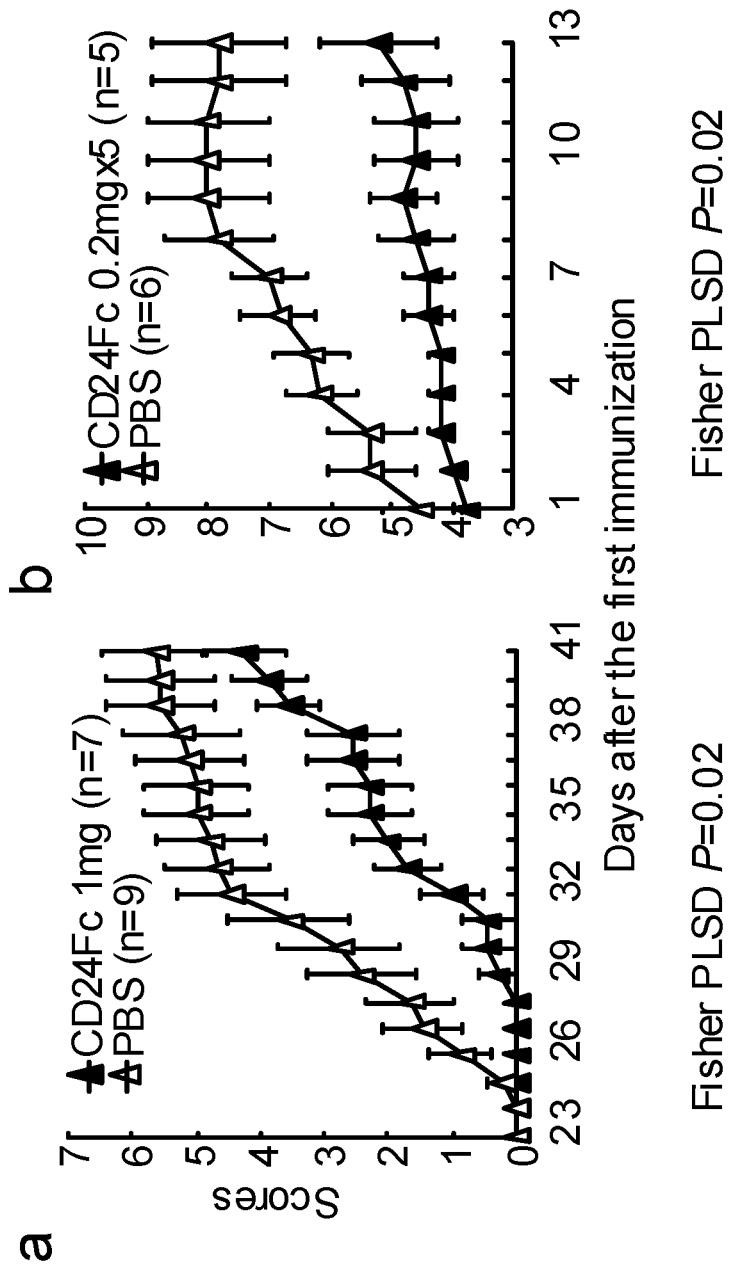
FIG. 12. CD24Fc conferred protection against CIA in DBA/1 mice.

Since CAIA primarily reflects joint inflammation initiated by antibody-induced tissue injuries, and since RA involves both adaptive and innate immune-mediated destruction that can be better reflected in CIA setting, two CIA models were used to study to potential therapeutic effect of the CD24Fc. First, the prophylactic effect of CD24Fc were tested in the DBA/1 mouse. As shown in FIG. 12A, treatment with a single dose of CD24Fc prior to the development of clinical symptoms substantially reduced subsequent disease scores (P=0.02). To determine whether CD24Fc confers therapeutic effect for ongoing CIA in the DBA/1 mice, the treatment was initiated when the mice had arthritis scores from 3 to 8. The CD24Fc (200 µg/mouse) or vehicle was delivered every other day for 5 times. As shown in FIG. 12B, a clear reduction of arthritis score was observed as early as after two treatments. Significant reduction of clinical symptoms was observed in the CD24Fc group (P=0.02).

Figure 13:
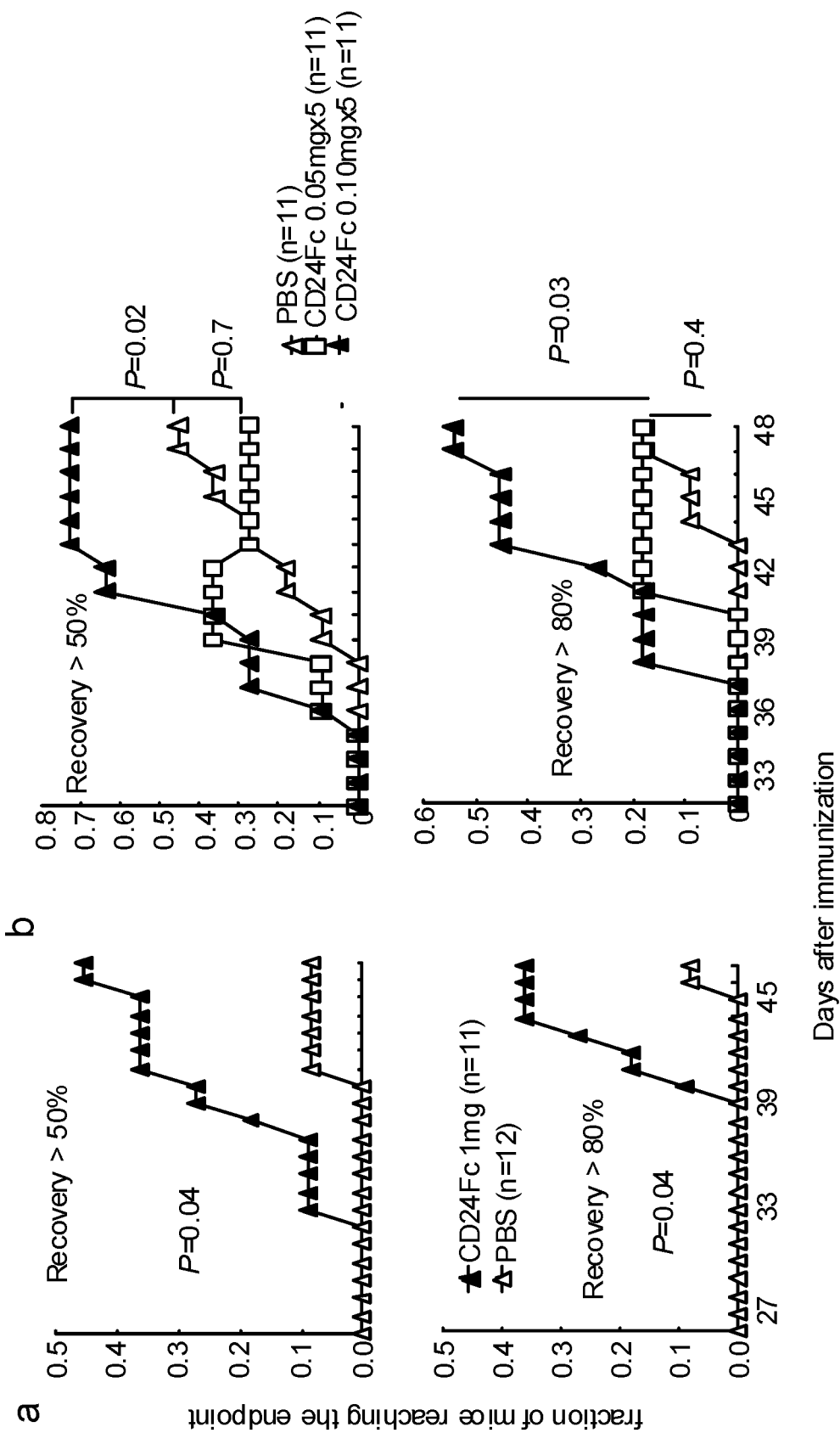
FIG. 13. CD24Fc caused rapid recovery in mice with ongoing chicken CIA. On day 1, 8-week old C57BL/6 mice were immunized with 100 μL of collagen-CFA emulsion (made by mixing 4 mg/ml of chick type II collagen with equal volume of CFA containing 5 mg/ml of *M. tuberculosis*) intradermally at the base of the tail. On day 21, booster immunization with the same collagen-CFA emulsion was administered intradermally 1.5 cm from the tail base.

It has been reported that chicken collagen induces severe arthritis in C57BL/6 background. Therefore, this model was used to substantiate the therapeutic effect of CD24Fc. Since a significant variation in disease score was observed within the same group, 50% and 80% reductions of disease scores were used as the endpoints of the study. The percentage of mice that reached either therapeutic endpoint over a three week period was compared. As shown in FIG. 13A, CD24Fc accelerated recovery of mice after severe clinical signs had developed. To test the therapeutic effect at the peak of diseases, another week was allowed to pass for mice to reach peak clinical score, at which point mice were treated with repeated injections of either 100 or 50 µg/mouse (once every other day for a total of 5 injections). As shown in FIG. 13B, a transient increase of recovery was achieved with 50 µg/mouse/injection. However, a sustained recovery was achieved with only 100 µg/mouse/injection. These data demonstrate a dose-dependent therapeutic effect even when the drug was administered at the peak of diseases.

CD24Fc Inhibits Production of Inflammatory Cytokines by a Human Macrophage Cell Line with shRNA Silencing of CD24

Figure 14:
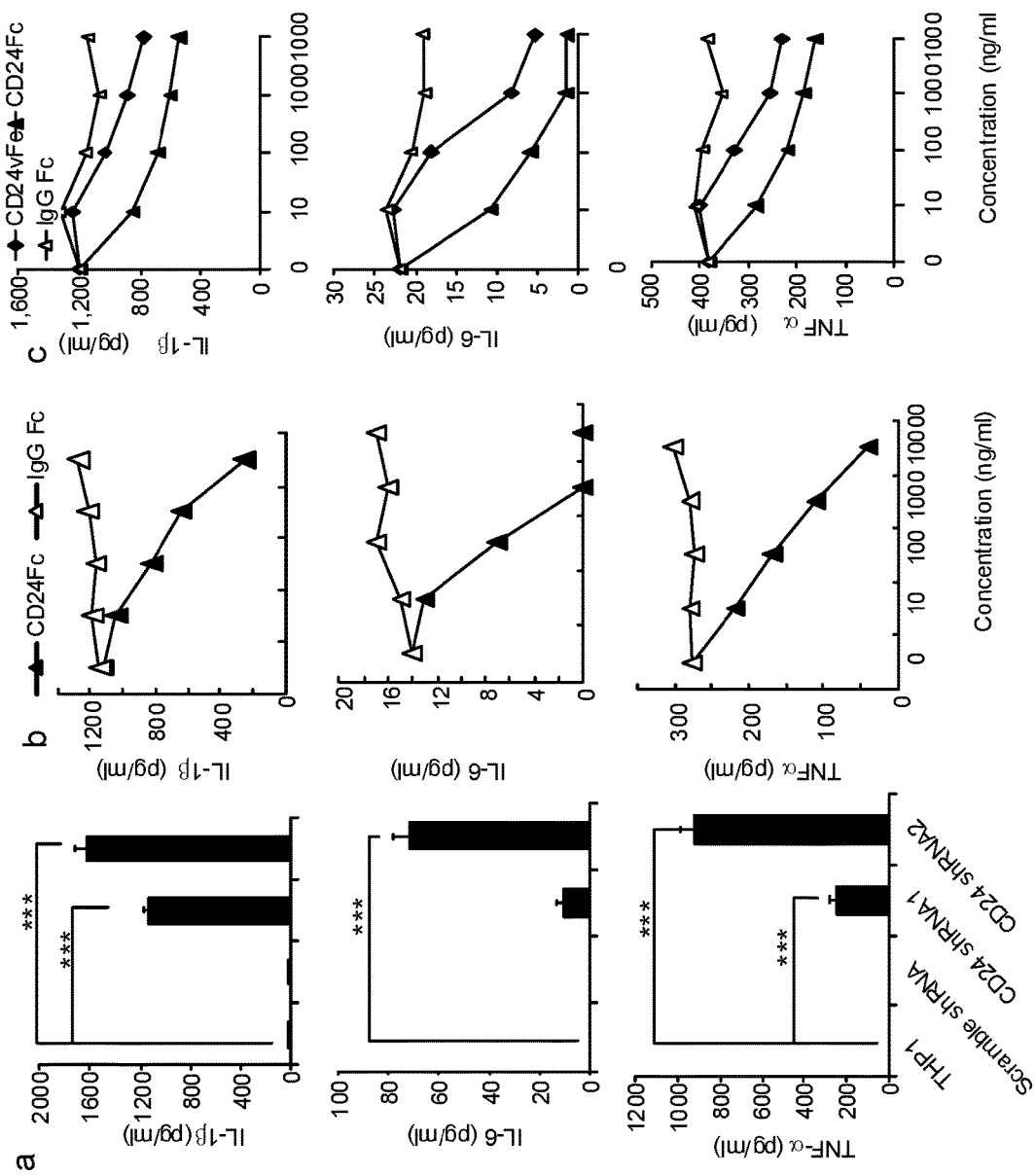
FIG. 14. CD24 inhibited inflammatory cytokine production by human macrophages.

To determine whether CD24 regulates production of inflammatory cytokines in human cell line, CD24 was silenced in human THP1 cell line and then differentiation into macrophage was induced by treating the cells with PMA. As shown in FIG. 14A, CD24 silencing substantially increased production of TNFα, IL-1β, and IL-6. These data demonstrate an essential role for endogenous human CD24 in production of inflammatory cytokines. Importantly, CD24Fc strongly inhibited production of TNFα, as well as IL-1β and IL-6 (FIG. 14B). Consistent with the therapeutic effect in vivo, CD24$^V$Fc was approximately 10-fold less effective in inhibiting the production of inflammatory cytokines in the macrophage cell line (FIG. 14C).

CD24Fc Confers Protection by Signaling Through Siglec G

Figure 15:
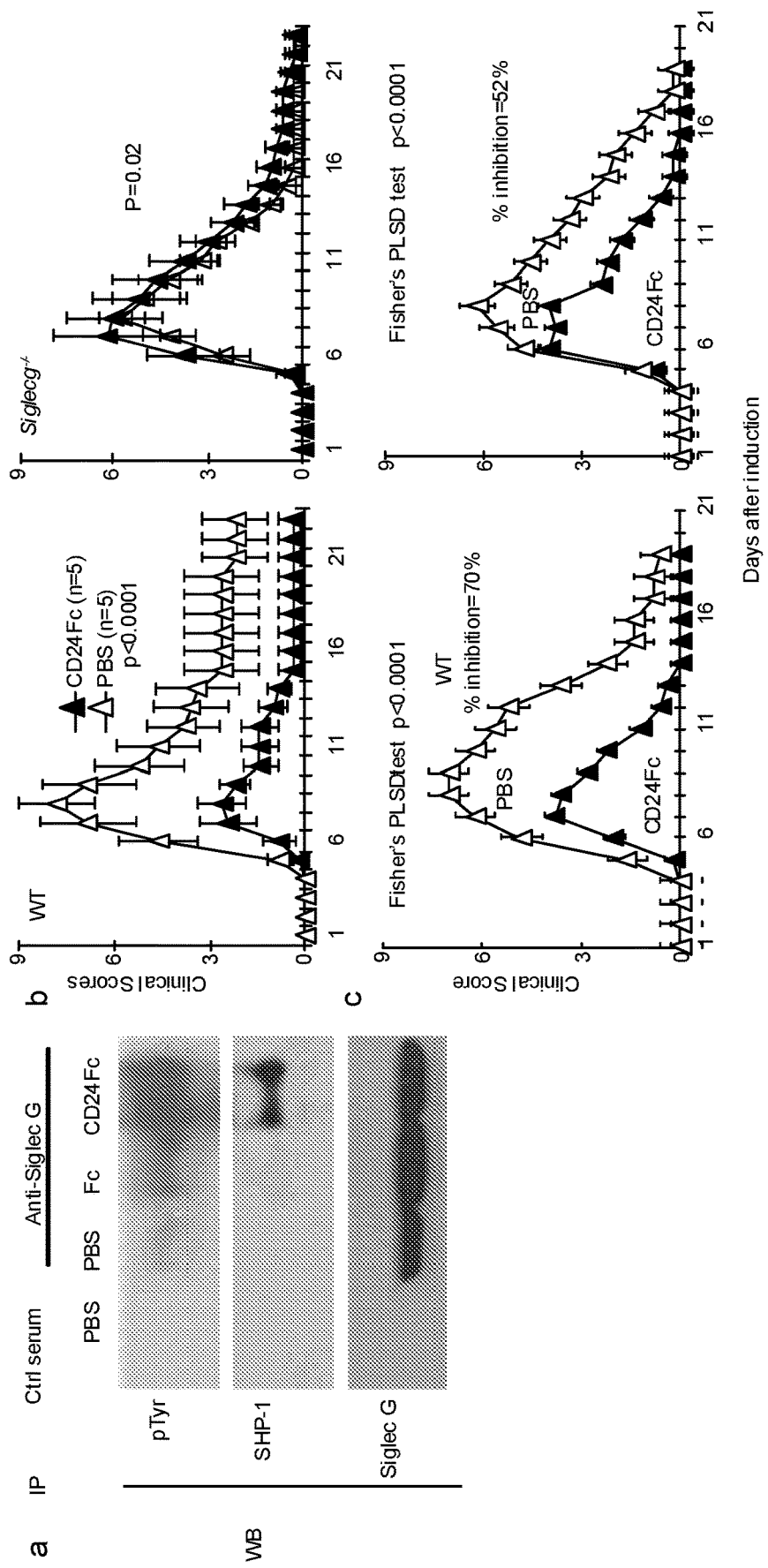
FIG. 15. Contribution of Siglec G to protection by CD24Fc.

It has been reported that CD24Fc interacts with Siglec G in mice and Siglec 10 in humans. To determine whether CD24Fc signals through Siglec G, spleen cells from CD24 mice were incubated with either vehicle, Fc or CD24Fc for 30 min, and tyrosine phosphorylation and SHP-1 binding to Siglec G were measured. As shown in FIG. 15A, CD24Fc strongly stimulated tyrosine phosphorylation of Siglec G. Correspondingly, the amount of SHP1 co-precipitated with Siglec G was dramatically increased. These results demonstrate that CD24Fc is capable of signaling through Siglec G.

To test the significance of CD24Fc signaling through Siglec G in therapy of RA, WT mice and Siglec G-deficient mice were compared for their response to CD24Fc. As shown in FIG. 15B, when lower doses of anti-collagen antibodies were used, disease was less severe, yet the protection was completely dependent on the Siglecg gene. However, with increased doses of anti-collagen antibodies, the protective effect was only partially dependent on Siglecg, as the protection was still obvious, albeit less pronounced (52% in KO vs 72% in WT mice) (FIG. 15C). These data demonstrate that while CD24Fc can signal through Siglec G to confer protection against CAIA, an additional mechanism exists that allows CD24Fc to protect against RA in the absence of Siglec G.

Discussion

Taken together, the results demonstrate that CD24Fc has potent therapeutic effects in three mouse RA models, including a CAIA and two CIA models. The efficacies in multiple models indicates that CD24Fc has a therapeutic effect among RA in humans with different underlying pathogenesis. For decades, it has been assumed that RA is predominantly a T-cell mediated autoimmune diseases. In the last two decades, there has been a re-awaking on the possible role for antibodies and B lymphocytes in RA pathogenesis. Thus, in addition to rheumatoid factors, a host of autoantibodies have been found in RA patients. Several lines of evidence have demonstrated that in the mouse models, antibodies specific for either ubiquitous or tissue specific antigens are sufficient to cause RA symptoms. For instance, antibodies from K/BxN TCR transgenic mice were found to be fully capable of transferring RA-like diseases in the new host. Likewise, a cocktail of 4 anti-collagen antibodies is now widely used to induce RA in mice. Genetic analyses of the CAIA model indicate critical roles for complement. Although other possibilities exist, these requirements suggest potential involvement of antibody-mediated tissue damage in the pathogenesis of RA. The efficacy of CD24Fc in this model demonstrates that the fusion protein may be useful for antibody-mediated destruction phase in RA patients.

The CIA model is commonly used for RA as it can mimic both induction and effector function of both adaptive and innate immunity. Two CIA models were used to validate the therapeutic effect of CD24Fc. Bovine collagen-induced RA in DBA/1 mice is the most commonly used model. The above data show that CD24Fc reduced the disease score either before or after onset of disease in this model. One drawback of the bovine CIA model is that only relatively small numbers of strains are susceptible. In particular, C57BL/6 mice, which are commonly used for genetic studies are resistant. More recently, a protocol has been developed to induce CIA in C57BL/6 mice using chicken collagen. As shown above, CD24Fc accelerated recovery of arthritis induced by chicken collagen. The fact that the CD24Fc confers protection in multiple models demonstrates the robustness of its therapeutic effect.

An important issue relating to drug development is mechanism of action. Since it has been reported that CD24Fc binds to both Siglec G and human Siglec 10, the significance of this interaction was evaluated. In vitro, as shown above, CD24Fc signals through Siglec G and triggers tyrosine phosphorylation. In vivo, as shown above, CD24Fc works at least in part through Siglec G. These results demonstrate that it is plausible that CD24Fc protects against RA through strengthening the Siglec G-mediated protection against innate immunity to DAMPs. To date, no RA drug has been developed by fortifying the negative regulation over innate response to DAMPs. Therefore, CD24Fc and other fusion proteins containing variant CD24 missing the polymorphic A/V amino acid (SEQ ID NO: 1) represents a new class of therapeutics for RA. This approach may be preferable to antibodies targeting individual DAMPs or inflammatory cytokines. Since multiple DAMPs are released during autoimmune destruction, targeting individual DAMP may be less effective than targeting a broad-spectrum regulator such as CD24-Siglec G pathway. Nevertheless, it should be pointed out that the data in this example demonstrate that the protection is not completely dependent on signaling through Siglec G. At least two additional mechanisms can be invoked. First, by binding to DAMPs, CD24 may reduce the amounts of DAMPs available for their agonist receptors, such as RAGE, TLR. Second, since CD24 is heterogeneously glycosylated, it may bind to other members of Siglecs to confer negative regulation.

CONCLUSION

A fusion protein comprising a non-polymorphic extracellular domain of human CD24 (comprising SEQ ID NO: 1) protects mice against arthritis initiated by either anti-collagen antibodies or immunization of collagen. The protection is at least partially dependent on its interaction with Siglec G. The data demonstrate the potential of harnessing the negative regulation of innate immunity to tissue injuries. Unexpectedly, the non-polymorphic variant of CD24 is superior to wild-type CD24 in suppressing inflammatory cytokine production and protecting mice against RA.

EXAMPLE 4

CD24 Pharmacokinetics in Humans

This example shows an analysis of the pharmacokinetics of a CD24 protein in humans. This was derived from a Phase I, randomized, double-blind, placebo-controlled, single ascending dose study to assess the safety, tolerability, and PK of CD24Fc in healthy male and female adult subjects. A total of 40 subjects in 5 cohorts of 8 subjects each were enrolled in this study. Six of the 8 subjects in each cohort received study drug and 2 subjects received placebo (0.9% sodium chloride, saline). The first cohort was dosed with 10 mg. Succeeding cohorts received 30 mg, 60 mg, 120 mg, and 240 mg of CD24Fc or matching placebo and were dosed at least 3 weeks apart to allow for review of safety and tolerability data for each prior cohort. Administration of the next higher dose to a new cohort of subjects was permitted only if adequate safety and tolerability had been demonstrated.

In each cohort, the initial 2 subjects were 1 study drug recipient and 1 placebo recipient on Day 1. The 3rd to 5th and 6th to 8th subjects were dosed after Day 7 (a minimum of 24 hours apart between the subgroups). Each subject was dosed at least 1 hour apart in the same subgroup. If necessary, dosing of the rest of subjects was delayed pending review of any significant safety issues that may have arisen during the post-dose period involving the first or second subgroups in that cohort. The subsequent cohort was dosed at least 3 weeks after the prior cohort.

Screening Period:

The Screening Visit (Visit 1) occurred up to 21 days prior to the beginning of the active treatment period. After providing informed consent, subjects underwent screening procedures for eligibility.

Treatment Period:

Subjects were admitted to the Clinical Pharmacology Unit (CPU) on Day −1 (Visit 2), and the randomized treatment period began on Day 1 following a 10-hour minimum overnight fast. Subjects were randomly assigned to treatment with CD24Fc or placebo as a single dose. Subjects remained confined until the morning of Day 4.

Follow-Up:

All subjects returned to the CPU on Day 7, Day 14, Day 21, Day 28, and Day 42 (±1 day) for follow-up visits (Visit 3, Visit 4, Visit 5, Visit 6, and Visit 7). Visit 7 was the final visit for all subjects.

Duration of Treatment: The total study duration for each subject was up to 63 days. Single-dose administration occurred on Day 1.

Number of Subjects:

Planned: 40 subjects

Screened: 224 subjects

Randomized: 40 subjects

Completed: 39 subjects

Discontinued: 1 subject

Diagnosis and Main Criteria for Inclusion: The population for this study was healthy males and females between the ages of 18 and 55 years, inclusive, with a body mass index between 18 $kg/m^2$ and 30 $kg/m^2$, inclusive.

Investigational Product and Comparator Information:

CD24Fc: single dose of 10 mg, 30 mg, 60 mg, 120 mg, or 240 mg administered via IV infusion; lot number: 09MM-036. CD24Fc was a fully humanized fusion protein consisting of the mature sequence of human CD24 and the fragment crystallizable region of human immunoglobulin G1 (IgG1Fc). CD24Fc was supplied as a sterile, clear, colorless, preservative-free, aqueous solution for IV administration. CD24Fc was formulated as single dose injection solution, at a concentration of 10 mg/mL and a pH of 7.2. Each CD24Fc vial contained 160 mg of CD24Fc, 5.3 mg of sodium chloride, 32.6 mg of sodium phosphate dibasic heptahydrate, and 140 mg of sodium phosphate monobasic monohydrate in 16 mL ±0.2 mL of CD24Fc. CD24Fc was supplied in clear borosilicate glass vials with chlorobutyl rubber stoppers and aluminum flip-off seals.

Matching placebo (0.9% sodium chloride, saline) administered via IV infusion; lot numbers: P296855, P311852, P300715, P315952.

The intent-to-treat (ITT) Population consisted of all subjects who received at least 1 dose of the study drug. The ITT Population was the primary analysis population for subject information and safety evaluation.

Clinical laboratory evaluations (chemistry, hematology, and urinalysis) were summarized by treatment and visit. Change from baseline was also summarized. Vital signs (blood pressure, heart rate, respiratory rate, and temperature) were summarized by treatment and time point. Change from baseline was also summarized. All physical examination data were listed. Electrocardiogram parameters and the change from baseline were summarized. Overall interpretations were listed.

Plasma CD24Fc Concentration

Figure 16:
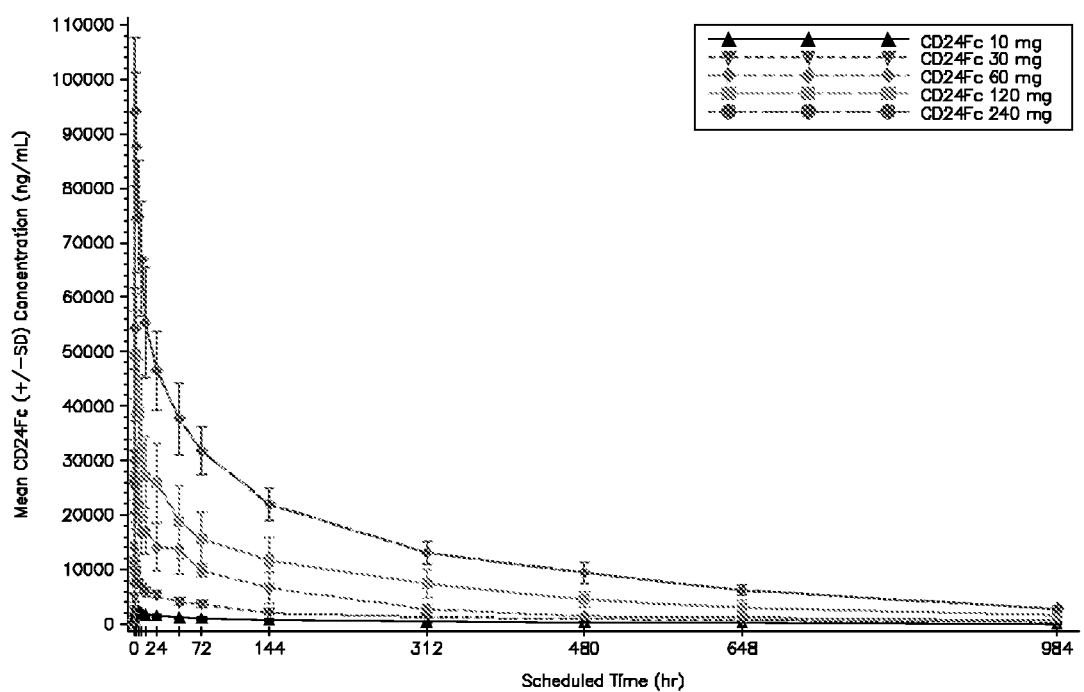
FIG. 16 shows a plot of mean plasma CD24Fc concentration (±SD) by treatment for a PK Evaluable Population in human subjects. PK=pharmacokinetic; SD=standard deviation.

As shown in FIG. 16, the mean plasma concentration of CD24Fc increased proportionally to the dose of CD24Fc administered. For all dose groups except 120 mg, the maximum mean plasma concentration of CD24Fc was reached at 1 hour post-dose. The maximum mean plasma concentration of CD24Fc for the 120 mg group was reached at 2 hours post-dose. By Day 42 (984 hours), the mean plasma concentration of CD24Fc for all groups had decreased to between 2% and 4% of the maximum mean plasma concentration.

Table 1 summarizes the plasma CD24Fc PK parameters by treatment for the PK Evaluable Population.

TABLE 1

Summary of Plasma CD24Fc Pharmacokinetic Parameters by Treatment - PK Evaluable Population

| Parameter Statistic | CD24Fc 10 mg (N = 6) | CD24Fc 30 mg (N = 6) | CD24Fc 60 mg (N = 6) | CD24Fc 120 mg (N = 6) | CD24Fc 240 mg (N = 6) |
|---|---|---|---|---|---|
| $C_{max}$ (ng/mL) | | | | | |
| n | 6 | 6 | 6 | 6 | 6 |
| Mean (SD) | 2495 (576) | 9735 (1715) | 30 083 (7179) | 52 435 (9910) | 95 865 (10 734) |
| CV % | 23.1 | 17.6 | 23.9 | 18.9 | 11.2 |
| Median | 2371 | 9218 | 29 026 | 50 401 | 93 206 |
| Min, Max | 1,967, 3,390 | 8,583, 13,086 | 22,557, 42,628 | 40,434, 65,704 | 81,296, 110,110 |
| Geometric mean | 2,442 | 9,625 | 29,424 | 51,666 | 95,365 |
| Geometric CV % | 22.8 | 16.1 | 23.0 | 19.0 | 11.2 |
| $AUC_{0-42\ d}$ (ng*hr/mL) | | | | | |
| n | 6 | 6 | 6 | 6 | 6 |
| Mean (SD) | 423,061 (99,615) | 1,282,430 (88,798) | 3,226,255 (702,862) | 6,541,501 (2,190,944) | 12,704,705 (1,918,596) |
| CV % | 23.5 | 6.9 | 21.8 | 33.5 | 15.1 |
| Median | 434,043 | 1,302,719 | 3,124,933 | 5,785,142 | 12,563,426 |
| Min, Max | 291,020, 528,079 | 1,175,733, 1,403,024 | 2,487,550, 4,139,748 | 4,485,193, 9,415,266 | 10,466,635, 15,693,606 |
| Geometric mean | 412,795 | 1,279,851 | 3,163,252 | 6,249,552 | 12,586,731 |
| Geometric CV % | 25.0 | 7.0 | 22.0 | 33.8 | 15.0 |
| $AUC_{0-inf}$ (ng*hr/mL) | | | | | |
| n | 6 | 6 | 6 | 6 | 6 |
| Mean (SD) | 462,260 (116,040) | 1,434,464 (131,316) | 3,497,196 (705,653) | 7,198,196 (2,458,320) | 13,861,796 (1,962,780) |
| CV % | 25.1 | 9.2 | 20.2 | 34.2 | 14.2 |
| Median | 470,426 | 1,422,205 | 3,519,732 | 6,463,665 | 13,713,034 |
| Min, Max | 310,956, 596,599 | 1,281,715, 1,650,503 | 2,703,655, 4,309,023 | 4,910,640, 10,479,940 | 11,822,988, 17,175,236 |
| Geometric mean | 449,583 | 1,429,578 | 3,437,036 | 6,862,129 | 13,750,972 |
| Geometric CV % | 26.7 | 9.0 | 20.7 | 34.6 | 13.8 |
| $T_{max}$ (hr) | | | | | |
| n | 6 | 6 | 6 | 6 | 6 |
| Mean (SD) | 1.15 (0.42) | 1.17 (0.41) | 1.01 (0.01) | 1.34 (0.51) | 1.33 (0.52) |
| CV % | 36.1 | 35.0 | 1.2 | 38.0 | 38.7 |
| Median | 1.00 | 1.00 | 1.00 | 1.03 | 1.00 |
| Min, Max | 0.92, 2.00 | 1.00, 2.00 | 1.00, 1.03 | 1.00, 2.00 | 1.00, 2.00 |
| t½ (hr) | | | | | |
| n | 6 | 6 | 6 | 6 | 6 |
| Mean (SD) | 280.83 (22.37) | 327.10 (41.32) | 279.82 (65.59) | 286.45 (23.38) | 285.33 (24.33) |
| CV % | 8.0 | 12.6 | 23.4 | 8.2 | 8.5 |
| Median | 279.61 | 317.23 | 264.69 | 290.76 | 287.74 |
| Min, Max | 258.87, 321.26 | 289.82, 394.24 | 210.18, 362.46 | 243.89, 309.26 | 249.24, 322.26 |
| AUCextr (%) | | | | | |
| n | 6 | 6 | 6 | 6 | 6 |
| Mean (SD) | 7.61 (2.14) | 10.44 (2.94) | 7.88 (4.26) | 8.92 (1.94) | 8.46 (1.99) |
| CV % | 28.1 | 28.2 | 54.0 | 21.8 | 23.5 |
| Median | 7.16 | 10.01 | 6.35 | 9.27 | 8.45 |
| Min, Max | 5.46, 11.47 | 7.10, 15.05 | 3.92, 14.48 | 5.49, 10.99 | 5.56, 11.50 |

TABLE 1-continued

Summary of Plasma CD24Fc Pharmacokinetic Parameters by Treatment - PK Evaluable Population

| Parameter Statistic | CD24Fc 10 mg (N = 6) | CD24Fc 30 mg (N = 6) | CD24Fc 60 mg (N = 6) | CD24Fc 120 mg (N = 6) | CD24Fc 240 mg (N = 6) |
|---|---|---|---|---|---|
| CL (L/hr) | | | | | |
| n | 6 | 6 | 6 | 6 | 6 |
| Mean (SD) | 0.0229 (0.0061) | 0.0211 (0.0019) | 0.0178 (0.0036) | 0.0183 (0.0058) | 0.0176 (0.0023) |
| CV % | 26.7 | 8.8 | 20.5 | 31.7 | 13.3 |
| Median | 0.0216 | 0.0211 | 0.0173 | 0.0191 | 0.0175 |
| Min, Max | 0.0168, 0.0322 | 0.0182, 0.0234 | 0.0139, 0.0222 | 0.0115, 0.0244 | 0.0140, 0.0203 |
| Vd (L) | | | | | |
| n | 6 | 6 | 6 | 6 | 6 |
| Mean (SD) | 9.153 (1.943) | 9.867 (0.804) | 7.289 (2.592) | 7.491 (2.202) | 7.276 (1.426) |
| CV % | 21.2 | 8.1 | 35.6 | 29.4 | 19.6 |
| Median | 8.507 | 10.007 | 7.486 | 7.691 | 7.151 |
| Min, Max | 7.326, 12.010 | 8.771, 10.958 | 4.222, 11.139 | 4.933, 9.974 | 5.814, 9.438 |

$AUC_{0-42\,d}$ = area under the concentration-time curve from time 0 to 42 days; $AUC_{0-inf}$ = area under the concentration-time curve extrapolated from time 0 to infinity; AUCextr = percentage of $AUC_{0-inf}$ that was due to extrapolation from the time of the last measurable concentration, per subject, to infinity; CL = total body clearance; $C_{max}$ = maximum observed plasma drug concentration; CV % = coefficient of variation; Min = minimum; Max = maximum; SD = standard deviation; $t^{1/2}$ = terminal elimination half-life; $T_{max}$ = time of maximum observed plasma drug concentration; Vd = volume of distribution.

Plasma CD24Fc Dose Proportionality Analysis

Figure 17:
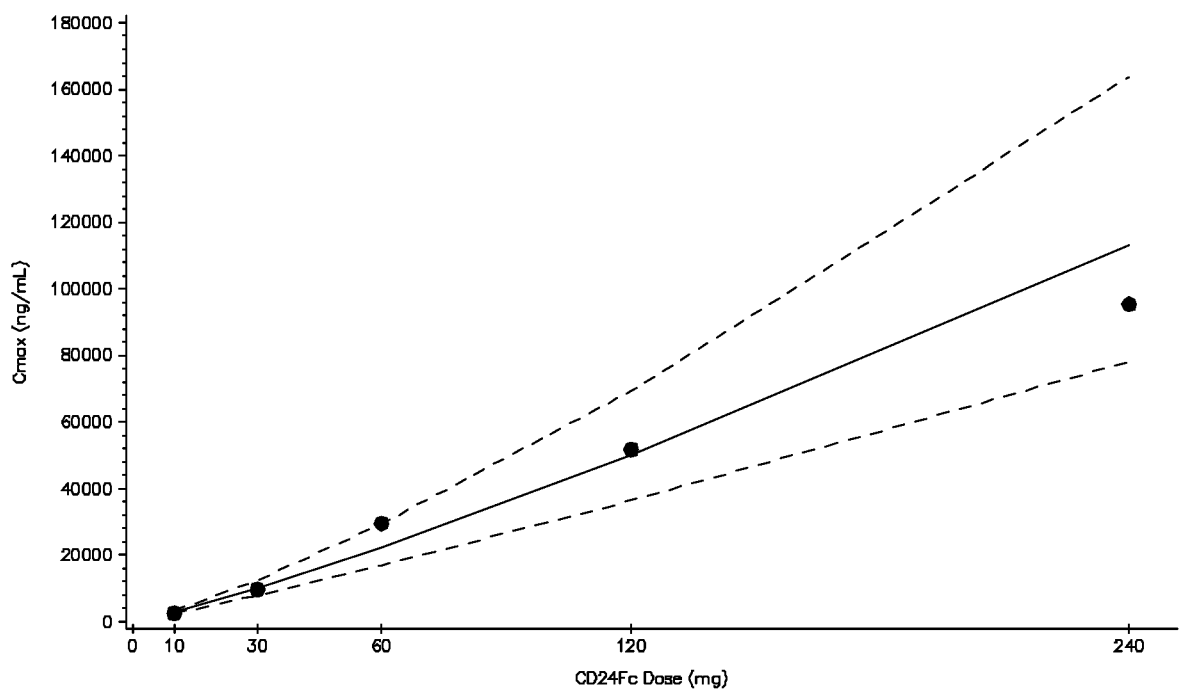
FIG. 17 shows a dose proportionality plot of CD24Fc $C_{max}$ versus dose for a PK Evaluable Population.
Figure 18:
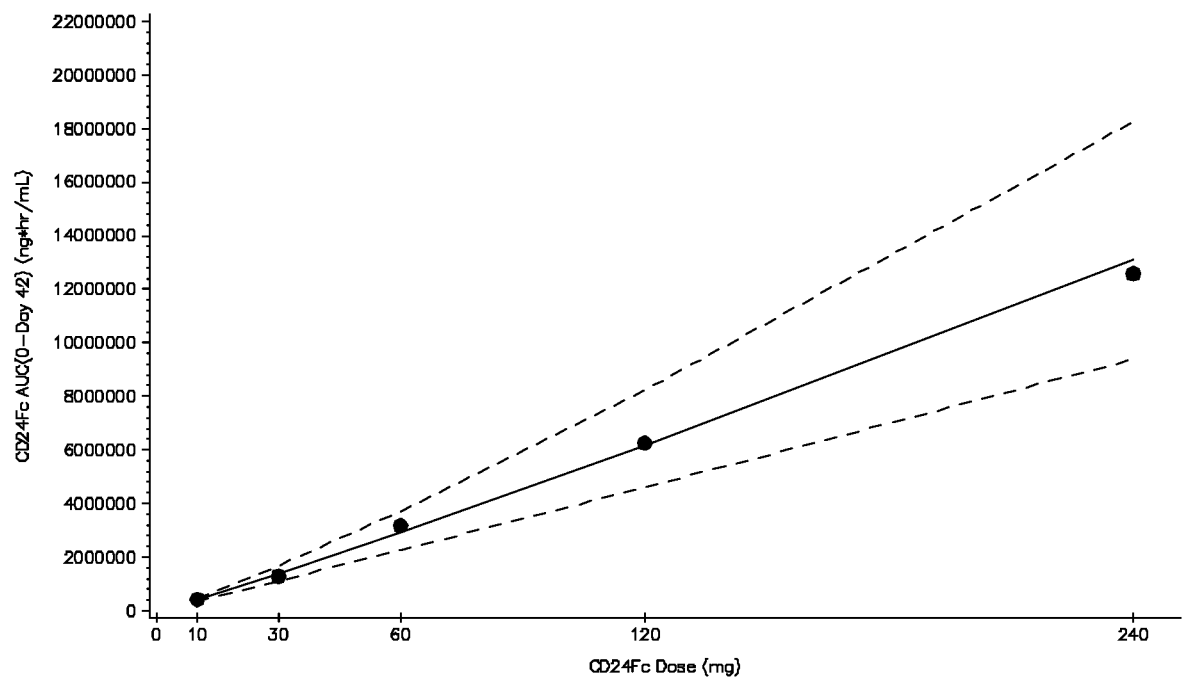
FIG. 18 shows a dose proportionality plot of CD24Fc $AUC_{0-42d}$ versus dose for a PK Evaluable Population.
Figure 19:
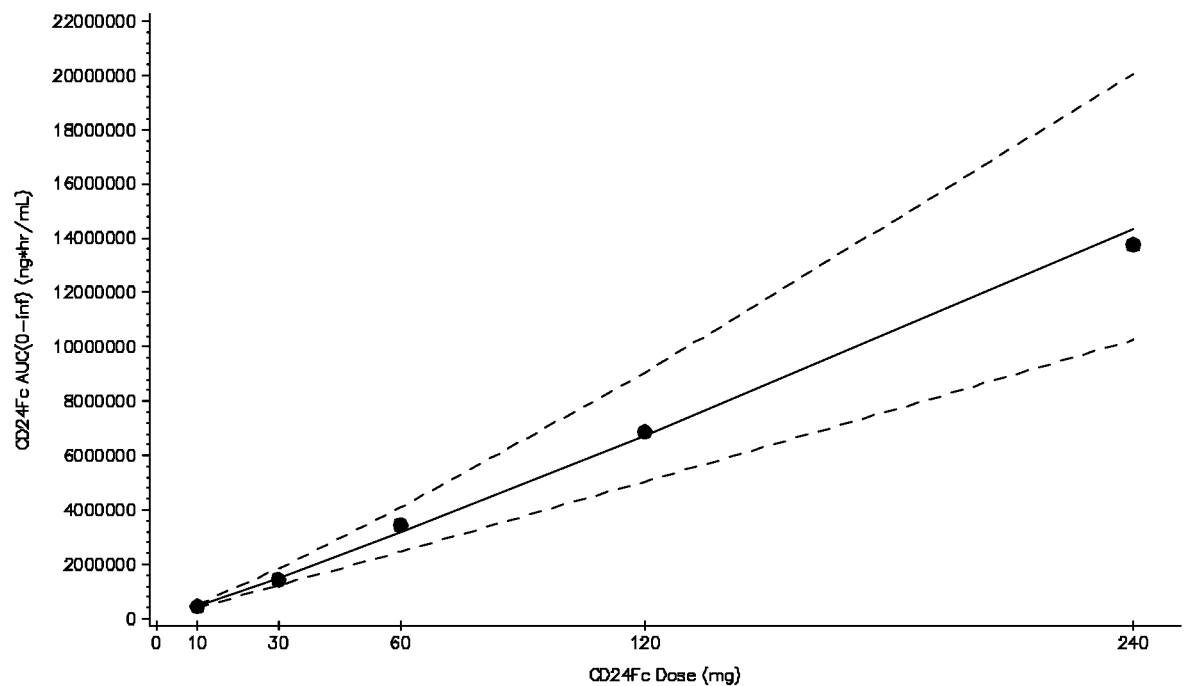
FIG. 19 shows a dose proportionality plot of CD24Fc $AUC_{0-inf}$ versus dose for a PK Evaluable Population.

FIG. 17 shows a dose proportionality plot of CD24Fc $C_{max}$ versus dose for the PK Evaluable Population. FIG. 18 shows a dose proportionality plot of CD24Fc $AUC_{0-42d}$ versus dose for the PK Evaluable Population. FIG. 19 shows a dose proportionality plot of CD24Fc $AUC_{0-inf}$ versus dose for the PK Evaluable Population. Table 2 shows a power analysis of dose proportionality.

TABLE 2

Power Analysis of Dose Proportionality: Plasma CD24Fc Pharmacokinetic Parameters - PK Evaluable Population

| Parameter Statistic | CD24Fc 10 mg (N = 6) | CD24Fc 30 mg (N = 6) | CD24Fc 60 mg (N = 6) | CD24Fc 120 mg (N = 6) | CD24Fc 240 mg (N = 6) | Dose Proportionality | | |
|---|---|---|---|---|---|---|---|---|
| | | | | | | Slope Estimate | Standard Error | 90% CI |
| $C_{max}$ (ng/mL) | | | | | | 1.172 | 0.040 | (1.105, 1.240) |
| Geometric mean | 2,441.8 | 9,624.9 | 29,424.4 | 51,666.4 | 95,364.9 | | | |
| Geometric CV % | 22.8 | 16.1 | 23.0 | 19.0 | 11.2 | | | |
| $AUC_{0-42\,d}$ (ng*hr/mL) | | | | | | 1.088 | 0.036 | (1.027, 1.148) |
| Geometric mean | 412,794.8 | 1,279,850.8 | 3,163,251.7 | 6,249,551.9 | 12,586,731.3 | | | |
| Geometric CV % | 25.0 | 7.0 | 22.0 | 33.8 | 15.0 | | | |
| $AUC_{0-inf}$ (ng*hr/mL) | | | | | | 1.087 | 0.036 | (1.026, 1.148) |
| Geometric mean | 449,583.5 | 1,429,577.5 | 3,437,035.6 | 6,862,128.7 | 13,750,972.4 | | | |
| Geometric CV % | 26.7 | 9.0 | 20.7 | 34.6 | 13.8 | | | |

Geometric CV % = $100*sqrt(exp(SD^2) - 1)$, where SD was the standard deviation of the log-transformed data. The power model was fitted by restricted maximum likelihood, regressing the log-transformed PK parameter on log transformed dose. Both the intercept and slope were fitted as fixed effects. Dose proportionality was not rejected if the 90% CI lies within (0.8, 1.25).
$AUC_{0-42\,d}$ = area under the concentration-time curve from time 0 to 42 days; $AUC_{0-inf}$ = area under the concentration-time curve extrapolated from time 0 to infinity; CI = confidence interval; $C_{max}$ = maximum observed plasma drug concentration; CV % = coefficient of variation; PK = pharmacokinetic; SD = standard deviation.

The $C_{max}$ slope estimate was 1.172 with a 90% CI of 1.105 to 1.240. The $AUC_{0-42d}$ slope estimate was 1.088 with a 90% CI of 1.027 to 1.148. The $AUC_{0-inf}$ slope estimate was 1.087 with a 90% CI of 1.026 to 1.1.

Pharmacokinetic Conclusions

The $C_{max}$ and AUCs of plasma CD24Fc increased proportionally to the doses administered in mouse, monkey and human. The plasma CD24Fc reached $T_{max}$ between 1.01 and 1.34 hours. The $t_{1/2}$ of plasma CD24Fc ranged between 280.83 and 327.10 hours.

EXAMPLE 5

CD24 Lowers LDL-C Levels

This example demonstrates that CD24Fc lowers LDL-C. Changes of fasting LDL-C in plasma from baseline were analyzed in the clinical study which is described in more detail above (see the Methods section of example 4). Fasting LDL-C levels were determined among samples obtained on Day −1, Day 7, and Day 42 for Cohort 1 (CD24Fc 10 mg group). Beginning with Cohort 2 (CD24Fc 30 mg group), this lipid sampling was expanded to include Day 14. The data are summarized in Table 3. Due to an incomplete dataset in Cohort 1, Cohorts 2-5 were used to analyze for dose-dependent reduction of LDL-C levels. A statistically significant dose-dependent reduction was observed (Table 3).

TABLE 3

Change in LDL-C levels on Day 7 (U1), Day 14 (U2) and Day 42 (U3) from baseline (U0, defined as 100%)

| Dose | Obs | Variable | Label | N | Mean | Std Dev | Minimum | Maximum |
|---|---|---|---|---|---|---|---|---|
| 10 mg | 6 | u0 | Baseline LDL | 6 | 100.0000000 | 0 | 100.0000000 | 100.0000000 |
| | | u1 | 7 days LDL ratio | 5 | 99.6785886 | 8.5665505 | 87.0370370 | 107.7586207 |
| | | u2 | 14 days LDL ratio | 0 | . | . | . | . |
| | | u3 | 42 days LDL ratio | 6 | 102.9957054 | 5.3134796 | 96.8085106 | 110.5769231 |
| 30 mg | 6 | u0 | Baseline LDL | 6 | 100.0000000 | 0 | 100.0000000 | 100.0000000 |
| | | u1 | 7 days LDL ratio | 6 | 96.9190313 | 9.5257894 | 86.9047619 | 113.4328358 |
| | | u2 | 14 days LDL ratio | 6 | 97.5816504 | 15.2482354 | 84.5238095 | 122.3880597 |
| | | u3 | 42 days LDL ratio | 6 | 106.1959745 | 8.2383407 | 95.2830189 | 113.4328358 |
| 60 mg | 6 | u0 | Baseline LDL | 6 | 100.0000000 | 0 | 100.0000000 | 100.0000000 |
| | | u1 | 7 days LDL ratio | 6 | 90.7620588 | 12.6697467 | 72.0720721 | 106.1728395 |
| | | u2 | 14 days LDL ratio | 6 | 102.5671170 | 5.2461286 | 96.5517241 | 110.3773585 |
| | | u3 | 42 days LDL ratio | 6 | 105.1546943 | 13.4340830 | 93.2773109 | 127.1604938 |
| 120 mg | 6 | u0 | Baseline LDL | 6 | 100.0000000 | 0 | 100.0000000 | 100.0000000 |
| | | u1 | 7 days LDL ratio | 6 | 87.1476632 | 16.0595374 | 61.7391304 | 106.4516129 |
| | | u2 | 14 days LDL ratio | 6 | 95.2625418 | 11.8341667 | 83.4782609 | 116.1290323 |
| | | u3 | 42 days LDL ratio | 6 | 100.1377165 | 9.9404474 | 87.1794872 | 112.3456790 |
| 240 mg | 6 | u0 | Baseline LDL | 6 | 100.0000000 | 0 | 100.0000000 | 100.0000000 |
| | | u1* | 7 days LDL ratio | 6 | 84.6472221 | 7.6553896 | 71.5596330 | 94.0476190 |
| | | u2* | 14 days LDL ratio | 5 | 90.1393086 | 5.2501807 | 86.2385321 | 99.0825688 |
| | | u3 | 42 days LDL ratio | 6 | 107.0369419 | 14.7154796 | 79.8449612 | 121.1009174 |
| Control | 10 | u0 | Baseline LDL | 10 | 100.0000000 | 0 | 100.0000000 | 100.0000000 |
| | | u1 | 7 days LDL ratio | 10 | 93.7350811 | 8.9747121 | 83.7837838 | 107.1428571 |
| | | u2 | 14 days LDL ratio | 8 | 104.5965396 | 13.8625952 | 83.7837838 | 125.2631579 |
| | | u3 | 42 days LDL ratio | 10 | 102.6699920 | 16.2815599 | 77.0270270 | 138.1578947 |

*P < 0.05 when compared to placebo group, student t-test.

Using cohort 1 as reference, it was determined whether CD24Fc reduced LDL-C levels in a dose- and time-dependent manner. As shown in Table 4, compared with cohort 1 which received 10 mg of CD24Fc, a significant dose-dependent reduction of LDL-C levels was observed ($p<0.0001$).

TABLE 4

Dose and time-dependence of LDL-C reduction in Cohorts by GEE model, using cohort 1 (the lowest dose as reference)

| Parameter | Estimate | Standard Error | 95% Confidence Limits | | Z | Pr > |Z| |
|---|---|---|---|---|---|---|
| Intercept | 98.0544 | 5.4745 | 87.3245 | 108.7842 | 17.91 | <.0001 |
| time | 1.6471 | 2.1861 | −2.6375 | 5.9317 | 0.75 | 0.4512 |
| 30 mg | 3.7167 | 7.3244 | −10.6389 | 18.0722 | 0.51 | 0.6118 |
| time*30 mg | −1.4733 | 3.5435 | −8.4183 | 5.4718 | −0.42 | 0.6776 |
| 60 mg | −25.4898 | 14.4124 | −53.7377 | 2.7581 | −1.77 | 0.0770 |
| time* 60 mg | 10.7245 | 5.0225 | 0.8805 | 20.5685 | 2.14 | 0.0327 |
| 120 mg | −21.2684 | 9.4771 | −39.8431 | −2.6936 | −2.24 | 0.0248 |
| time* 120 mg | 6.6669 | 3.9357 | −1.0468 | 14.3806 | 1.69 | 0.0903 |
| 240 mg | −15.8681 | 6.9247 | −29.4402 | −2.2960 | −2.29 | 0.0219 |
| time*240 mg | 5.4390 | 2.8825 | −0.2106 | 11.0887 | 1.89 | 0.0592 |

Figure 20:
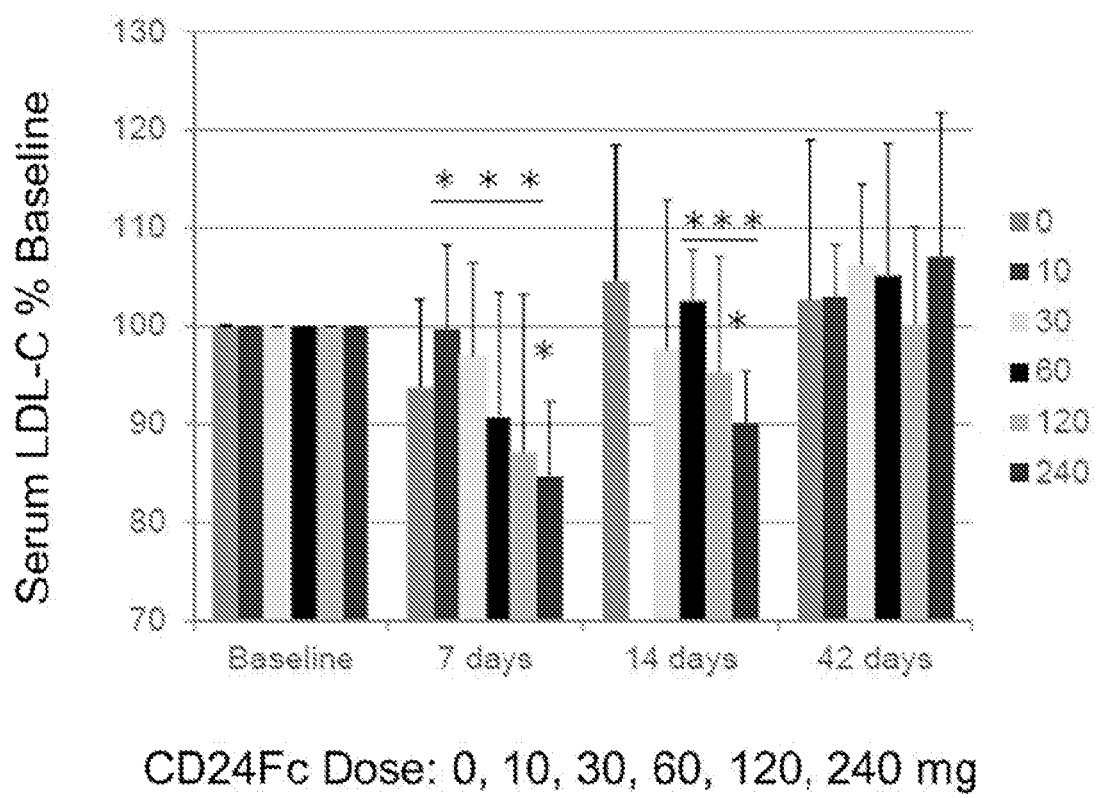
FIG. 20 shows the decrease human serum LDL-C following CD24Fc treatment expressed as a percentage of baseline levels. Using cohort 1 as reference, which received 10 mg of CD24Fc, it was determined whether CD24Fc reduced LDL-C levels in a dose- and time-dependent manner. A significant dose-dependent reduction of LDL-C levels was observed (p<0.0001).

This demonstrates that CD24Fc is effective for lowering LDL-C in human patients. This data is displayed graphically in FIG. 20.

EXAMPLE 6

CD24 Lowers Leptin Levels

This example demonstrates that CD24Fc increases circulating leptin levels. Changes of leptin in plasma from baseline were analyzed in the clinical study which is described in more detail above (see the Methods section of example 4)

Using a Luminex bead-based immunoassay, plasma leptin levels were determined in 80 samples obtained on Day −1 pre-treatment and Day 3-post treatment from 40 healthy subjects receiving CD24Fc or placebo. The data are summarized in Table 5.

TABLE 5

Leptin levels in subject plasma.

| Subject # | Cohort | Sample Day | Replicate 1: Leptin, pg/ml | Replicate 2: Leptin, pg/ml | Average: Leptin, pg/ml |
|---|---|---|---|---|---|
| 002 | Placebo | Day-1 | 2057.5 | 2151.1 | 2104.3 |
| 002 | Placebo | Day 3 | 3101.0 | 2603.7 | 2852.4 |
| 003 | 10 mg | Day-1 | 8764.2 | 7524.7 | 8144.4 |
| 003 | 10 mg | Day 3 | 10738.8 | 9318.1 | 10028.4 |
| 006 | 10 mg | Day-1 | 3205.3 | 3461.2 | 3333.2 |
| 006 | 10 mg | Day 3 | 4919.7 | 5651.1 | 5285.4 |
| 009 | 10 mg | Day-1 | 26019.6 | 33582.9 | 29801.2 |
| 009 | 10 mg | Day 3 | 25430.8 | 26998.1 | 26214.4 |
| 010 | 10 mg | Day-1 | 3657.9 | 3961.1 | 3809.5 |
| 010 | 10 mg | Day 3 | 4705.2 | 5613.2 | 5159.2 |
| 008 | 10 mg | Day-1 | 4055.9 | 4856.4 | 4456.2 |
| 008 | 10 mg | Day 3 | 11582.4 | 14660.8 | 13121.6 |
| 012 | Placebo | Day-1 | 12345.2 | 14724.4 | 13534.8 |
| 012 | Placebo | Day 3 | 14293.5 | 17111.0 | 15702.3 |
| 016 | 10 mg | Day-1 | 5281.3 | 6345.6 | 5813.4 |
| 016 | 10 mg | Day 3 | 5562.1 | 5491.4 | 5526.7 |
| 033 | 30 mg | Day-1 | 7906.4 | 8295.2 | 8100.8 |
| 033 | 30 mg | Day 3 | 15080.8 | 15884.3 | 15482.5 |
| 042 | Placebo | Day-1 | 3795.8 | 4013.6 | 3904.7 |
| 042 | Placebo | Day 3 | 4153.9 | 4767.0 | 4460.4 |
| 047 | 30 mg | Day-1 | 11751.1 | 13536.1 | 12643.6 |
| 047 | 30 mg | Day 3 | 14161.9 | 16374.2 | 15268.1 |
| 052 | Placebo | Day-1 | 4022.3 | 4668.0 | 4345.2 |
| 052 | Placebo | Day 3 | 5699.2 | 6002.9 | 5851.0 |
| 060 | 30 mg | Day-1 | 13672.4 | 16908.8 | 15290.6 |
| 060 | 30 mg | Day 3 | 18703.5 | 19928.7 | 19316.1 |
| 063 | 30 mg | Day-1 | 6375.7 | 7636.9 | 7006.3 |
| 063 | 30 mg | Day 3 | 8173.2 | 9556.2 | 8864.7 |
| 066 | 30 mg | Day-1 | 15790.3 | 17753.7 | 16772.0 |
| 066 | 30 mg | Day 3 | 24460.6 | 27606.1 | 26033.3 |
| 067 | 30 mg | Day-1 | 2141.7 | 1618.8 | 1880.2 |
| 067 | 30 mg | Day 3 | 1908.2 | 1721.9 | 1815.0 |
| 088 | Placebo | Day-1 | 2389.5 | 1932.3 | 2160.9 |
| 088 | Placebo | Day 3 | 2273.8 | 2305.3 | 2289.6 |
| 090 | 60 mg | Day-1 | 4883.8 | 4147.8 | 4515.8 |
| 090 | 60 mg | Day 3 | 4884.7 | 4864.1 | 4874.4 |
| 096 | 60 mg | Day-1 | 6991.8 | 6135.6 | 6563.7 |
| 096 | 60 mg | Day 3 | 9448.9 | 8672.7 | 9060.8 |
| 105 | 60 mg | Day-1 | 21867.1 | 20502.8 | 21185.0 |
| 105 | 60 mg | Day 3 | 27647.6 | 28394.9 | 28021.2 |
| 124 | Placebo | Day-1 | 787.0 | 811.4 | 799.2 |
| 124 | Placebo | Day 3 | 1038.7 | 1140.8 | 1089.8 |
| 129 | 60 mg | Day-1 | 10978.2 | 12103.2 | 11540.7 |
| 129 | 60 mg | Day 3 | 12475.3 | 15487.5 | 13981.4 |
| 130 | 60 mg | Day-1 | 10948.9 | 13845.4 | 12397.2 |
| 130 | 60 mg | Day 3 | 14237.8 | 18069.0 | 16153.4 |
| 131 | 60 mg | Day-1 | 7087.5 | 9026.8 | 8057.1 |
| 131 | 60 mg | Day 3 | 7537.5 | 9046.6 | 8292.1 |
| 134 | 120 mg | Day-1 | 27893.0 | 31498.7 | 29695.9 |
| 134 | 120 mg | Day 3 | 38629.1 | 43787.4 | 41208.2 |
| 149 | Placebo | Day-1 | 494.4 | 386.1 | 440.3 |
| 149 | Placebo | Day 3 | 740.8 | 650.8 | 695.8 |
| 143 | Placebo | Day-1 | 11114.0 | 9806.6 | 10460.3 |
| 143 | Placebo | Day 3 | 13506.2 | 10982.0 | 12244.1 |
| 147 | 120 mg | Day-1 | 7143.4 | 5834.3 | 6488.8 |
| 147 | 120 mg | Day 3 | 10558.2 | 8223.6 | 9390.9 |
| 148 | 120 mg | Day-1 | 1830.8 | 1432.5 | 1631.7 |
| 148 | 120 mg | Day 3 | 2193.1 | 1930.4 | 2061.7 |
| 157 | 120 mg | Day-1 | 884.3 | 781.7 | 833.0 |
| 157 | 120 mg | Day 3 | 1224.7 | 1087.3 | 1156.0 |
| 161 | 120 mg | Day-1 | 6576.9 | 5863.6 | 6220.3 |
| 161 | 120 mg | Day 3 | 8689.1 | 7117.7 | 7903.4 |
| 171 | 120 mg | Day-1 | 2899.6 | 2606.4 | 2753.0 |
| 171 | 120 mg | Day 3 | 2872.4 | 2592.9 | 2732.6 |
| 181 | Placebo | Day-1 | 2433.6 | 2206.1 | 2319.8 |
| 181 | Placebo | Day 3 | 2384.8 | 2171.0 | 2277.9 |
| 212 | Placebo | Day-1 | 6780.4 | 6600.6 | 6690.5 |
| 212 | Placebo | Day 3 | 10183.2 | 9953.6 | 10068.4 |
| 179 | 240 mg | Day-1 | 19575.6 | 20203.2 | 19889.4 |
| 179 | 240 mg | Day 3 | 29443.7 | 30264.3 | 29854.0 |
| 213 | 240 mg | Day-1 | 19.4 | 19.9 | 19.7 |
| 213 | 240 mg | Day 3 | 31.0 | 31.6 | 31.3 |
| 216 | 240 mg | Day-1 | 321.2 | 326.1 | 323.7 |
| 216 | 240 mg | Day 3 | 448.1 | 453.2 | 450.6 |
| 211 | 240 mg | Day-1 | 811.7 | 817.6 | 814.7 |
| 211 | 240 mg | Day 3 | 1883.2 | 1889.4 | 1886.3 |
| 214 | 240 mg | Day-1 | 888.5 | 887.8 | 888.1 |
| 214 | 240 mg | Day 3 | 981.2 | 976.5 | 978.9 |
| 218 | 240 mg | Day-1 | 900.6 | 892.7 | 896.6 |
| 218 | 240 mg | Day 3 | 1831.2 | 1808.1 | 1819.7 |

The analytical sensitivity or limit of detection (LOD) was determined as the value calculated from the standard curve at the point lying 2 standard deviations above the mean background (twenty zero standard replicates). The lower limit of quantification (LLOQ) was determined using a 2-fold dilution series of the standards in standard diluent assayed in triplicate over three different rounds, and is defined as the point at which the coefficient of variation (CV) for the measurement was 30%. The CV was calculated and plotted against concentration, and LLOQ was interpolated from the plot. The assay performance characteristics are as follow in Table 6.

TABLE 6

| Analyte | Leptin |
|---|---|
| Unit | pg/ml |
| LOD | 8.1 |
| LLOQ | 18.2 |
| Standard Curve Range | 7.7-600,000 |

Figure 21:
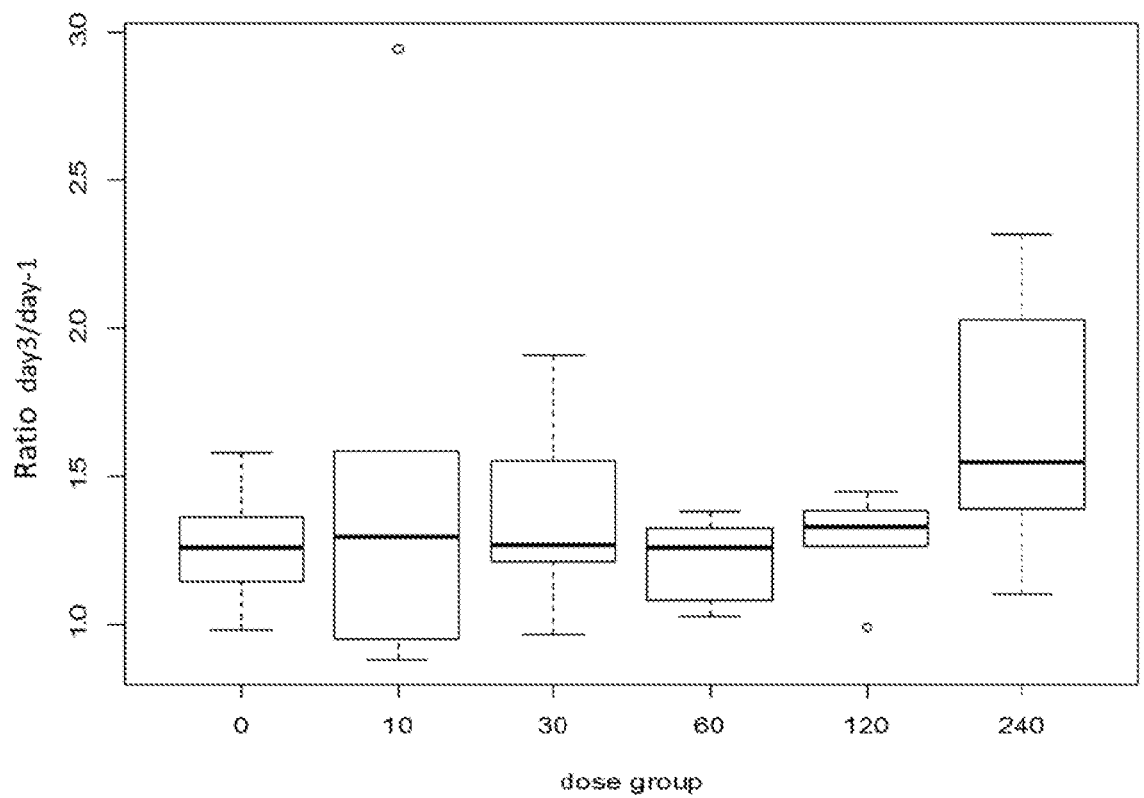
FIG. 21 shows the ratio of leptin in the serum of healthy human subjects at day 3 post CD24Fc treatment compared to day −1 pre-treatment. The drug was administered on day 0. The data is represented by CD24Fc dosing cohort; the 0 mg/kg group represents the placebo control group.

FIG. 21 displays the ratio of leptin on day3/day-1 for patients grouped by dosing cohort. As the figure shows, there is a upward trend in the relative amount circulating leptin following CD24Fc treatment and between the 0, 60, 120 and 240 mg cohorts this increase is statistically significant (P=0.009397, dose-dependent general linear model regression), demonstrating a dose dependent increase above 60 mg. Furthermore, there is a statistically significant increase in the level of leptin following CD24Fc administration in the 240 mg cohort compared to placebo (0 mg) (P=0.05 as determined by Student's T test), indicating that CD24Fc is effective for increasing leptin in human patients.

EXAMPLE 7

Assessment of the Efficacy of CD24 Proteins in Mouse Models of SLE

Twenty four (24) MRL/MpJ-Faslpr/J (JAX stock#000485) (MRL.lpr) female mice 8 weeks of age were transferred an in vivo research vivarium in Bar Harbor, Me. The mice were ear notched for identification and housed in individually and positively ventilated polysulfonate cages with HEPA filtered air at a density of 5 mice per cage. The animal room was lighted entirely with artificial fluorescent lighting, with a controlled 12 h light/dark cycle (6 am to 6 pm light). The normal temperature and relative humidity ranges in the animal rooms were 22±4° C. and 50±15%, respectively. The animal rooms were set to have 15 air exchanges per hour. Filtered tap water, acidified to a pH of 2.5 to 3.0, and normal rodent chow were provided ad libitum.

At 11 weeks of age, proteinuria was tested using Albustix. Mice producing a score of 1 were randomized into two groups of 10. Group 1 received a single IP injection of 200 µl of 1×PBS. Group 2 received a single IP injection of 200 µl of 10 mg/ml hCD24-Fc. Proteinuria was measured weekly until study terminus. At 16 weeks of age, mice were euthanized. Their spleens were weighed and processed for mononuclear cells. Lymph nodes (axillary, brachial, inguinal) were combined, and weights recorded.

Figure 22:
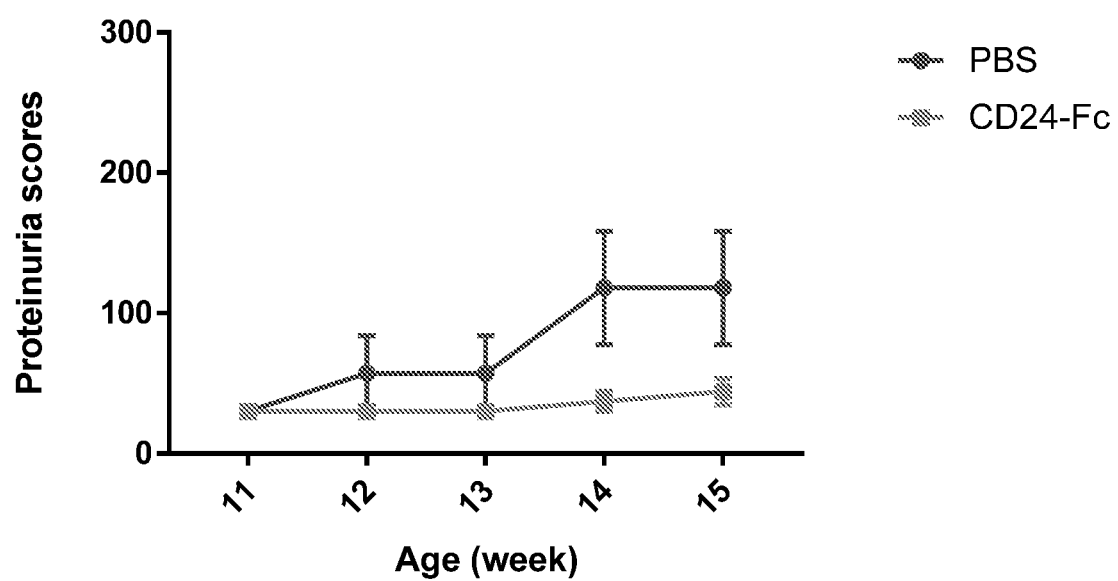
FIG. 22 shows that CD24Fc treatment prevents progression of proteinuria in a MRL.lpr lupus model. Data shown are means and SEM of urine protein levels as measured by Albustix (n=10).

Protein levels in urine were measured weekly using Albustix beginning at 11 weeks of age. The protein levels were assigned as follows. 1+, 30 mg/dL; 2+, 100 mg/dL; 3+, 300 mg/dL. As shown in FIG. 22, mice that received PBS show progressive increase of proteinuria over the next 4 weeks, while those that received CD24Fc showed minimal increases.

Figure 23:
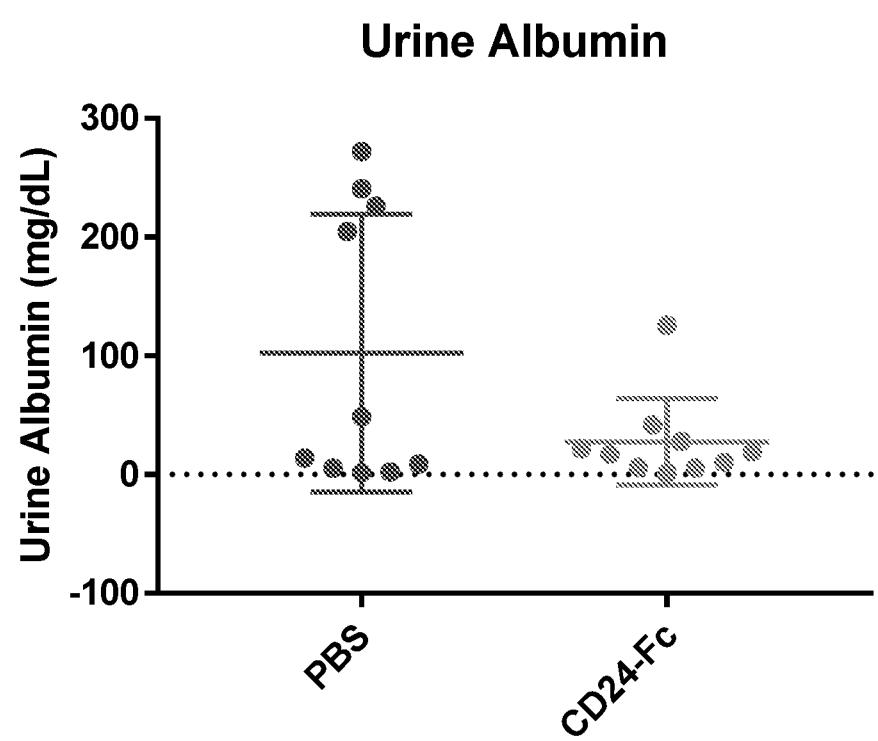
FIG. 23 shows that a single injection of CD24Fc reduces proteinuria in MRL.lpr mice. Female MRL.lpr mice with matched levels of proteinuria at 11 weeks old received a single injection of either PBS (vehicle control) or 200 μg/mouse of CD24Fc intraperitoneally at 12 weeks. Urine albumin levels were measured at week 16 Siemens AU680 chemistry analyzer. P=0.03, one-tailed unpaired t test. N=10.

To more accurately measure proteinuria, mice were tested for urine albumin using the Siemens AU680 chemistry analyzer at 16 weeks of age. As shown in FIG. 23, CD24Fc treatment significantly reduced proteinuria. Taken together, these data demonstrated that CD24Fc prevented progression of proteinuria in the model.

Figure 24:
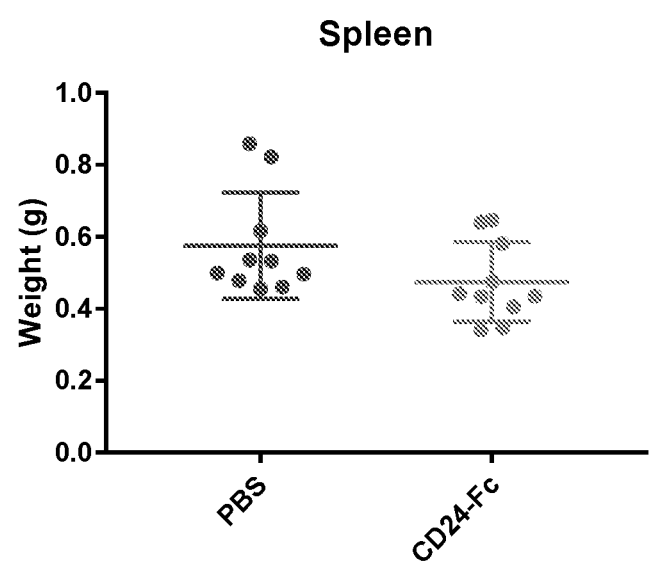
FIG. 24 shows that a single injection of CD24Fc reduces splenomegaly in the MRL.lpr mice. Female MRL.lpr mice with matched levels of proteinuria at 11 weeks old received a single injection of either PBS (vehicle control) or 200 μg/mouse of CD24Fc intraperitoneally at 12 weeks. Mice were euthanized at week 16, and their spleens were weighted. P=0.05, one-tailed unpaired t test. N=10.
Figure 25:
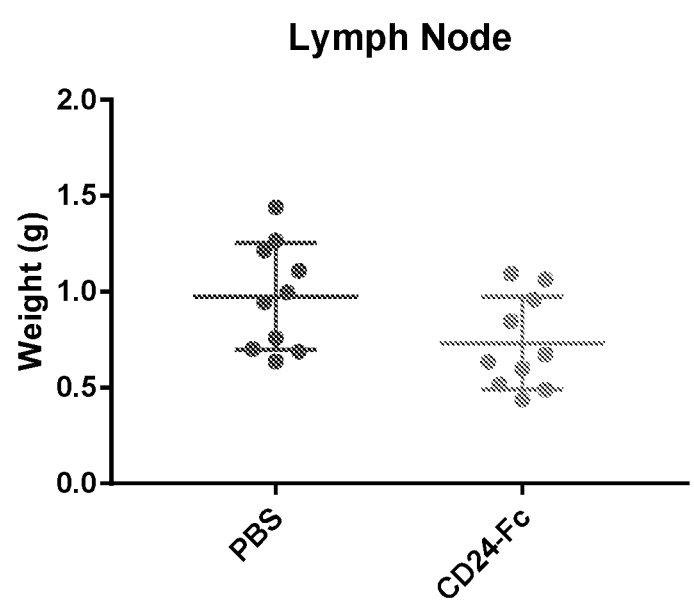
FIG. 25 shows that a single injection of CD24Fc reduces lymphadenopathy in the MRL.lpr mice. Female MRL.lpr mice with matched levels of proteinuria at 11 weeks old received a single injection of either PBS (vehicle control) or 200 μg/mouse of CD24Fc intraperitoneally at 12 weeks. Mice were euthanized at week 16, and their lymph nodes (axillary, brachial, inguinal) were combined and weighted. P=0.03, one-tailed unpaired t test. N=10.

Splenomegaly and lymphadenopathy are major characteristics of the MRL.lpr lupus model. To substantiate the therapeutic effect, the ability of CD24Fc to reduce the weight of spleen and lymph nodes was tested. As shown in FIGS. 24 and 25, CD24Fc significantly reduced the weight of spleen and lymph nodes, respectively, when measured at 16 weeks.

Taken together, the data with the murine lupus model demonstrate the efficacy of CD24Fc for treating SLE.

EXAMPLE 8

Clinical Trial for the Treatment of Lupus Nephritis

Described below is the outline of a Phase I clinical trial to assess the use of CD24Fc in the treatment of lupus nephritis.
Objectives:
Primary Objectives:
To evaluate the safety and tolerability of multi-dose CD24Fc plus SOC in subjects with lupus nephritis refractory to standard of care treatment immunosuppressive medications
To define the recommended Phase 2 dose (RP2D) and/or maximum tolerated dose (MTD) of CD24Fc in the target population.
Secondary Objectives:
To assess the pharmacokinetic (PK) profile of multi-dose CD24Fc
To assess efficacy of CD24Fc when added to standard of care therapy for lupus nephritis
To evaluate exploratory pharmacodynamic biomarkers for clinical response
Study Population:
Patients with active/proliferative lupus nephritis refractory to standard of care immunosuppressive medications with moderate background therapy/SOC (high dose steroids plus MMF or cyclophosphamide)
Inclusion Criteria:
Age ≥18 years;
A diagnosis of SLE according to the revised American College of Rheumatology criteria;
Active disease (SELENA-SLEDAI score ≥6) at screening
Proliferative disease (class III/IV)
Seropositivity as defined by 2 positive ANA or anti-dsDNA test results (ANA titers ≥1:80 and/or anti-dsDNA antibodies ≥30 IU/mL), of which ≥1 test result had to be obtained during screening.
Elevated proteinuria
Exclusion Criteria:
Patients with >50% glomerular sclerosis or interstitial fibrosis or an estimated glomerular filtration rate (eGFR) of <25 ml/minute/1.73 m$^2$
Study Design:
A multi-center randomized double-blind multi-dose study and will assess safety, tolerability, PK and biological activity of repeat doses of CD24Fc plus SOC vs placebo plus SOC in patients with proliferative refractory lupus nephritis. Patients will receive CD24Fc on days 1, 14, 28 and 42. CD24Fc will be administered by IV infusion.

The Dose-Escalation phase will comprise 3 different dosing cohorts of 10 patients (8:2 treatment:placebo) for a total enrollment of 30 patients. The dose levels for the Dose-Escalation phase have been determined based on results of the nonclinical Good Laboratory Practice (GLP) repeat-dose toxicology studies, relevant nonclinical pharmacodynamic readouts and based on the safety, PK and PD results from a single dose FIH study and a Phase II study in GvHD prophylaxis.
Cohort 1: 240 mg CD24Fc
Cohort 2: 480 mg CD24Fc
Cohort 3: 960 mg CD24Fc
The primary safety end-point for dose escalation will be the incidence of grade 3 (severe) or 4 (life-threatening) adverse events (AEs). Dose escalation will be allowed if <2 patients in a cohort experienced a grade 3 or 4 AE within 2 half-lives of the last dosing day.

Clinical activity, biological activity and a range of potential PD markers based on the CD24Fc MOA will be evaluated throughout the study. Patients will be followed for 78 weeks.
Clinical Samples:
Blood draws will be required from all subjects at pre-dose and at multiple post-dose time points during treatment for assessment of safety, PK, and PD markers.
Study Assessments:
Safety:
Adverse events
Laboratory abnormalities
Infections
Mortality
Malignancy Clinical Activity:
- SLE responder index (SRI)—improvement in the Systemic Lupus Erythematosus Responder Index (SRI) at week 52 (reduction ≥4 points in SELENA-SLEDAI score; no new British Isles Lupus Assessment Group [BILAG] A organ domain score and no more than 1 new B organ domain score; and no worsening [<0.3 increase] in Physician's Global Assessment [PGA] score) versus baseline.)
- BICLA (BILAG based combined lupus assessment)
- Renal parameters—decrease in daily proteinuria, eGFR
- 6 month remission rate
- Steroid sparing (reduction in steroid dosage)—percentage of patients with a mean prednisone dose that was decreased ≥25% from baseline and was ≤7.5 mg/d during weeks 40 to 52
- Decrease in severe flares (modified SLE flare index, or BILAG A)

Pharmacokinetics:

PK will be determined by assessing serum levels of CD24Fc at various time points following the end of infusion (EOI).

Pharmacodynamics:
- Blood samples will be collected throughout the study for evaluation of potential biomarkers including changes in fasting low-density lipoprotein cholesterol (LDL-C) levels.
- Normalized lipid profile
- Anti-dsDNA
- ANA
- Complement levels (C3 and C4)
- B and T cell subsets
- Urine protein/creatine
- IFN signature
- IL-6

Statistical Analysis:

Safety:

The safety and tolerability of a rising intravenous multi-dose of CD24Fc in subjects will be evaluated by tabulating adverse events and by clinical assessment of laboratory data.

Pharmacokinetics:

The PK parameters include AUC 0-t, AUC0-inf, Cmax, Tmax, t½, Kel, Volume of distribution (Vd), Clearance (CL). The area under the plasma drug concentration-time curve from 0 to t ($AUC_{0-t}$), area under the plasma drug concentration-time curve from 0 to infinity ($AUC_{0-\infty}$), and maximum plasma concentration ($C_{max}$) will be log-transformed for all statistical analyses, and summary statistics will be back-transformed and presented on the original scale. Dose proportionality will be analyzed using $AUC_{0\infty}$ and $C_{max}$ across dose ranges.

REFERENCES

1. Munoz LE, Janko C, Schulze C, Schorn C, Sarter K, Schett G, Herrmann M. Autoimmunity and chronic inflammation—two clearance-related steps in the etiopathogenesis of SLE. Autoimmun Rev. 2010; 10(1): 38-42. Epub 2010/09/08. doi: 10.1016/j.autrev.2010.08.015. PubMed PMID: 20817127.
2. Urbonaviciute V, Furnrohr BG, Meister S, Munoz L, Heyder P, De Marchis F, Bianchi M E, Kirschning C, Wagner H, Manfredi AA, Kalden JR, Schett G, Rovere-Querini P, Herrmann M, Voll RE. Induction of inflammatory and immune responses by HMGB1-nucleosome complexes: implications for the pathogenesis of SLE. J Exp Med. 2008; 205(13):3007-18. PubMed PMID: 19064698.
3. Wen Z, Xu L, Chen X, Xu W, Yin Z, Gao X, Xiong S. Autoantibody induction by DNA-containing immune complexes requires HMGB1 with the TLR2/microRNA-155 pathway. Journal of Immunology. 2013; 190(11): 5411-22. Epub 2013/04/26. doi: 10.4049/jimmunol.1203301. PubMed PMID: 23616573.
4. Andersson U, Harris HE. The role of HMGB1 in the pathogenesis of rheumatic disease. Biochim Biophys Acta. 1799(1-2):141-8. PubMed PMID: 20123076.
5. Ostberg T, Kawane K, Nagata S, Yang H, Chavan S, Klevenvall L, Bianchi M, Harris HE, Andersson U, Palmblad K. Protective targeting of HMGB1 in a spontaneous arthritis model. Arthritis Rheum. 2010; 62:2963-72. PubMed PMID: 20533288.
6. Rice J W, Veal J M, Fadden RP, Barabasz A F, Partridge JM, Barta TE, Dubois LG, Huang KH, Mabbett SR, Silinski M A, Steed PM, Hall SE. Small molecule inhibitors of Hsp90 potently affect inflammatory disease pathways and exhibit activity in models of rheumatoid arthritis. Arthritis Rheum. 2008; 58(12):3765-75. PubMed PMID: 19035474.
7. Ahrens S, Zelenay S, Sancho D, Hanc P, Kjaer S, Feest C, Fletcher G, Durkin C, Postigo A, Skehel M, Batista F, Thompson B, Way M, Reis e Sousa C, Schulz O. F-actin is an evolutionarily conserved damage-associated molecular pattern recognized by DNGR-1, a receptor for dead cells. Immunity. 2012; 36(4):635-45. Epub 2012/04/10. doi: S1074-7613(12)00126-4 [pii] 10.1016/j.immuni.2012.03.008. PubMed PMID: 22483800.
8. Yamasaki S, Ishikawa E, Sakuma M, Hara H, Ogata K, Saito T. Mincle is an ITAM-coupled activating receptor that senses damaged cells. Nat Immunol. 2008; 9(10): 1179-88. Epub 2008/09/09. doi: ni.1651 [pii] 10.1038/ni.1651. PubMed PMID: 18776906.
9. Cavassani K A, Ishii M, Wen H, Schaller M A, Lincoln PM, Lukacs NW, Hogaboam CM, Kunkel SL. TLR3 is an endogenous sensor of tissue necrosis during acute inflammatory events. Journal of Experimental Medicine. 2008; 205(11):2609-21. PubMed PMID: 18838547.
10. Ivanov S, Dragoi AM, Wang X, Dallacosta C, Louten J, Musco G, Sitia G, Yap GS, Wan Y, Biron C A, Bianchi M E, Wang H, Chu WM. A novel role for HMGB1 in TLR9-mediated inflammatory responses to CpG-DNA. Blood. 2007; 110(6):1970-81. Epub 2007/06/06. doi: blood-2006-09-044776 [pii] 10.1182/blood-2006-09-044776. PubMed PMID: 17548579; PMCID: 1976374.
11. Sims GP, Rowe DC, Rietdijk ST, Herbst R, Coyle AJ. HMGB1 and RAGE in inflammation and cancer. Annu Rev Immunol.28:367-88. PubMed PMID: 20192808.
12. van Beijnum JR, Buurman W A, Griffioen A W. Convergence and amplification of toll-like receptor (TLR) and receptor for advanced glycation end products (RAGE) signaling pathways via high mobility group B1 (HMGB1). Angiogenesis. 2008; 11(1):91-9. PubMed PMID: 18264787.
13. Warger T, Hilf N, Rechtsteiner G, Haselmayer P, Carrick DM, Jonuleit H, von Landenberg P, Rammensee HG, Nicchitta CV, Radsak MP, Schild H. Interaction of TLR2 and TLR4 ligands with the N-terminal domain of Gp96 amplifies innate and adaptive immune responses. The Journal of biological chemistry. 2006; 281(32):22545-53. PubMed PMID: 16754684.
14. Zhang Q, Raoof M, Chen Y, Sumi Y, Sursal T, Junger W, Brohi K, Itagaki K, Hauser CJ. Circulating mitochondrial DAMPs cause inflammatory responses to injury. Nature. 2010; 464(7285):104-7. Epub 2010/03/06. doi: nature08780 [pii] 10.1038/nature08780. PubMed PMID: 20203610; PMCID: 2843437.
15. Chen GY, Tang J, Zheng P, Liu Y. CD24 and Siglec-10 selectively repress tissue damage-induced immune responses. Science. 2009; 323(5922):1722-5. doi: 10.1126/science.1168988. PubMed PMID: 19264983; PMCID: PMC2765686.
16. Chen GY, Chen X, King S, Cavassani K A, Cheng J, Zheng X, Cao H, Yu H, Qu J, Fang D, Wu W, Bai XF, Liu JQ, Woodiga SA, Chen C, Sun L, Hogaboam CM, Kunkel SL, Zheng P, Liu Y. Amelioration of sepsis by inhibiting sialidase-mediated disruption of the CD24-SiglecG interaction. Nat Biotechnol. 2011; 29(5):428-35. doi: 10.1038/nbt.1846. PubMed PMID: 21478876; PMCID: PMC4090080.
17. Chen W, Han C, Xie B, Hu X, Yu Q, Shi L, Wang Q, Li D, Wang J, Zheng P, Liu Y, Cao X. Induction of Siglec-G by RNA viruses inhibits the innate immune response by promoting RIG-I degradation. Cell. 2013; 152(3):467-78. Epub 2013/02/05. doi: 10.1016/j.cell.2013.01.011. PubMed PMID: 23374343.
18. Goris A, Maranian M, Walton A, Yeo TW, Ban M, Gray J, Dubois B, Compston A, Sawcer S. CD24 Ala/Val polymorphism and multiple sclerosis. Journal of neuroimmunology. 2006. PubMed PMID: 16631259.
19. Otaegui D, Saenz A, Camano P, Blazquez L, Goicoechea M, Ruiz-Martinez J, Olaskoaga J, Emparanza JA, Lopez de Munain A. CD24 V/V is an allele associated with the risk of developing multiple sclerosis in the Spanish population. Multiple sclerosis (Houndmills, Basingstoke, England). 2006; 12(4):511-4. Epub 2006/08/12. PubMed PMID: 16900767.
20. Wang L, Lin S, Rammohan K, Liu Z, Liu J, Liu R-H, Guinther N, Zhou Q, Wang T, Zheng X, Birmingham DJ, Rovin BH, Herbert LA, Wu Y, Lynn DJ, Cooke G, Yu CY, Zheng P, Liu Y. A di-nucleotide deletion in CD24 confers protection against autoimmune diseases. Plos Genetics. 2007; 3:e49.
21. Zhou Q, Rammohan K, Lin S, Robinson N, Li 0, Liu X, Bai XF, Yin L, Scarberry B, Du P, You M, Guan K, Zheng P, Liu Y. CD24 is a genetic modifier for risk and progression of multiple sclerosis. Proc Natl Acad Sci USA. 2003; 100(25):15041-6. doi: 10.1073/pnas.2533866100. PubMed PMID: 14657362; PMCID: PMC299898.
22. Sanchez E, Abelson A K, Sabio JM, Gonzalez-Gay M A, Ortego-Centeno N, Jimenez-Alonso J, de Ramon E, Sanchez-Roman J, Lopez-Nevot M A, Gunnarsson I, Svenungsson E, Sturfelt G, Truedsson L, Jonsen A, Gonzalez-Escribano MF, Witte T, Alarcon-Riquelme M E, Martin J. Association of a CD24 gene polymorphism with susceptibility to systemic lupus erythematosus. Arthritis Rheum. 2007; 56(9):3080-6. Epub 2007/09/01. doi: 10.1002/art.22871. PubMed PMID: 17763438.
23. Sanchez E, Fernandez-Gutierrez B, Gonzalez-Gay M A, Balsa A, Garcia A, Rodriguez L, Pascual-Salcedo D, Gonzalez-Escribano MF, Martin J. Investigating the role of CD24 gene polymorphisms in rheumatoid arthritis. Annals of the rheumatic diseases. 2008; 67(8):1197-8. Epub 2008/07/16. doi: 10.1136/ard.2007.084475. PubMed PMID: 18621973.
24. Rueda B, Miranda-Filloy JA, Martin J, Gonzalez-Gay M A. Association of CD24 gene polymorphisms with susceptibility to biopsy-proven giant cell arteritis. The Journal of rheumatology. 2008; 35(5):850-4. Epub 2008/04/03. PubMed PMID: 18381780.
25. Lee YH, Bae S C. Association between functional CD24 polymorphisms and susceptibility to autoimmune diseases: A meta-analysis. Cell Mol Biol (Noisy-le-grand). 2015; 61(8):97-104. Epub 2016/01/01. PubMed PMID: 26718436.
26. Bokers S, Urbat A, Daniel C, Amann K, Smith KG, Espeli M, Nitschke L. Siglec-G deficiency leads to more severe collagen-induced arthritis and earlier onset of lupus-like symptoms in MRL/lpr mice. Journal of immunology (Baltimore, Md.: 1950). 2014; 192(7):2994-3002. Epub 2014/03/07. doi: 10.4049/jimmunol.1303367. PubMed PMID: 24600033.
27. Wigren M, Nilsson J, Kaplan MJ. Pathogenic immunity in systemic lupus erythematosus and atherosclerosis: common mechanisms and possible targets for intervention. Journal of internal medicine. 2015; 278(5):494-506. Epub 2015/02/28. doi: 10.1111/joim.12357. PubMed PMID: 25720452; PMCID: PMC4550575.
28. Kay R, Rosten PM, Humphries RK. CD24, a signal transducer modulating B cell activation responses, is a very short peptide with a glycosyl phosphatidylinositol membrane anchor. Journal of immunology (Baltimore, Md.: 1950). 1991; 147(4):1412-6. Epub 1991/08/15. PubMed PMID: 1831224.
29. Perry D, Sang A, Yin Y, Zheng YY, Morel L. Murine models of systemic lupus erythematosus. Journal of biomedicine & biotechnology. 2011; 2011:271694. Epub 2011/03/16. doi: 10.1155/2011/271694. PubMed PMID: 21403825; PMCID: PMC3042628.
30. Ge Y, Jiang C, Sung SS, Bagavant H, Dai C, Wang H, Kannapell CC, Cathro HP, Gaskin F, Fu SM. Cgnzl allele confers kidney resistance to damage preventing progression of immune complex-mediated acute lupus glomerulonephritis. J Exp Med. 2013; 210(11):2387-401. Epub 2013/10/09. doi: 10.1084/jem.20130731. PubMed PMID: 24101379; PMCID: PMC3804943.

We claim:

1. A method of treating lupus nephritis in a subject by administering a CD24 fusion protein comprising a mature human CD24 polypeptide comprising the sequence set forth in SEQ ID NO: 1 or 2, and a Fc region of a mammalian immunoglobulin (Ig) protein, wherein the Fc region is fused to the C-terminus of the mature human CD24 polypeptide.

2. The method of claim 1, wherein the subject has been previously treated with another drug.

3. The method of claim 1, wherein the immunoglobulin (Ig) protein is a human immunoglobulin (Ig) protein.

4. The method of claim 1, wherein the Fc region comprises a hinge region and CH2 and CH3 domains of the human Ig protein, and wherein the immunoglobulin (Ig) protein is selected from the group consisting of IgG1, IgG2, IgG3, IgG4, and IgA.

5. The method of claim 4, wherein the Fc region comprises a hinge region and CH2, CH3 and CH4 domains of IgM.

6. The method of claim 1, wherein the sequence of the CD24 fusion protein comprises the sequence set forth in SEQ ID NO: 6, 11, or 12.

7. The method of claim 1, wherein the CD24 fusion protein is produced using a eukaryotic protein expression system.

8. The method of claim 7, wherein the expression system comprises a vector contained in a Chinese Hamster Ovary cell line or a replication-defective retroviral vector.

9. The method of claim 8, wherein the replication-defective retroviral vector is stably integrated into the genome of a eukaryotic cell.

10. The method of claim 1, wherein the CD24 fusion protein is soluble.

11. The method of claim 1, wherein the CD24 fusion protein is glycosylated.

* * * * *